United States Patent
McCoy et al.

(10) Patent No.: US 9,856,525 B2
(45) Date of Patent: *Jan. 2, 2018

(54) DIGITAL ASSAYS WITH ASSOCIATED TARGETS

(71) Applicant: Bio-Rad Laboratories, Inc., Hercules, CA (US)

(72) Inventors: Adam M. McCoy, Davis, CA (US); Niels Klitgord, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 791 days.

This patent is subject to a terminal disclaimer.

(21) Appl. No.: 14/217,357

(22) Filed: Mar. 17, 2014

(65) Prior Publication Data

US 2014/0274786 A1    Sep. 18, 2014

Related U.S. Application Data

(60) Provisional application No. 61/791,801, filed on Mar. 15, 2013, provisional application No. 61/909,776, filed on Nov. 27, 2013.

(51) Int. Cl.
C12Q 1/68        (2006.01)

(52) U.S. Cl.
CPC ......... *C12Q 1/6851* (2013.01); *C12Q 1/6844* (2013.01)

(58) Field of Classification Search
None
See application file for complete search history.

(56) References Cited

U.S. PATENT DOCUMENTS

| | | |
|---|---|---|
| 2009/0148837 A1 | 6/2009 | Ecker et al. |
| 2010/0173394 A1* | 7/2010 | Colston, Jr. ........... B01F 3/0807 435/287.2 |
| 2012/0252015 A1 | 10/2012 | Hindson et al. |
| 2012/0322058 A1 | 12/2012 | Regan et al. |
| 2012/0329664 A1 | 12/2012 | Saxonov et al. |
| 2013/0040841 A1 | 2/2013 | Saxonov et al. |

FOREIGN PATENT DOCUMENTS

| | | |
|---|---|---|
| WO | 2012129187 A1 | 9/2012 |
| WO | 2012129436 A1 | 9/2012 |

OTHER PUBLICATIONS

European Patent Office, "Extended European Search Report" in connection with related European Patent Application No. 14765653.2, dated Oct. 28, 2016, 10 pages.
Dube, Simant et al., "Mathematical Analysis of Copy Number Variation in a DNA Sample Using Digital PCR on a Nanofluidic Device" PLoS ONE, vol. 3, Issue 8, Aug. 2008, 9 pages.
McCaughan, Frank et al., "Single-molecule genomics" Journal of Pathology, vol. 220, Nov. 19, 2009, pp. 297-306.
Pole, Jessica C. M. et al., "Single-molecule analysis of genome rearrangements in cancer", Nucleic Acids Research, vol. 39, No. 13, Apr. 27, 2011, 13 pages.
European Patent Office, "Partial Supplementary European Search Report" in connection with related European Patent Application No. 14765653.2, dated Jul. 22, 2016, 7 pages.
Zhishan Hua et al., "Multiplexed Real-Time Polymerase Chain Reaction on a Digital Microfluidic Platform", Analytical Chemistry, 82(6): 2310-2316, dated Mar. 15, 2010, 16 pages.
Blaine R. Copenheaver, Authorized Officer, Commissioner for Patents, "International Search Report" in connection with related PCT Patent Application No. PCT/US2014/030896, dated Aug. 21, 2014, 3 pages.
Blaine R. Copenheaver, Authorized Officer, Commissioner for Patents, "Written Opinion of the International Searching Authority" in connection with related PCT Patent Application No. PCT/US2014/030896, dated Aug. 21, 2014, 19 pages.

* cited by examiner

*Primary Examiner* — Prabha Chunduru
(74) *Attorney, Agent, or Firm* — Kolisch Hartwell, P.C.

(57) ABSTRACT

System, including methods, apparatus, and compositions, for performing a digital assay with associated targets. In some embodiments, the assay of associated targets in partitions may lower the limit of detection (LOD) or otherwise increase assay sensitivity, accuracy, and/or specificity. The targets may represent spaced or overlapping regions of the same template and/or each may represent a region from a different complementary strand of the same template. In some embodiments, the associated targets may be provided by a type of biological particle, and the target content of partitions may be used to identify and quantify the type of biological particle in a sample.

12 Claims, 12 Drawing Sheets

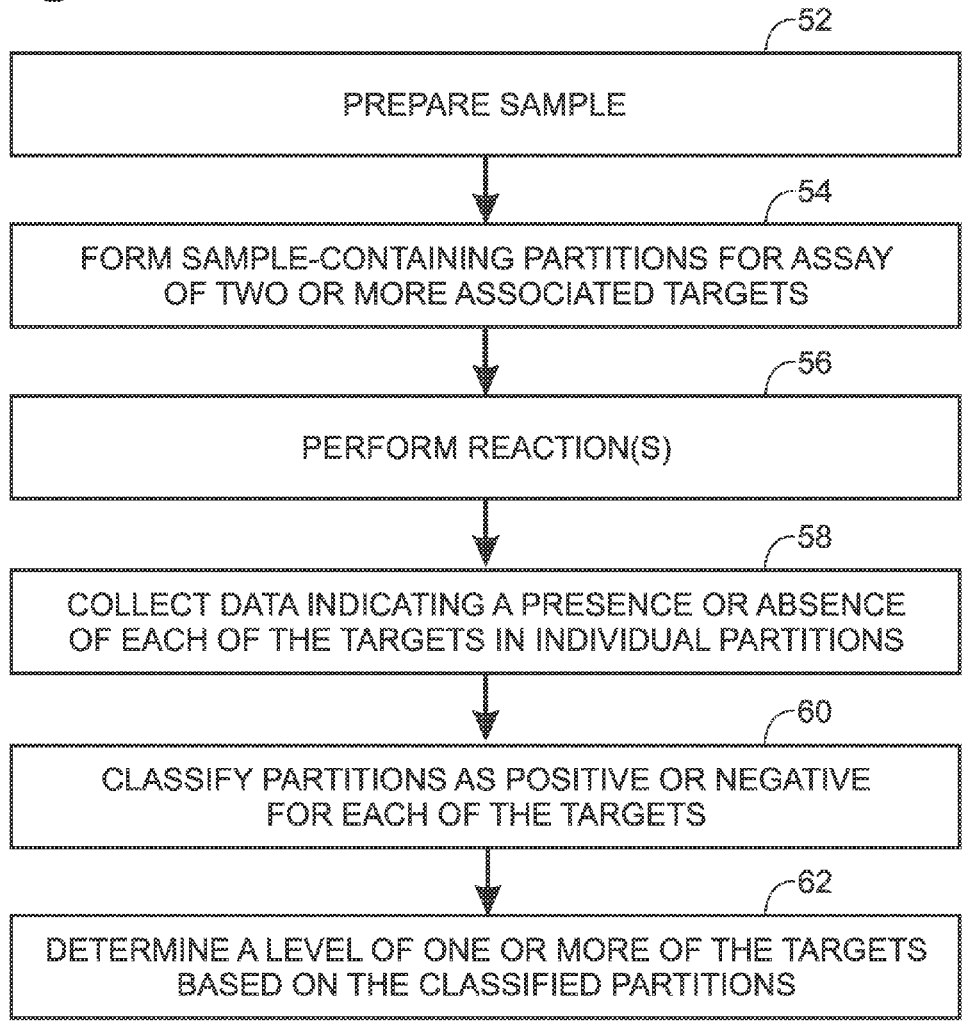
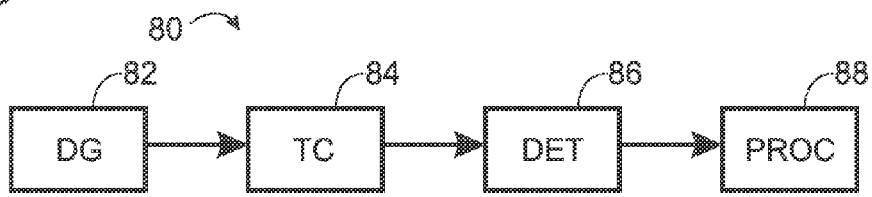

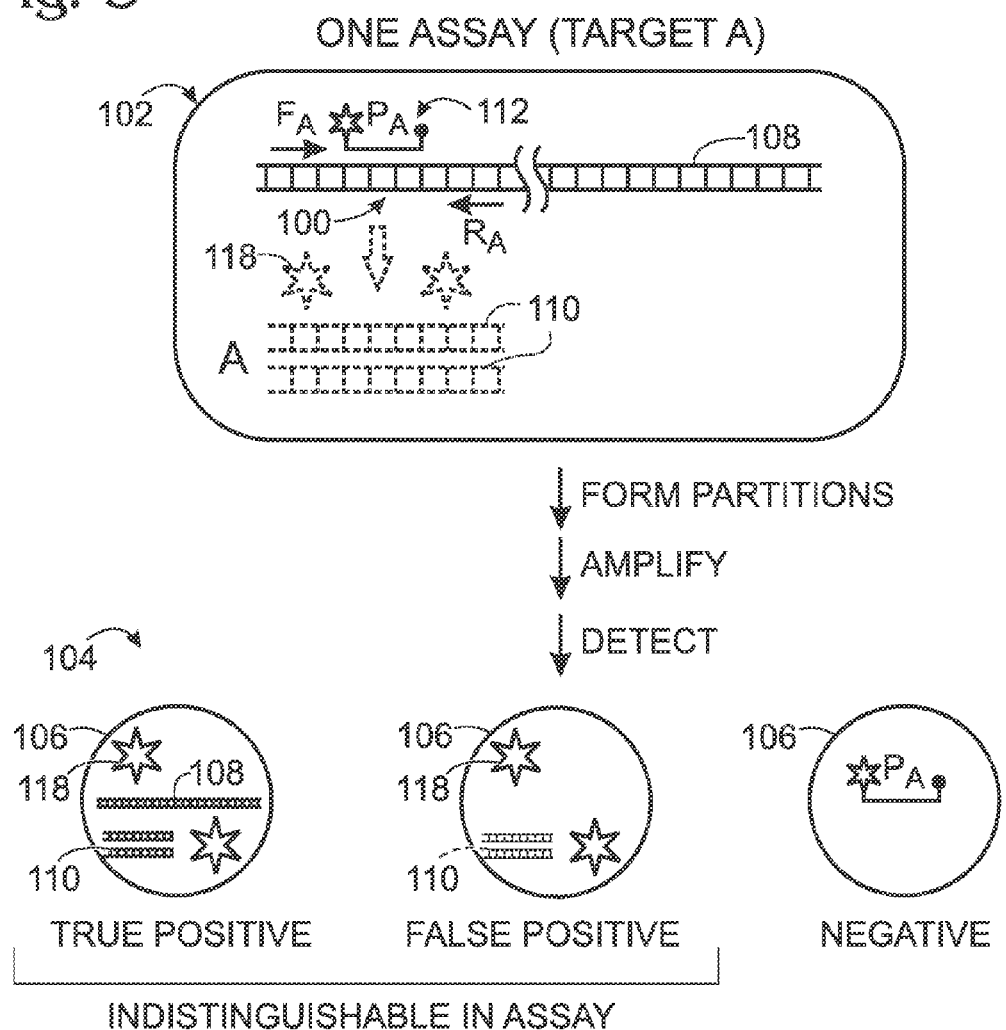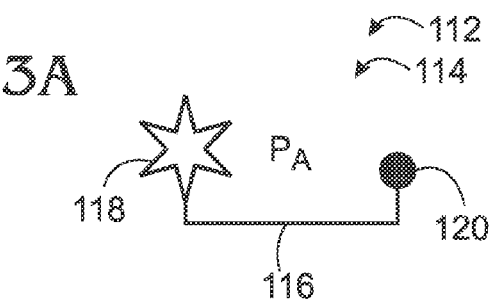

Fig. 4
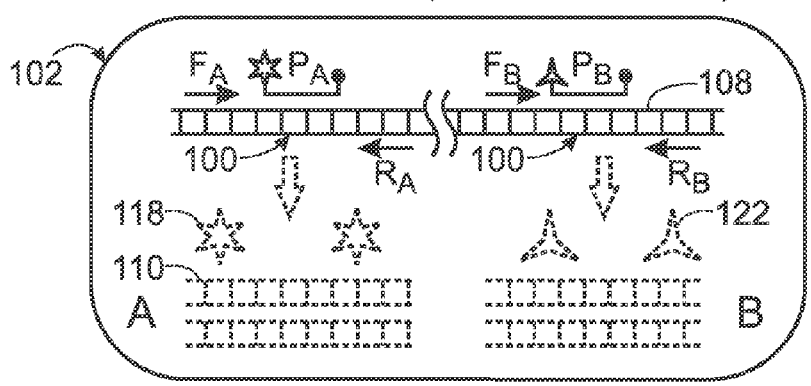
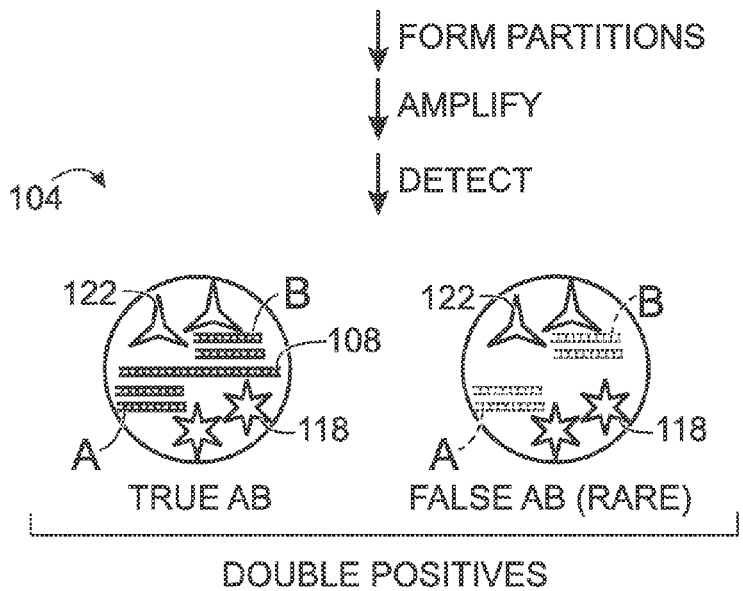
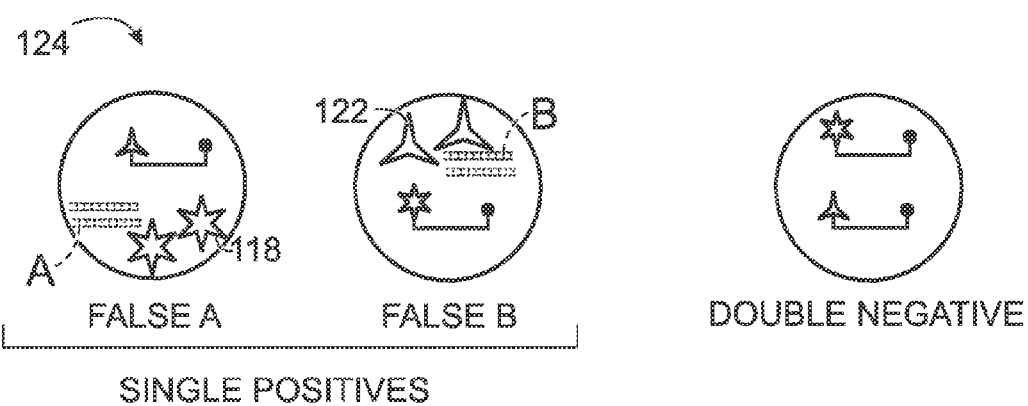

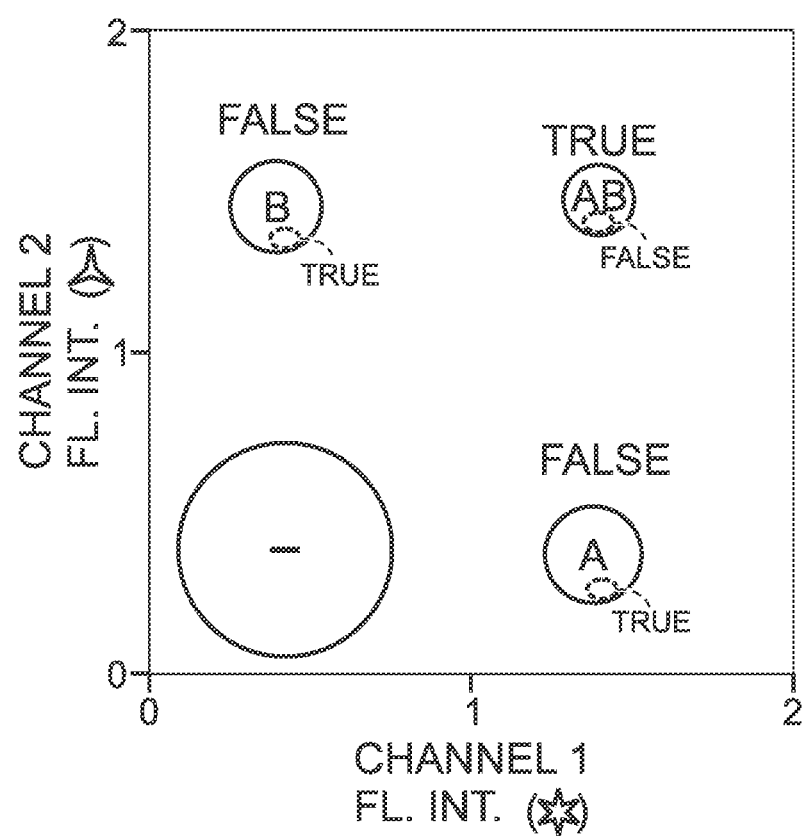

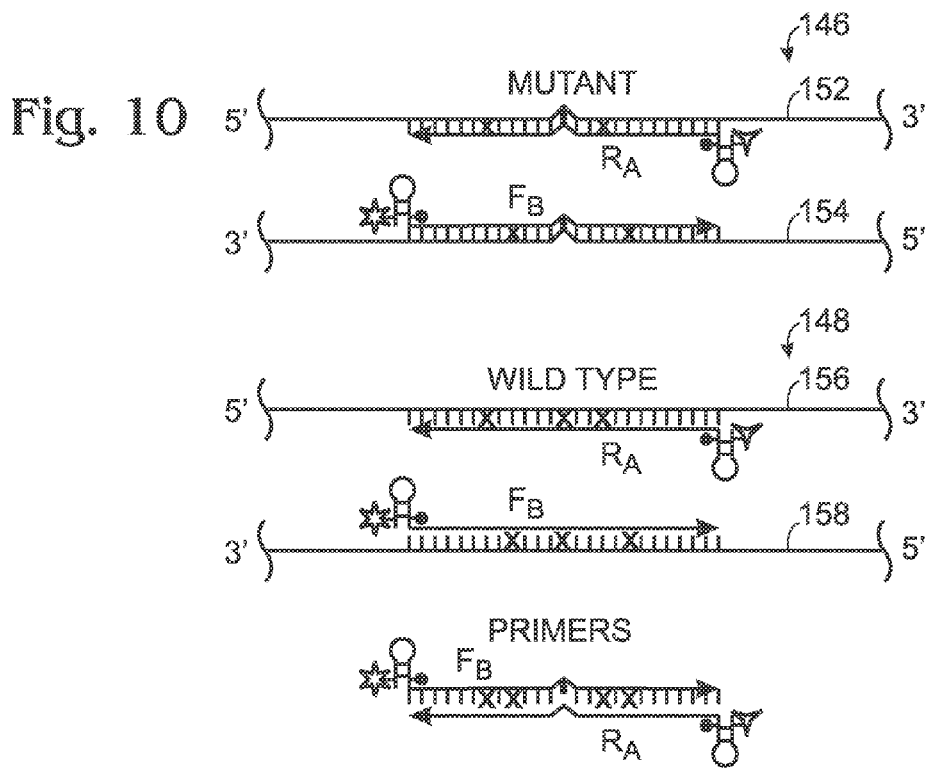

↓ FORM PARTITIONS
↓ AMPLIFY - LOWER STRINGENCY
↓ AMPLIFY - HIGHER STRINGENCY

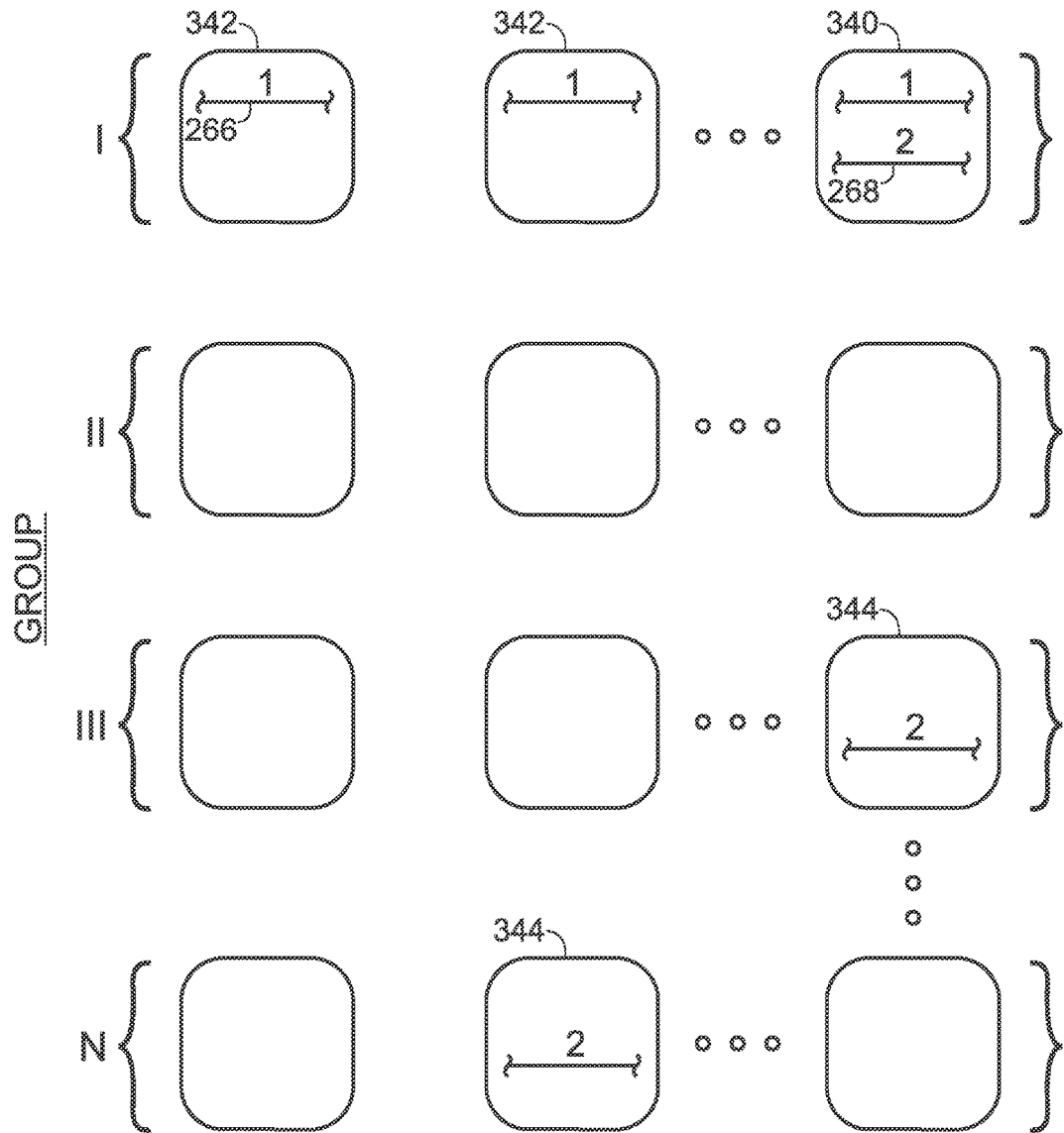

DIGITAL ASSAYS WITH ASSOCIATED TARGETS

CROSS-REFERENCES TO PRIORITY APPLICATIONS

This application is based upon and claims the benefit under 35 U.S.C. §119(e) of U.S. Provisional Patent Application Ser. No. 61/791,801, filed Mar. 15, 2013; and U.S. Provisional Patent Application Ser. No. 61/909,776, filed Nov. 27, 2013. Each of these priority applications is incorporated herein by reference in its entirety for all purposes.

Cross-References to Other Materials

This application incorporates herein by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; U.S. patent application Ser. No. 14/099,750, filed Dec. 6, 2013; U.S. patent application Ser. No. 14/171,754, filed Feb. 3, 2014; U.S. patent application Ser. No. 14/171,761, filed Feb. 3, 2014; U.S. patent application Ser. No. 14/191,295, filed Feb. 26, 2014; and Joseph R. Lakowicz, PRINCIPLES OF FLUORESCENCE SPECTROSCOPY $2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions, such as with Poisson statistics.

Digital assays frequently rely on amplification of a nucleic acid target in partitions to enable detection of a single copy of an analyte. Amplification may be conducted via the polymerase chain reaction (PCR), to achieve a digital PCR assay. Amplification of the target can be detected optically from a reporter, such as a fluorescent probe included in the reaction. In particular, the probe can include a fluorophore that provides a fluorescence signal indicating whether or not the target has been amplified.

SUMMARY

The present disclosure provides a system, including methods, apparatus, and compositions, for performing a digital assay with associated targets. In some embodiments, the assay of associated targets in partitions may lower the limit of detection (LOD) or otherwise increase assay sensitivity, accuracy, and/or specificity. The targets may represent spaced or overlapping regions of the same template and/or each may represent a region from a different complementary strand of the same template. In some embodiments, the associated targets may be provided by a type of biological particle, and the target content of partitions may be used to identify and quantify the type of biological particle in a sample.

BRIEF DESCRIPTION OF THE DRAWINGS

FIG. 1 is a flowchart of an exemplary method of performing a multiplexed digital assay with associated targets to lower the limit of detection or otherwise increase assay sensitivity and/or accuracy, in accordance with aspects of the present disclosure.

FIG. 2 is a schematic view of an exemplary system for performing the multiplexed digital assay of FIG. 1, in accordance with aspects of the present disclosure.

FIG. 3 is a schematic diagram illustrating an exemplary, less-sensitive singleplex digital assay performed in partitions on only one target (target A), with the strategy for target amplification and detection presented in an exemplary bulk phase above the partitions (copies of an amplicon and a degraded form of a probe are shown in broken lines) and with exemplary true-positive and false-positive partitions and a true-negative partition shown below the bulk phase, in accordance with aspects of the present disclosure.

FIG. 3A is a magnified view of the probe of FIG. 3.

FIG. 4 is a schematic diagram illustrating an exemplary, more-sensitive multiplexed digital assay performed in partitions on a pair of linked targets (targets A and B), with the strategy for target amplification and detection in partitions with spectrally distinct probes presented in an exemplary bulk phase above the partitions (copies of amplicons and degraded forms of the probes are shown in broken lines), and with exemplary true double-positive (AB), false double-positive (AB), false single-positive (A or B), and true double-negative partitions shown below the bulk phase, in accordance with aspects of the present disclosure.

FIG. 4A is a schematic view of an exemplary scatter plot of fluorescence data that may be collected from partitions in the multiplexed digital assay of FIG. 4, in accordance with aspects of the present disclosure.

FIG. 10 illustrates exemplary labeled, allele-specific primers for the allele-specific assays of FIG. 9 and shows how mismatches ("X") allow the primers to bind selectively to the desired allelic template, in accordance with aspects of the present disclosure.

FIG. 11 is a flowchart of an exemplary method of performing a multiplexed digital assay for a single-stranded template and a double stranded template, in accordance with aspects of the present disclosure.

FIG. 18 is a schematic diagram of different types of biological particles that may be present in a sample assayed as described herein, with the types arranged in taxonomic groups (taxa) of the same rank, and with target content of the types shown only for a particular pair of targets (targets 1 and 2) of the sample to be assayed, in accordance with aspects of the present disclosure.

DETAILED DESCRIPTION

Figure 5:
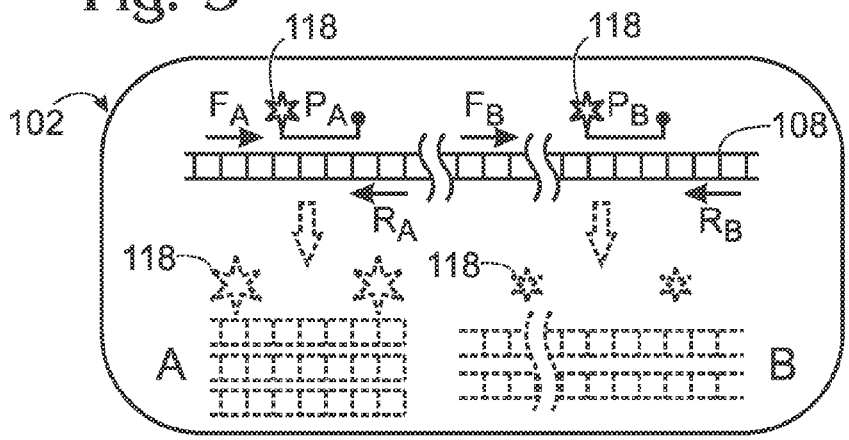
FIG. 5 is a schematic diagram illustrating another exemplary bulk phase for the multiplexed digital assay of FIG. 4, with the spectrally distinct probes of FIG. 4 replaced with spectrally similar probes that are distinguishable by intensity after target amplification, optionally at least in part due to a difference in probe concentrations and/or amplification efficiency of the two targets, in accordance with aspects of the present disclosure.

The present disclosure provides a system, including methods, apparatus, and compositions, for performing a digital assay with associated targets. In some embodiments, the assay of associated targets in partitions may lower the limit of detection (LOD) or otherwise increase assay sensitivity, accuracy, and/or specificity. The targets may represent spaced or overlapping regions of the same template and/or each may represent a region from a different complementary strand of the same template. In some embodiments, the associated targets may be provided by a type of biological particle, and the target content of partitions may be used to identify and quantify the type of biological particle in a sample.

An exemplary method of performing a digital assay is provided. In the method, partitions may be formed, with each partition including a portion of a sample that contains a first target associated with a second target. Data may be collected indicating a presence or absence of each target in individual partitions. Each of a plurality of the partitions may be classified as positive or negative for each of the targets based on the data. Partitions having an indicated presence of only the first target in the data may be classified as negative for both targets. A level of the first target may be determined.

Another exemplary method of performing a digital assay is provided. In the method, partitions may be formed, with only a subset of the partitions containing at least one copy of a template. The template may contain a first target sequence and a second target sequence. The first target sequence and the second target sequence may be amplified in the partitions. Data may be collected for amplification of the first target sequence and the second target sequence in the partitions. The data may be processed such that a given partition is classified as positive for both targets if the partition tests positive for both targets and is classified as negative for both targets if the partitions tests negative for either or both targets. A concentration of the first target may be determined based on the processed data.

Still another method of performing a digital assay is provided. In the method, partitions may be provided, with each partition containing a single-stranded first template and a double-stranded second template having a first strand and a second strand. The first template and the second template each may be present in only a subset of the partitions. The first template and the first strand each may include a first target sequence and the second strand may include a second target sequence. The first target sequence and the second target sequence may be amplified in the partitions. Data may be collected for amplification of the first target sequence and the second target sequence in individual partitions. A level of each of the single-stranded first template and the double-stranded second template may be determined based on the data.

An exemplary method of sample analysis is provided. In the method, a sample comprising at least two types of biological particles and/or nucleic acid therefrom may be provided. Each type of biological particle may contain a different target set or subset composed of at least one of two or more targets. Partitions each containing a portion of the sample may be formed. A presence or absence of each of the two or more targets in each of a plurality of the partitions may be determined. A level of a type of biological particle containing a particular target set or subset of the two or more targets may be determined.

An exemplary set is provided. The set may comprise a plurality of partitions each containing a portion of a same sample and each having a volume of less than 100 nL. The sample may comprise at least two types of biological particles and/or nucleic acid therefrom. Each type of biological particle may contain a different target set or subset composed of at least one of two or more targets. The two or more targets may include a first target present in a plurality of taxa of the same taxonomic rank, and a second target present in only one taxon of the rank. Only a subset of the partitions may contain at least one copy of any one of the targets. Each partition also may comprise at least one reporter to detect the first target and a second reporter, and reagents sufficient for amplification of each of the targets.

Digital assays can suffer from the presence of false positives, which may, for example, be partitions that test positive for a target not actually present, that detect a partial product, or that contain the target as a contaminant from a source other than the sample being assayed. Such false positives can reduce the sensitivity and reliability of the assays. New approaches are needed to address false positives.

It is often desirable to achieve the lowest limit of detection (LOD) possible for a particular target sequence or target cell/organism. The LOD for a digital assay can be determined by the frequency of false-positive partitions ("false positives") for a given target (i.e., the false-positive rate). This frequency can determine the target concentration at which true-positive partitions ("true positives") can be reliably distinguished from the background noise created by the false positives. Even a small number of false positives can have a relatively large effect on the LOD.

A large part of the problem generally arises from the need to have low-abundance samples (i.e., containing only a small amount of the target) significantly different from negative controls. The inherent variance of data collected from low-abundance samples means that the power to distinguish negative samples from low-abundance samples is poor. The variance of low-abundance samples is inherently high due to sampling error. The sampling error generally cannot be changed fundamentally, so the most practical method to improve the LOD is to reduce the false-positive rate. Assay design is one component in creating an assay with a low false-positive rate.

Another way to drive down the false-positive rate is to perform a multiplexed assay composed of two (or more) assays targeting the same template, and look for co-localization to the same partitions to distinguish true positives from false positives. The true positives will result in co-localized signal because the template contains the targets for both assays on a single copy of the template. The effective false-positive rate in this approach, the dual false-positive rate, should be much lower than the single false-positive rate. Both assays can have an independent false positive rate. Accordingly, the chance that a partition will be false positive for both assays can be extremely low when the frequency of single false positives is low. As a result, false double-positives that are template-independent can be nearly eliminated. This drives the LOD down because true positives (i.e., double positives) can be more easily distinguished from false positives.

The approach disclosed herein may be particularly useful in an assay for a rare target where alternate target molecules, such as human genomic DNA for normalization, can be sampled in separate wells. This approach has potential for use in diagnostics as well as basic research. The approach may be particularly useful for applications where the assay design space is such that it is difficult to design a single assay with an intrinsically low false-positive rate.

There may be a false-negative rate due to assay failures or degradation of the DNA. This can be measured separately and accounted for, or otherwise compensated for when target levels are calculated.

There are several specific variations of this approach that could be advantageous for specific applications. Use of two target assays of linked targets could help to distinguish true positives (provided by template in the sample being assayed) from false positives created by contamination of the assay with a partial template, such as amplicon copies, from a source other than the sample. Contaminating templates/amplicons for the two target assays would be unlinked and thus would not co-localize to partitions at high frequency as long as the contamination is not severe. Even when the contamination is severe, dilution could be used to bring the concentration of contaminating amplicons into a range where linked and unlinked targets can be distinguished. Contamination could be produced by only one of the amplicons or both. Even if the contamination included both amplicons, true positives (from the sample) would be distinguishable from false positives (from contamination) due to target linkage.

In some embodiments, two allele-specific assays for the same allele may be utilized to lower the LOD (e.g., see Section III). The two assays could employ Taqman® probes if they are sufficiently offset. In other examples, signals could be detected from two labeled primers that report amplification of the respective targets, with a different luminophore (or the same luminophore) attached to each primer. Exemplary primers that are probes include Scorpion® primers, Amplifluor® primers, fluorescent primers with an internal RNA base, etc. In some cases, two allele-specific primers could be used for amplification of respective targets containing the same single-nucleotide polymorphism (SNP), with one primer targeting each strand and, optionally, with each ending with the 3' base of the primer on the SNP site for the respective strands. In other examples, an intercalating dye, such as EvaGreen® dye, can be used as a generic reporter for both targets, with the intensity of fluorescence distinguishing the two targets.

Targets specific to distinct strands of the template may overlap by any suitable amount. In some examples, other than at one or more allele-specific nucleotide base pairs, the targets may not overlap. In other embodiments, the targets may overlap by two, three, five, or ten nucleotides, or over a majority of the length of the allele-specific primers, among others. In any event, each target may have its own pair of primers and, optionally, its own probe, if a probe-based assay is used for detection.

The approach for allele detection disclosed herein can substantially increase sensitivity. Allele-specific PCR with only one target can have a significant false-positive rate. The primer sequence for an allele-specific target is incorporated into the corresponding amplicon, so once a mis-priming event occurs on the wrong allele in a partition (e.g., mis-priming on the wild-type allele in an assay for a mutant allele), the discrimination between alleles is lost for that particular partition. With two targets (e.g., on opposite strands) for the same allele, a mis-priming event with the allele-specific primer for one of the target assays, to generate one of the amplicons, is independent of a mis-priming event needed for generation of the other amplicon for the other assay. Accordingly, a false positive for one of the assays may result, but not a double false positive for both assays in the same partition, unless there is independent mis-priming for both targets. As with the general method, the double false-positive rate should be much less than the rate for each single false positive.

Estimates of target levels (e.g., target concentrations) may be adjusted/corrected in various ways. The concentration determined may account for expected double false positives based on the two single false-positive rates for the targets. For example, the expected number of double false positives may be subtracted from the number of double positives observed, to permit determination of an adjusted concentration that accounts for double false positives occurring by chance. Such as adjustment may be small (e.g., ignored) at most loading conditions where the LOD is relevant, except in certain situations when contamination with amplicon/template fragments occurs. The concentration determined also or alternatively may include a correction for single positives that test positive for only one of the targets (effectively, false negatives) and actually contain at least one of the targets from the sample. Such a correction may be based on the degree of linkage between the targets (e.g., based on the degradation state, if any, of the template), the intrinsic assay failure rates of the assays, or a combination thereof, among others.

Further aspects of the present disclosure are presented in the following sections: (I) definitions, (II) system overview, (III) exemplary digital assays with associated targets, (IV) identification of biological particles based on associated targets, and (V) examples.

I. Definitions

Technical and scientific terms used in this disclosure have the meanings that are commonly recognized by those skilled in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Spring Harbor Lab Press (Cold Spring Harbor, N.Y. 1989). However, the following terms may have additional or alternative definitions, as described below, which are provided to facilitate understanding of certain terms used frequently herein and are not intended to limit the scope of the present disclosure.

The term "comprise" or "include" and variations thereof such as "comprises," "comprising," "includes," and "including," when referring to a step or an element, are intended to mean that the addition of further steps or elements is optional and not excluded. Any methods, devices, and materials similar or equivalent to those described herein can be used in the practice of the invention.

A "sample" refers to a compound, composition, and/or mixture of interest, from any suitable source(s). A sample is the general subject of interest for an assay that analyzes an aspect of the sample, such as an aspect related to at least one target that may be present in the sample. Samples may be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on a sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others.

The sample may be of any suitable type for any suitable purpose. Clinical samples may include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Environmental samples may include water, soil, aerosol, and/or air, among others. Research samples may include cultured cells, primary cells, bacteria, spores, viruses, small organisms, any of the clinical samples listed above, or the like. Additional samples may include foodstuffs, weapons components, biodefense samples to be tested for bio-threat agents, suspected contaminants, and so on.

Samples may be collected for diagnostic purposes (e.g., the quantitative measurement of a clinical analyte such as an infectious agent) or for monitoring purposes (e.g., to determine that an environmental analyte of interest such as a bio-threat agent has exceeded a predetermined threshold).

Biological samples can be obtained from or may contain any suitable biological organism(s), e.g., at least one an animal, plant, fungus, bacterium, or other organism, or at least one portion thereof (e.g., one or more cells or nucleic acid therefrom). In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue and/or bodily fluid obtained from the an organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, and stem cells; stool, urine, etc. A biological sample can be obtained from a biopsy.

In some embodiments, the sample is an environmental sample. For example, an air, water, or soil sample. The sample can derive from a particular environmental source such as a particular lake, region, aquifer, watershed, or particular ecosystem or geographical area. Alternatively, the sample can be obtained from a swipe, scrape, etc. of an area, object, or space. For example, the same may be an air or water sample, or a swipe or scrape, from a hospital room, bed, or other physical object.

The sample can contain particles of interest. However, in some cases, the sample does not contain particles of interest. For example, the sample can be suspected of containing a particle type of interest, such as from methicillin-resistant *Staphylococcus aureus*. Alternatively, or in addition, the sample can include other types of particles that are not of interest. Accordingly, the sample may include a mixture of particles of interest and not of interest. In some cases, the sample may contain nucleic acid prepared from biological particles.

The sample can be prepared to improve efficient identification of a target. For example, the sample can be purified, fragmented, fractionated, homogenized, or sonicated. In some embodiments, one or more targets can be extracted or isolated from a sample (e.g., a biological sample). In some embodiments, the sample is enriched for the presence of the one or more targets. In some embodiments, the targets are enriched in the sample by an affinity method, e.g., immunoaffinity enrichment, or by hybridization. For example, the sample can be enriched for biological particles/targets in general, or for particular types of particles/targets, by immunoaffinity, centrifugation, or other methods known in the art to capture and/or isolate particles/targets.

In some embodiments, the sample is enriched for targets using size selection (e.g., to remove small/short molecules and/or large/long molecules). In other embodiments, the sample is enriched for RNA molecules by selecting for the poly-A tail of eukaryotic messenger RNA. For example, the sample can be passed over an oligo-dT column, and poly-A enriched RNA can be eluted for further analysis.

The terms "partitioning," "partitioned," and the like refer to separation of fluid into a plurality of separate portions, or "partitions." Partition formation may involve distributing/dividing any suitable amount including up to all of a fluid volume (which may be described as a bulk phase, a sample-containing fluid, a sample, and/or a mixture) to partitions. Each partition of a set of partitions may include a portion of the same fluid volume and may be and/or include a volume of fluid that is isolated from fluid volumes of other partitions of the set. The partitions may be separated from one another by a fluid/liquid phase, such as a continuous phase of an emulsion, by a solid phase, such as at least one wall of compartment (such as a container), or a combination thereof, among others. In some embodiments, each partition may be held by a distinct compartment, such as a distinct well, channel, or chamber. In some embodiments, the partitions may be droplets disposed in a fluid continuous phase, which may be liquid, such that the droplets and the continuous phase collectively form an emulsion. In some embodiments, a fluid partition (e.g., a droplet) is an aqueous droplet that is surrounded by an immiscible carrier fluid (e.g., oil).

A partition may be a sample partition containing a portion of a sample. Partitions may be substantially uniform in size or may have distinct sizes (e.g., sets of partitions of two or more discrete, uniform sizes). Exemplary partitions are droplets. Partitions may also vary continuously in size with a predetermined size distribution or with a random size distribution.

A "droplet" refers to a small volume of fluid, generally liquid, surrounded by a different fluid, generally an immiscible fluid, such as a continuous phase of an emulsion. The volume of a droplet, and/or the average volume of droplets in an emulsion, may, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, or of about 1000 to 1 micrometers, among others. A droplet may be spherical or nonspherical. A droplet may be a simple droplet or a compound droplet, that is, a droplet in which at least one droplet encapsulates at least one other droplet.

"Oil" refers to any fluid that is immiscible with water. In some examples, oil may be an organic fluid that includes carbon and any combination of hydrogen, fluorine, silicon, and oxygen, among others. Any of the emulsions disclosed herein may be a water-in-oil (W/O) emulsion (i.e., aqueous droplets in a continuous oil phase). The oil may, for example, be or include at least one silicone oil, mineral oil, fluorocarbon oil, vegetable oil, or a combination thereof, among others. Any other suitable components may be present in any of the emulsion phases, such as at least one surfactant, reagent, sample (i.e., portions thereof), other additive, label, particle, or any combination thereof.

A "target" refers to an analyte of interest (or a region thereof). A target interchangeably may be termed an analyte or an identification signature. The target may be a subject of an assay, such as a multiplexed assay, and may be contained by a sample and/or contained collectively by a set of partitions each containing a portion of the sample. The target may be a molecule (a target molecule), an assembly or complex of two or more molecules (a target assembly/complex), a biological particle (a target biological particle (e.g., a target cell)), or the like. The target may be a portion (or all) of a molecule, a portion (or all) of an assembly/complex, or a portion (or all) of a particle. Exemplary targets include nucleic acids, nucleic acid sequences, proteins (e.g., an antibody, enzyme, growth factor, clotting factor, phosphoprotein, etc.), protein sequences (e.g., epitopes/haptens), carbohydrates, metabolites, and biological particles. Exemplary target sequences may be at least 10, 15, 20, 25, 30, 40, or 50 nucleotides in length.

In some examples, the target may be a target sequence contained by a molecule or complex, and may form only a portion (or all) of the molecule or complex. The target sequence may, for example, be a sequence of nucleotides (e.g., a single-stranded or double-stranded sequence), a sequence of amino acids, a sequence of sugars, or the like. A target may be a template in some cases (or may be provided by a template). Exemplary target sequences may be provided by genomic DNA, mitochondrial DNA, chloroplast DNA, plastid DNA, complementary DNA, RNA (e.g., genomic RNA and/or a transcript), and the like. A "target molecule" refers to a molecule to be detected in a sample.

A "biological particle" refers to a particle containing biological molecules, such as macromolecules (e.g., proteins, nucleic acid, and/or polysaccharides, among others) and/or macromolecular complexes (e.g., ribonucleoprotein complexes). The biological particle may be a biological cell (interchangeably termed a cell), a virion (interchangeably termed a viral particle), an organelle (interchangeably termed a subcellular particle), or the like. In some embodiments, the biological particle may be a type of microbe (which interchangeably may be termed a microorganism and/or a single-celled organism), such as a type of bacterium, virus, protozoan, yeast, archaea, etc. In some embodiments, cells may be provided by a multicellular organism (e.g., cells from a human, horse, mouse, frog, fish, insect, sponge, fungus, etc.). Cells can include cells of a particular tissue type, a particular phenotype (e.g., proliferating, stimulated, etc.), or a particular disease (e.g., infected cells, cancer cells, etc.), among others. Biological particles in a sample (or only potentially in a sample) may be of at least one, two or more, or three or more different "types." The different types of biological particles may be distinguishable genetically, epigenetically, and/or phenotypically. The different types may be taxonomically related but distinguishable, such as belonging to the same taxon of a particular taxonomic rank (kingdom, phylum, class, order, family, genus, and/or species), among others. For example, each of at least a pair of different types may represent different genera or the same family, different species of the same genus, or different strains or variants of the same species, among others.

Strains/variants may have any suitable number of genetic/epigenetic differences, including a single gene, a single nucleotide difference, and/or a single epigenetic difference. The pair of different types may be belong to different taxa of the same taxonomic rank, but may share a genetic region or a set of genetic regions.

A "target biological particle" such as a "target cell" or a "target virion" may be a biological particle of interest, such as a type of cell or virion, to be detected in a sample. The target biological particle interchangeably may be described as an "analyte particle" and may be distinguished from a "non-analyte (non-target) particle." In some embodiments, the particle of interest contains a target content (e.g., of target molecules and/or target sequences) that distinguishes the target particle from other types of particles that can be in a sample being assayed. For example, the particle of interest can contain any of the targets disclosed herein, such as a target sequence or a set of target sequences that are characteristic of the target particle and that identify the particle of interest as belonging to a type of interest relative to other types of particles that are not of interest.

A set of partitions containing one or more targets at "partial occupancy" refers to a situation in which each target is absent from at least one partition of the set. Accordingly, at partially occupancy, only a subset of the set of partitions contain at least one copy of each target to be assayed. For example, with a multiplexed assay performed on a first target and a second target, only a first subset of the partitions contain the first target, and only a second subset of the partitions contain the second target. The first subset and the second subset of the partitions may be the same subset, if the first target and the second target are fully associated with each other when the partitions are formed. Alternatively, the first subset and the second subset of the partitions may be different if the first target and the second target are not fully associated with each other when the partitions are formed. In some cases, if the targets are not fully associated, each partition of a different third subset may contain at least one copy of each target. Accordingly, with partial occupancy, one or more (e.g., a plurality) of the partitions contain no copies of the first target, one or more (e.g., a plurality) of the partitions may contain a single copy (only one copy) of the first target, and, optionally, yet one or more of the partitions (e.g., the rest of the partitions) may contain two or more copies of the first target. Similarly, with partial occupancy, one or more (e.g., a plurality) of the partitions contain no copies of the second target, one or more (e.g., a plurality) of the partitions may contain a single copy (only one copy) of the second target, and, optionally, yet one or more of the partitions (e.g., the rest of the partitions) may contain two or more copies of the second target.

The term "partial occupancy" is not restricted to the case where there is no more than one copy of a particular target in any partition. Partitions containing a target at partial occupancy may, for example, contain an average of more than, or less than, about one copy, two copies, or three copies, among others, of the target per partition when the partitions are provided or formed. Copies of a target may have a random distribution among the partitions, which may be described as a Poisson distribution. In some cases, a significant number of the partitions (e.g., at least about 1%, 2%, 5%, 10%, or 20%, among others, of the partitions) each may contain a copy of each of at least two different targets, and/or a plurality of the partitions each may contain at least one copy of all targets to be assayed.

A pair of targets that are "associated" refers to targets that distribute together to the same partitions from the same bulk phase at a frequency greater than by chance alone. Respective copies of the pair of targets may be associated with each other by being present together in or on the same biological particle (e.g., the same biological cell, virion, subcellular organelle, etc.). As another example, the pair of associated targets may be "linked," that is, connected to each other (covalently and/or by direct or indirect non-covalent binding such as by base pairing, among others). The associated targets may have any suitable degree of association and/or linkage of at least about 50%, 80%, 90%, or 100% in the sample before and/or during partition formation. The degree of association (and/or linkage) indicates the percentage of copies of one target that are each associated with (and/or linked to) at least one copy of the other target. The degree of association/linkage of targets may be known a priori or tested. The degree of association indicates a percentage of the targets that are connected to each other, confined to the same compartment (e.g., the same cell) within the sample, and/or the frequency with which the targets distribute together to the same partitions, after correction for co-localization by chance. Targets that occupy the same partition, whether due to a physical connection and/or forced spatial proximity during partition formation, or due to chance, may be described as being co-localized or coincident in the partition. Targets that have a high degree of association are co-localized to the same partitions at a corresponding high frequency, whether the targets are abundant or rare in the sample. For example, targets that have 90% association should co-localize in at least 90% of the partitions that contain at least one of the targets. In contrast, targets that have no association should co-localize according to the product of the probabilities of finding each target in a given partition, which varies with the concentration of the targets.

A "nucleic acid" refers to a molecule/assembly comprising a chain of nucleotide monomers. A nucleic acid may be single-stranded, double-stranded, triple-stranded, or a combination thereof, among others. A single chain of a nucleic acid may be composed of any suitable number of nucleotides, such as at least 2, 5, 10, 20, 50, 100, 200, 500, or 1000 nucleotides, among others. Generally, the length of a nucleic acid chain corresponds to its source, with synthetic nucleic acids (e.g., primers and probes) typically being shorter, and biologically/enzymatically generated nucleic acids (e.g., nucleic acid analytes) typically being longer. "Nucleic acid" refers to a plurality of nucleic acids of different sequence, length, type, or a combination thereof, among others.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acids (LNA), threose nucleic acids (TNA), phosphorothioates, phosphoramidates, methyl phosphonates, chiral-methyl phosphonates, 2-O-methyl ribonucleotides, and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil), and guanine pairs with cytosine. A nucleic acid chain or region that can bind to another nucleic acid chain or region in an antiparallel fashion by forming a consecutive string of such base pairs with the other chain or region is termed "complementary."

An "oligonucleotide" refers to a nucleic acid that is shorter than 500, 200, or 100 nucleotides in length. The oligonucleotide may be synthesized chemically, optionally without catalysis by an enzyme. Oligonucleotides may function, for example, as primers, probes, and/or the like.

A "detection reagent" refers to a reagent that facilitates or enables detection of the presence or absence and/or amount of a target with a suitable detector (e.g., an optical detector). A set of detection reagents may be present in a sample-containing fluid and/or in each partition formed from the sample-containing fluid. The set of detection reagents may include at least one binding partner that binds specifically to only one of the targets to be assayed and/or that binds nonspecifically to each of the targets to be assayed. The binding partner may include a label and/or may be luminescent (and/or may have a luminescent form). In embodiments involving target amplification, the set of detection reagents also or alternatively may include one or more amplification primers for each target.

A "reporter" refers to at least one detection reagent or set of detection reagents that reports a condition, such as the presence or absence or the abundance of a target, and/or whether or not a reaction has occurred or the extent of the reaction. Exemplary reporters may comprise at least one luminophore, such as a photoluminophore or a chemiluminophore, and/or at least one oligonucleotide. Other exemplary reporters may include a chromophore, an enzyme, a substrate for an enzyme, a binding partner, or a combination thereof. Exemplary reporters for nucleic acid amplification assays may include a specific reporter, such as a probe, and/or a nonspecific (generic) reporter, such as an intercalating dye (e.g., SYBR Green, ethidium bromide, etc.). Accordingly, the reporter may be a binding partner for a target and/or a product generated from and/or corresponding to the target.

A reporter may have distinct forms and/or conformations. The reporter may have an initial/intact form and one or more degraded/modified forms. The one or more degraded/modified forms may be produced from the initial/intact form during amplification of at least one target. The forms may be distinguishable optically. For example, the degraded/modified form may be more or less photoluminescent than the initial/intact form. An exemplary specific reporter having distinct forms is a Taqman® probe. In other examples, the specific reporter may have distinct conformations such as an intramolecular hairpin configuration, when unbound, and an extended (non-hairpin) configuration, when bound.

A "binding partner" refers to a molecule, complex, assembly, or particle that binds to another entity, such as a target and/or a reaction product (e.g., an amplicon) corresponding to and/or representing a presence/absence or abundance of the target. The binding partner may bind specifically to the entity, and thus may form a specific binding pair with the entity. Non-limiting examples of specific binding pairs include complementary nucleic acids, a receptor and its ligand, biotin and avidin/streptavidin, an antibody and a corresponding antigen, an antibody and protein G, polyhistidine and $Ni^{+2}$, a transcription factor and a nucleic acid containing a binding site for the transcription factor, an aptamer and its partner, and the like. Non-limiting examples of molecules that can specifically interact with or specifically bind to a target molecule include nucleic acids (e.g., oligonucleotides), proteins (e.g., antibodies, transcription factors, zinc finger proteins, non-antibody protein scaffolds, etc.), and aptamers.

"Specific binding" with respect to a binding partner (e.g., a reporter, such as a probe) and a particular target (and/or with respect to a product corresponding to the particular target) in an assay refers to binding between the binding partner and the target (and/or the binding partner and the product) that is substantially exclusive of other targets (and/or their corresponding products) in the assay.

A "label" refers to an identifying and/or distinguishing marker or identifier that is connected to or integral with any entity, such as a compound, an assembly, a biological particle, or droplet, among others. The label may be detectable by any suitable approach, including spectroscopic, photochemical, biochemical, immunochemical, chemical, or other physical methods. Suitable labels may include luminophores, chromophores, radioisotopes (e.g., $^{32}P$, $^{3}H$), electron-dense reagents, enzymes, specific binding partners, or the like. Any method known in the art for conjugating, e.g., for conjugating a probe to a label, can be employed, e.g., using methods described in Hermanson, *Bioconjugate Techniques* 1996, Academic Press, Inc., San Diego. Further aspects of labels that may be suitable are described elsewhere herein, such as in Section IV.

A molecule or other entity that is "attached" to a label (e.g., as for a labeled probe as described herein) is one that is attached covalently ("conjugated") to the label by one or more chemical bonds, or attached noncovalently to the label, such as through one or more ionic, van der Waals, electrostatic, and/or hydrogen bonds such that the presence of molecule can be detected by detecting the presence of the label.

"Luminescence" refers to emission of light that cannot be attributed merely to the temperature of the emitting body. Exemplary forms of luminescence include photoluminescence, chemiluminescence, electroluminescence, or the like. A "luminophore" is any atom, moiety, molecule, complex, or assembly capable of luminescence. Photoluminescence is any luminescence produced in response to irradiation with excitation light and includes fluorescence, phosphorescence, etc. Accordingly, a luminophore may be a photoluminophore (such as a fluorophore or a phosphor), a chemiluminophore, or the like.

An "assay," interchangeably termed a "test," refers to a procedure or set of procedures used to characterize a sample. Such characterization may be obtained via data about the sample obtained from the procedure(s). An assay may be performed using at least one "assay mixture" which is a composition from which one or more signals are detected, before, during, and/or after processing of the composition to permit a reaction, if any, to occur. An assay may determine a property of one or more targets in a sample. A "multiplexed assay" refers to an assay for two or more targets performed on the same set of partitions, generally simultaneously.

A "level" refers to a quantitative or qualitative, and/or relative or absolute measure of abundance for a target. The level may be a presence or absence, as defined by a threshold value, a quantity, or a concentration, among others. The measure may be intrinsic or extrinsic. Exemplary levels include absent, present, a number of partitions containing at least one copy of the target, or a concentration of the target (such as an average target copy number per partition, a target copy number per unit volume, a molarity or mass of the target per unit volume, or the like), among others.

"Amplification" refers to a reaction(s) or process(es) in which copies of a target, such as a target sequence, are generated. The copies may be exact or inexact copies of the target. (Exemplary inexact copies are DNA copies of an RNA target.) Amplification may generate an exponential or linear increase in the number of copies of as amplification proceeds. Exemplary amplification produces at least a 5-, 10-, 100-, or 1000-fold increase in copy number and/or signal. The copies may be generated by any suitable mechanism(s), such as primer extension with a polymerase, a ligase, or a combination thereof. Exemplary amplification reactions for the partition-based assays disclosed herein may include the polymerase chain reaction (PCR) or ligase chain reaction, each of which is driven by thermal cycling. The assays also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification may amplify at least a region (or all) of a template containing a target sequence. The template may be a linear or circular template. Amplification may, for example, form DNA copies of a DNA target sequence, DNA copies of an RNA target sequence, RNA copies of a DNA target sequence, or RNA copies of an RNA target sequence, among others.

Amplification may be performed with any suitable reagents. Amplification may be performed, or tested for its occurrence, in an amplification mixture, which is any composition capable of generating multiple copies of a target sequence, if present, in the composition. An amplification mixture may include any combination of at least one primer or primer pair, at least one amplification reporter, at least one replication enzyme (e.g., at least one polymerase, such as at least one DNA and/or RNA polymerase), and deoxynucleotide (and/or nucleotide) triphosphates (dNTPs and/or NTPs), among others. Further aspects of assay mixtures and detection strategies that enable multiplexed amplification and detection of two or more target sequences in the same partition are described elsewhere herein and in the patent documents listed above under Cross-References, which are incorporated herein by reference.

An "amplicon" refers to a product of an amplification reaction. An amplicon may be single-stranded or double-stranded, or a combination thereof. An amplicon may correspond to at least a region a target sequence that is amplified to generate the amplicon.

A "primer" refers to a nucleic acid, such as an oligonucleotide, capable of, and/or used for, priming replication of a target sequence. Thus, a primer may be a shorter nucleic acid that is complementary to a region of a longer target sequence. During replication, the primer may be extended, based on the target sequence, to produce a longer nucleic acid that is a complementary copy of at least a region of the target sequence. Primer extension may occur incrementally by successive addition of single nucleotides (such as with a polymerase), or may occur by simultaneous addition of a block of two or more nucleotides (such as with a ligase), or a combination thereof, among others. A primer may be DNA, RNA, an analog thereof (i.e., a nucleic acid analog), or any combination thereof. A primer may have any suitable length, such as at least about 7, 10, 15, 20, or 30 nucleotides, among others. Exemplary primers are synthesized chemically, without enzyme catalysis. Primers may be supplied as at least one pair of primers for amplification of at least one target sequence. A pair of primers may be a sense primer and an antisense primer that collectively define the ends (and thus the length) of a resulting amplicon.

A "probe" refers to a binding partner attached to at least one label, such as at least one luminophore or chromophore. A probe may include an oligonucleotide and may be a sequence-specific binding partner for a target sequence and/or an amplicon produced by amplification of the target sequence. The probe may, for example, be designed to enable detection of target amplification based on photoluminescence, such as by fluorescence resonance energy transfer (FRET). An exemplary probe for the nucleic acid assays disclosed herein includes one or more nucleic acids each connected to a single luminophore or each connected to a pair of luminophores that collectively exhibit fluorescence resonance energy transfer (FRET) when proximate one another. The pair of luminophores may provide first and second emitters, or an emitter and a quencher, among others. Fluorescence emission from the pair of luminophores changes when the luminophores are separated from one another, such as by cleavage of the probe during primer extension (e.g., a 5' nuclease assay, such as with a Taqman® probe), or when the probe hybridizes to an amplicon (e.g., a molecular beacon probe). The nucleic acid portion of the probe may have any suitable structure or origin, for example, the portion may be a locked nucleic acid, a peptide nucleic acid, a member of a universal probe library, or the like. In other cases, a probe and one of the primers of a primer pair may be combined in the same molecule (e.g., Amplifluor® primers or Scorpion® primers). As an example, the primer-probe molecule may include a primer sequence at its 3' end and a molecular beacon-style probe at its 5' end. With this arrangement, related primer-probe molecules labeled with different luminophores can be used in a multiplexed assay with the same reverse primer to quantify target sequences differing by a single nucleotide (single nucleotide polymorphisms (SNPs)). Another exemplary probe for nucleic acid assays is a Plexor® primer.

A "transcript" refers to an RNA produced by the process of transcribing DNA, generally with an RNA polymerase. The transcript may provide a target sequence, may represent only a region of the transcribed DNA, such as a gene within the DNA, and may be described as a gene transcript. The transcript may be a primary transcript or a processed transcript produced from a primary transcript (e.g., a spliced transcript). Exemplary transcripts include pre-mRNA (pre-messenger RNA), mRNA, ribosomal RNA (rRNA), transfer RNA (tRNA), pre-micro RNA (pre-miRNA), micro RNA (miRNA), or the like.

"Reverse transcription" refers to formation of a complementary DNA from an RNA template, such as any suitable transcript. Reverse transcription may be performed with an enzyme that catalyzes the process. Exemplary enzymes that may be suitable include a reverse transcriptase (e.g., MLV-RT, Tth Polymerase, AMV-RT, HIV-RT, etc.). The enzyme may also be capable of synthesizing DNA with DNA as a template, and, in some cases, may be capable of amplifying a target sequence. The enzyme may be sufficiently heat stable to permit heating partitions to open the partitions, without destroying the reverse transcriptase activity of the enzyme.

An "allele" refers to one of the alternate forms of a genetic region, such as a gene. Different alleles of the same genetic region/gene may differ from each other by a deletion, an insertion, a duplication, a rearrangement, or a substitution of one or more nucleotides. In exemplary embodiments, the alleles differ by a single nucleotide, and thus the genetic region contains a single-nucleotide polymorphism (SNP). The alleles may or may not result in distinguishable phenotypes. A pair of alleles may, in some cases, be a normal allele (also termed a wild-type allele) and a variant allele (also termed a mutant allele.

At least a pair of targets in the sample (or potentially in the sample) may represent different forms/alleles of a genetic region or gene of interest, such as a variant form/allele (also called a mutant form) and a normal form (also called a wild-type form). The different forms may be alternate forms of the genetic region/gene of interest that differ in sequence at one or more nucleotide positions, such as differing by a single nucleotide, or two, three, or more nucleotides, and/or differing by an insertion, duplication, or deletion, among others. The variant form/allele may be a comparatively rare form of the gene and the normal form/allele may be a comparatively abundant form of the gene for a species of organism (and/or a type of cell) contained by the sample. For example, the variant form may be predominant in fewer than about 10%, 5%, or 1%, among others, of members of a population of interest from the species of organism or cells of the type of cell. Also or alternatively, the normal form may be predominant in greater than about 10%, 25%, or 50% (a majority) of members of the population of interest from the species of organism or cells of the type of cell.

The at least a pair of targets may include a target that is a variant sequence (from a variant form of the gene of interest) and an other target that is a normal sequence (from a normal form of the gene of interest). The variant sequence and the normal sequence may overlap each other in the gene of interest to define a region of overlap. The variant sequence and the normal sequence may differ from each other by at least one nucleotide in the region of overlap. In some cases, the region of overlap may differ by at least, or no more than 1, 2, or 3 nucleotides between the variant sequence and the normal sequence. The region of overlap may be at least 1, 2, 5, or 10 nucleotides, among others. In some examples, the region of overlap may be the same length as the variant sequence and/or the normal sequence.

A "genome-equivalent" refers to an amount of genomic DNA equal in mass to a single genome of a biological particle or organism. (A diploid cell contains genomic DNA for two genomes and most bacterial cells contain genomic DNA for only one genome.) A genome-equivalent can be a useful unit when genomic DNA is isolated from a set of cells or virions, because the genomic DNA from individual cells/virions is mixed and often fragmented. A genome-equivalent of isolated genomic DNA from a single type of cell may have an average of one copy of each gene of the cell's genome. In some cases, a genome-equivalent may be provided by an intact genome inside a cell or other biological particle.

"Opening" biological particles refers to any suitable process(es) and/or manipulation(s) that combines contents of the biological particles with fluid/reagents outside the particles. A step of opening may release a least a portion of the contents from the particles and/or permit entry of reagents into the particles. Opening may perforate, disrupt, rupture, degrade, and/or dissolve, among others, at least one structure of the particles, such as at least one wall, membrane, coat, and/or shell of the particles at or near the periphery of the particles. Opening may be performed by any suitable treatment, such as enzyme digestion (e.g., with an enzyme (such as lysozyme) that degrades carbohydrate), osmotic disruption, heat (e.g., to or at a temperature of at least about 50, 60, 70, 80, or 90 degrees Celsius), or a combination thereof, among others.

An "optical channel" refers to a particular detection regime with which light is detected from partitions. The detection regime may be characterized by a light source, a wavelength regime for irradiating the partitions with light from the light source, a wavelength regime for detection of light from the partitions, an optical path, at least one time interval of irradiation/detection, or any combination thereof, among others. A "wavelength regime" is defined by one or more wavelengths and/or one or more wavebands of light. Optical channels that are different have one or more different characteristics of their detection regimes. The optical channels may use different light sources, different wavelength regimes for irradiating each partition, different wavelength regimes for detection of light from each partition (e.g., different emission filters for the same sensor and/or different sensors with different spectral sensitivities), different optical paths, different time intervals for detecting light from each partition, or any combination thereof. Each optical channel may or may not include a light source. The optical paths, if different, may travel through different optical elements, such as different spectral filters. The optical paths may be non-overlapping or at least partially overlapping. If overlapping, the optical paths may overlap between a light source and each detected partition, and/or between each detected partition and one or more light sensors.

Selected terms defined above are described further in the following sections.

II. System Overview

This section provides an overview of exemplary methods and apparatus for performing digital assays with associated targets.

FIG. 1 shows a flowchart of an exemplary method 50 of performing a multiplexed digital assay of associated targets. The steps presented for method 50 may be performed in any suitable order and in any suitable combination. Furthermore, the steps may be combined with and/or modified by any other suitable steps, aspects, and/or features of the present disclosure.

A. Sample Preparation

A sample may be prepared for the assay, indicated at 52. Preparation of the sample may include any suitable manipulation of the sample, such as collection, dilution, concentration, purification, lyophilization, freezing, extraction, restriction-enzyme digestion, shearing, combination with one or more assay reagents, performance of at least one preliminary reaction, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents to produce a sample-containing mixture for performing a reaction (such as an amplification reaction) for each target and for reporting an extent of each reaction (e.g., whether or not the reaction occurred above a threshold level or within a range). Reagents for amplification may include any combination of primers for targets, dNTPs and/or NTPs, at least one enzyme (e.g., a polymerase, a ligase, a reverse transcriptase, a restriction enzyme, or a combination thereof, among others, each of which may or may not be heat-stable), and/or the like. Accordingly, the mixture may have a complete set of reagents for (i.e., may be competent for) amplification of each target under suitable environmental conditions (e.g., incubation at an elevated temperature or modulation of temperature (such as by thermocycling)). The mixture may be capable of amplification of each of one or more targets, if present, in the sample (or a partition thereof). Preparation of the mixture may render the sample capable of reporting, or being analyzed for, whether or not a reaction, such as amplification, has occurred, on a target-by-target basis, and optionally the extent of any such reaction. The mixture may include one or more reporters that are collectively sensitive to amplification of each target. The reporters each may include a labeled probe that includes an oligonucleotide labeled with a luminophore (e.g., a photoluminescent moiety), such as a fluorophore. Alternatively, or in addition, at least one generic reporter may be utilized. In some cases, the same generic reporter may report amplification of each target.

In some embodiments, the sample may comprise one or more types of biological particles and or nucleic acid therefrom. The biological particles collectively may provide each of the targets. The biological particles may be opened at any suitable time.

B. Partition Formation

Portions of the sample may be disposed in partitions, to form partitions for assay of two or more associated targets, indicated at 54. In some embodiments, the associated targets may be amplified from the same template, such as from at least one copy of the template in a partition. Copies of the template may be present in the partitions at partial occupancy. In some embodiments, each of a plurality of types of biological particles may be present in the partitions at partial occupancy, namely, with only a subset of the partitions containing each type of particle. Alternatively, or in addition, each of a plurality of targets contained and/or provided by the biological particles may be present in the partitions at partial occupancy.

The partitions may be formed by any suitable procedure, in any suitable manner, and with any suitable properties. For example, the partitions may be formed with a fluid dispenser, such as a pipette, with at least one droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

Partitions competent for amplification of each target may be formed directly from a bulk phase containing the targets, or may be formed in multiple steps. In some cases, the step of forming partitions may include dividing a bulk phase into isolated fluid volumes (such as droplets) containing the targets/template at partial occupancy. The fluid volumes may be the partitions themselves or may contribute to the partitions. For example, the fluid volumes may be a first set of fluid volumes, and the step of forming partitions may include combining individual fluid volumes of the first set with individual fluid volumes of a second set. The second set may include one or more reagents for amplification of one or more of the targets, such as at least one primer for amplification of at least one of the targets, primers for a pair of targets, or the like. The step of combining may include fusing fluid volumes of the first set individually with fluid volumes of the second set, such as fusing droplets containing the targets with droplets containing primers for amplification of the targets.

The partitions may be configured to perform at least a pair of target assays for associated targets, such as linked targets. The linked targets may represent any suitable connected and/or overlapping pair of regions of the template. The regions may be spaced from each other along the template, such as separated by at least 50, 100, 200, or 400 nucleotides/base pairs, among others. In some cases, the regions may be separated by a number of nucleotides greater than the length of each region. A greater separation of the regions may be desirable in some cases to reduce co-amplification of both targets in the same amplicon with a primer for each target (e.g., with convergent outer primers for a pair of the targets). In other cases, the regions may overlap one another by any suitable number of nucleotides, such as less than twenty, less than ten, or the like. In some embodiments, the regions may overlap at a site of allelic variation. Alternatively, or in addition, each region may be strand-specific, with one of the regions representing one strand of the template and the other region representing the other strand of the template. The strand-specific regions may or may not overlap each other along the template. Further aspects of partition formation are described in Sections I and III-V.

C. Performance of Reaction(s)

At least one type of reaction may be performed in the partitions, indicated at 56. For example, the targets may be amplified in the partitions. Amplification of each target may occur selectively (and/or substantially) in only a subset of the partitions, such as less than about three-fourths, one-half, one-fourth, or one-tenth of the partitions, among others. Amplification of each target may occur selectively in partitions containing at least one copy of the target (e.g., containing at least one copy of a template including the target).

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

D. Data Collection

Data may be collected from a plurality of partitions, with the data indicating a presence or absence of each of the targets in individual partitions, indicated at 58. For example, amplification data may be collected. The data may be collected by detecting light from individual partitions. The light may (or may not) be emitted in response to irradiation of the partitions with excitation light. The data may be collected in any suitable number of optical channels, such as only one, only two, or more than two among others. The data may be collected in the same number of optical channels and target or in fewer optical channels than targets, among others.

Data collection may include generating one or more signals representative of light detected from individual partitions. The signals may represent an aspect of light, such as the intensity, lifetime, polarization, and/or energy transfer of the light. The signals optionally may include data collected in two or more different optical channels (e.g., in different wavelength ranges (wavebands) and/or color regimes) from reporters for the same and/or different targets). The light detected from each reporter may be light emitted from a luminophore (e.g., a fluorophore). The light detected in a given channel may be detected such that light from different reporters is summed or accumulated without attribution to a particular reporter. Thus, the signals for a given channel may represent two, three, four, or more assays and thus two, three, four, or more targets. In other cases, the signals for two or more of the targets each may be detected in a different optical channel.

The signal(s) may be created based on light detected from one or more reporters in the partitions. The one or more reporters may report whether at least one of two or more particular amplification reactions represented by the signal has occurred in a partition and thus whether at least one copy of at least one of two or more particular targets corresponding to the two or more particular amplification reactions is present in the partition. The level (interchangeably termed the amplitude) of the signal corresponding to the reporters may be analyzed to determine whether or not at least one of the particular amplification reactions has occurred and at least one copy of one of the particular targets is present. The level of the signal may vary among the partitions according to whether at least one of the particular amplification reactions occurred or did not occur and at least one of the particular targets is present or absent in each partition. For example, a partition indicated in the data as positive for a particular target may have a signal value that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Data may be collected from a plurality of the partitions (i.e., only a subset or all of the partitions) under any suitable conditions. All of the data may be collected at about the same temperature from the plurality of partitions. Alternatively or in addition, all of the data may be collected at a temperature that is below a melting temperature of each amplicon, below an annealing temperature used in thermocycling for amplification, and/or below about 50 or 45 degrees Celsius, among others. The amplification data may be collected after an endpoint of amplification has been reached for each target.

The reporters may have any suitable structure and characteristics. Each reporter may be a probe including an oligonucleotide and a luminophore associated with the oligonucleotide (e.g., with the luminophore conjugated to the oligonucleotide), to label the oligonucleotide. The probe also may or may not include an energy transfer partner for the luminophore, such as a quencher or another luminophore. The probe may be capable of binding specifically to an amplicon produced by amplification of a target for the probe. The probe may or may not also function as an amplification primer in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

In some cases, at least one of the reporters may be a generic reporter, such as a photoluminescent or chromogenic dye, that binds nucleic acid relatively nonspecifically. For example, the dye may not be conjugated to an oligonucleotide that confers substantial sequence binding specificity. The dye may be a major groove binder, a minor groove binder, an intercalator, or an external binder, among others. The dye may bind preferentially to double-stranded relative to single-stranded nucleic acid and/or may exhibit a greater change in a photoluminescent characteristic (e.g., intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others. A generic reporter may be used to perform a multiplexed assay of any of the targets disclosed herein. Further aspects of multiplexed assays with a generic/nonspecific reporter as described elsewhere herein and in the references identified above under Cross-References, which are incorporated herein by reference, particularly U.S. patent application Ser. No. 14/191,295, filed Feb. 26, 2014.

E. Partition Classification

Partitions may be classified as positive or negative for each of the targets, indicated at 60. For example, partition populations (interchangeably termed clusters) that test negative for both targets, positive for only one of the targets (single positives), and positive for two or more of the targets (double positives, etc.) may be identified from the data. Identification may be performed by a data processor using an algorithm (e.g., an algorithm that identifies patterns (e.g., partition clusters) in the data), by a user, or a combination thereof. In some cases, a data processor may produce and output (e.g., display) a graph of the collected data (e.g., a 2-D scatter plot or histogram (see Sections III and IV)). The user then may define the boundary of each population based on the plot(s), e.g., through a graphical user interface to define population boundaries, and/or by inputting values (e.g., representing amplitude thresholds/ranges) to define a boundary for each population. Each population boundary may be defined by one or more ranges of values, a geometrical shape (e.g., a polygon, ellipse, etc.) that surrounds the population, or the like.

Classification of partition populations may include assigning each partition to one of a plurality of predefined bins each corresponding to a distinct partition population. The predefined bins may represent all possible combinations of negatives and positives for the targets.

F. Obtaining Partition Counts

A partition count for each partition population may be obtained. The partition count may be a value for the number of partitions constituting a particular partition population or set of two or more partition populations. Accordingly, a partition count may, for example, be determined by counting data points (partitions) of a population or cluster, summing partition counts from different populations/clusters, subtracting a calculated/expected partition count from an actual partition count, or a combination thereof, among others.

G. Determination of Target Levels

A level of at least one target may be determined based on the classified partitions, and, optionally, on a known, expected, or assumed degree of associated of the targets to each other, indicated at 62. With associated targets, the levels of the targets may be about the same, in which case only one target level can represent the levels of both targets. Determination of target levels may (or may not) be based on each target having a Poisson distribution among the partitions. Each level may, for example, be a value representing the total number of partitions positive for the target, or a concentration value, such as a value representing the average number of copies of the target per partition or unit volume, among others. The partition data further may be used (e.g., directly and/or as concentration data) to estimate copy number (CN) and copy number variation (CNV), or any other property of the sample, using any suitable algorithms.

A level (e.g., a concentration) of each target may be determined with Poisson statistics. The concentration may be expressed with respect to the partitions or a unit volume, and/or with respect to a sample providing the target, among others. The concentration of the target in the partitions may be calculated from the fraction of partitions that are positive for the target (or, equivalently, the fraction of partitions that are negative for the target) by assuming that copies of the target (before amplification) have a Poisson distribution among the partitions. With this assumption, the fraction f(k) of partitions having k copies of the target is given by the following equation:

$$f(k) = \frac{C^k}{k!} e^{-C} \qquad (1)$$

Here, C is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$C = -\ln\left(1 - \frac{N_+}{N_{tot}}\right) \qquad (2)$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_++N_-)$) is equal to $f_+$, which is the fraction of partitions positive for the target (i.e., $f_+=f(1)+f(2)+f(3)+\ldots$) (see Equation 1), and which is a measured estimate of the probability of a partition having at least one copy of the template.

Another exemplary Poisson equation that may be used is as follows:

$$C = -\ln\left(\frac{N_-}{N_{tot}}\right) \qquad (3)$$

where $N_-$ and $N_{tot}$ are as defined above. $N_-/N_{tot}$ is equal to $f_-$, which is the fraction of negative partitions (or $1-f_+$), is a measured estimate of the probability of a partition having no copies of the target, and C is the target concentration as described above.

Equations 2 and 3 above can be rearranged to produce the following:

$$C = \ln(N_{tot}) - \ln(N_{tot} - N_+) \qquad (4)$$

$$C = \ln(N_{tot}) - \ln(N_-) \qquad (5)$$

The concentration of each target in a multiplexed assay can, for example, be determined with any of Equations 2 to 5, using values (i.e., partition counts) obtained for $N_{tot}$ and $N_-$ or $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

The value used for $N_-$ or $N_+$ is generally different for each target, and may result from summing the counts from a plurality of partition populations each containing a different combination of the targets being tested in the multiplexed assay. For example, with three targets (A, B, and C) in a multiplexed assay, the number of partitions positive for target A, $N_{+A}$, may be calculated as the sum of counts from the single (A only), double (AB and AC), and triple (ABC) positive populations, for use in Equation 2 or 4. Equivalently, the number of partitions negative for target A, $N_{-A}$, may be calculated, for use in Equation 3 or 5, as the difference between $N_{tot}$ and $N_{+A}$. Alternatively, the number of partitions negative for A may be calculated as the sum of counts from each population that is negative for target A, namely, in this example, a triple negative ("empty") population, two single positive populations (B and C), and one double positive population (BC). The same process may be repeated for each of the other targets using partition counts from the appropriate subset of populations.

In some embodiments, an estimate of a level (e.g., concentration) of a target (and/or a corresponding template or biological particle) may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because Poisson statistics takes into account the occurrence of multiple copies of the same target in the same partitions.

The following are non-limiting examples of how the concentration of a pair of linked targets may be determined. Additional terms may be utilized in some instances.

The concentration of a pair of linked targets, A and B, may be determined based on a count of double positives (AB) and a total partition count using a modified form of Equation 5 above. For example, the concentration of target A and/or target B, assuming 100% linkage, can be calculated as follows:

$$C_{A/B} = \ln(N_{tot}) - \ln(N_A + N_B + N_0) \qquad (6)$$

where $N_A$ is the number of partitions testing positive for A only, $N_B$ is the number of partitions testing positive for B only, and $N_0$ is the number of partitions testing negative for both targets. In this case, each single positive (A or B) is deemed to be a false positive.

The concentration obtained from Equation 6 above can be corrected/adjusted to account for incomplete linkage by dividing by the degree of linkage (expressed as a fraction):

$$C_{A/B}\text{corr} = C_{A/B}/\text{linkage} \qquad (7)$$

For example, if the degree of linkage is 80%, the concentration calculated from Equation 6 would be adjusted upward by dividing by 0.80 to account for unlinked copies of the targets that did not co-localize to the same partitions.

The target level determination also may include a calculation of the number of expected double positives, for example, if the rate of false single positives is high. If each single-positive partition is assumed to be a false positive, the number of false double positives can be calculated as follows:

$$N_{AB\ False} = \frac{N_A N_B}{N_0} \quad (8)$$

where $N_A$, $N_B$, and $N_0$ are as defined above for Equation 6. The calculated number of false double positives can be compared to the number of the observed double positives to determine whether the targets (and/or template) are present at a level significantly above background. Also, the calculated number of (false) double positives can be subtracted from the observed number of double positives to obtain a count for the true double positives. The count obtained then can be utilized in Equation 6 and/or 7 to determine the concentration of the targets.

In the case of allele-specific primers, where the outer primers may give a distinct signal, such as a weak signal in both channels, on the wild-type template, a fifth population of partitions may be generated. The fifth population may be treated as a second $N_0$ population, which may be combined with the other $N_0$ population in any of the equations presented above.

FIG. 2 shows an exemplary system 80 for performing the digital assay of FIG. 1. System 80 may include a partitioning assembly, such as a droplet generator 82 ("DG"), a thermal incubation assembly, such as a thermocycler 84 ("TC"), a detection assembly (a detector) 86 ("DET"), and a data processing assembly (a data processor) 88 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets), or signals/data, between the assemblies. Any suitable combination of the assemblies may be operatively connected to one another, and/or one or more of the assemblies may be unconnected to the other assemblies, such that, for example, material/data are transferred manually.

Detector 86 may provide a plurality of optical channels in which data can be collected. The detector may (or may not) have a distinct sensor or detection unit for each optical channel.

System 80 may operate as follows. Droplet generator 82 may form droplets disposed in a continuous phase. The droplets may be cycled thermally with thermocycler 84 to promote amplification of targets in the droplets. Signals may be detected from the droplets with detector 86. The signals may be processed by processor 88 to determine droplet counts and/or target levels, among others. The system also may include a program, optionally residing on a computer-readable storage medium, for controlling any suitable aspects of a method of performing an assay. For example, the program may comprise instructions for causing the droplet generator to form droplets, the thermocycler to promote target amplification, the detector to collect data, the processor to process the collected data, or any combination thereof, among others.

Further aspects of sample preparation, assay design, partition formation, data collection, population identification, partition classification, obtaining partition counts, and target level determination, among others, that may be suitable for the system of the present disclosure are described elsewhere in the present disclosure, such as below in Sections III-V, and in the references identified above in the Cross-References, which are incorporated herein by reference.

III. Exemplary Digital Assays With Associated Targets

This section presents selected aspects and embodiments of the present disclosure related to methods of performing multiplexed digital assays with increased sensitivity, such as a lower limit of detection and/or an ability to distinguish a single-stranded template from a double-stranded template. The assays may be performed with linked targets that are connected to each other, and/or with associated/linked targets that are contained by the same biological particles.

A. Improved Limit of Detection with a Multiplexed Assay

This example compares the limit of detection for a singleplex assay of one target (target A) and a multiplexed assay of two linked targets (targets A and B); see FIGS. 3, 3A, 4, and 4A.

FIG. 3 shows a schematic diagram illustrating an exemplary, less-sensitive singleplex digital assay performed in partitions on only one target 100 (target A). At least one bulk phase 102 may be divided into fluid volumes that directly (or in combination with other fluid volumes from one or more other bulk phases) form partitions 104, such as droplets 106. Bulk phase 102 contains copies of a template 108 (e.g., a nucleic acid template) present at partial occupancy in partitions 104. Accordingly, a subset of the partitions (such as the "true positive" droplet shown) contains at least one copy of the template, while the rest of the partitions contain no copies of the template (such as the "negative" droplet and the "false positive" droplet shown).

Template 108 may be double-stranded, as shown here, or single-stranded, among others. The presence of, or the potential for, base pairs, but generally not the actual number of base pairs, is illustrated schematically in FIG. 3 and elsewhere in the drawings by line segments that span complementary strands of a nucleic acid duplex.

The strategy for amplification of target 100 from template 108 is presented in bulk phase 102, even though this process generally occurs predominantly or exclusively after formation of partitions 104. Accordingly, amplification and products thereof are illustrated in bulk phase 102 in broken lines. This convention for illustrating amplification and changes in reporter configuration in the bulk phase also has been used in other drawings of the present disclosure to illustrate the various multiplexed assays disclosed herein.

Target 100 is amplified from template 108 to generate copies of an amplicon 110 (interchangeably termed an amplified target). The size of amplicon 110 may be defined by at least one primer used for amplification. For example, here, a pair of primers for target 100, namely, a forward primer ($F_A$) and a reverse primer ($R_A$), determine the region of template 108 that is amplified, to define the endpoints of the target and amplicon 110. Amplification of target 100 may be detectable with a reporter 112.

FIG. 3A shows reporter 112 alone. The reporter may be structured as a probe 114 (e.g., a Taqman® probe, $P_A$) that binds specifically to the target and/or amplicon. Here, probe 114 includes an oligonucleotide 116, and a luminophore (e.g., a fluorophore) 118 and a quencher 120 attached to the oligonucleotide. The oligonucleotide may provide target specificity by hybridization predominantly or at least substantially exclusively to only one target. Each of the fluorophore and the quencher may (or may not) be conjugated to the oligonucleotide by a covalent bond. The probe also or alternatively may include a binding moiety (a minor groove binder) for the minor groove of a DNA duplex, which may be conjugated to the oligonucleotide and which may function to permit a shorter oligonucleotide to be used in the probe. In any event, amplification may modify the reporter, such as by degradation of oligonucleotide 116, to separate fluorophore 118 from quencher 120. The fluorophore then is capable of fluorescing more brightly when irradiated with excitation light (shown as an increase in size of the fluorophore in FIG. 3 and elsewhere in the drawings), because the effect of the quencher on light emission is reduced or eliminated.

Quencher 120 is configured to quench light emission from the fluorophore in a proximity-dependent fashion. Accordingly, light detected from the fluorophore may increase when the associated oligonucleotide binds to the amplified target, to increase the separation between the fluorophore and the quencher, or when the probe is cleaved and the fluorophore and quencher become uncoupled during target amplification, among others. The quencher may be the same or different for each fluorophore. Here, the assay is designed so that the presence of a target leads to an increase in corresponding intensity, because amplification reduces quenching. In other assays, the reverse could be true, such that the presence of a target caused a decrease in corresponding intensity (although it typically is easier to detect a signal against a dark background than the opposite). Moreover, some embodiments may be constructed without a quencher, so long as the fluorescence and/or the signal changes upon amplification.

Each partition may be deemed positive or negative for target 100 (and/or template 108) based on an amplitude of at least one signal detected from the partition. For example, here, the two partitions assigned as positive fluoresce more brightly than the partition assigned as negative. However, partitions that are deemed positive for the target may not actually contain template 108. Such false positives may occur by various mechanisms, such as stochastic variation in the signal produced by probe 114 in the absence of target amplification, non-specific probe cleavage, primer/probe dimers or other off-target amplification, contamination with copies of the amplicon (e.g., amplicon from an earlier experiment), or the like. In any event, since false positives cannot be distinguished easily from true positives in a standard assay, the presence of the false positives provides noise that determines the sensitivity of the assay and the limit of detection for the target. For example, if the false positive frequency is one per one-thousand partitions in a particular assay, the true positive frequency generally should be significantly higher than that for the assay to reliably provide valid results. The false-positive rate can determine the number of positive partitions needed for a statistically significant result, so lowering the false-positive rate can allow a higher confidence level to be obtained from the same number of partitions or the same confidence level to be obtained from fewer partitions.

FIG. 4 shows a schematic diagram illustrating an exemplary, more-sensitive multiplexed digital assay performed generally as in FIG. 3, but with two linked targets 100 (targets A and B). Target A is amplified as in FIG. 3 with a forward primer and a reverse primer, $F_A$ and $R_A$, and is detected with a target A-specific probe, $P_A$. Similarly, target B is amplified from another region of template 108 with a forward primer and a reverse primer, $F_B$ and $R_B$, and is detected with a target B-specific probe, $P_B$. The target-specific probes, $P_A$ and $P_B$, may be spectrally distinct due to distinct fluorophores. $P_A$ includes fluorophore 118, and $P_B$ includes different fluorophore 122. Targets A and B may represent overlapping or nonoverlapping regions of template 108. If nonoverlapping, the target regions may or may not be separated by more than the length of each target region. The target regions (and/or A and B amplicons 110) may (or may not) be about the same size, such as differing by less than about 50% or 25% in length.

The fluorophores attached to the respective oligonucleotides of the probes may be the same or different. The fluorophores may produce signals in different channels or detectable but distinguishable signals in the same channel, allowing multiplexing in that channel. The signals may be distinguishable because an aspect of the fluorescence is different for one fluorophore relative to the other fluorophore(s). For example, the intensity associated with one fluorophore, following reaction, may be lower or higher than the intensity(ies) associated with the other fluorophore(s). In some embodiments, one probe may be labeled with a different number of fluorophores than the other probe, and/or the probes may be located in slightly different local environments, creating a different level of fluorescence for each probe following reaction. Alternatively, or in addition, both probes may be labeled with the same number of fluorophores (e.g., one fluorophore), but there may be more or less of one probe than the other in the sample, so that a greater or smaller signal is created when the reactions have occurred. In some cases, the fluorophores themselves might be different, with one more or less intrinsically fluorescent than the other in a particular channel (e.g., due to differences in extinction coefficient, quantum yield, spectral output, etc.). Exemplary fluorophores that may be suitable include FAM, HEX, VIC, ROX, TAMRA, JOE, etc., among others.

Each of partitions 104 may be classified as positive or negative based on whether or not the partition tests positive for both targets A and B. For example, here, a true positive shown on the left ("true AB") contains at least one copy of template 108 and exhibits light emission from both fluorophores 118, 122 characteristic of target amplification. Partitions testing negative for amplification of either or both targets, indicated at 124, may be deemed negative for template 108 (and both targets). Finally, false double positives may occur, where a number of partitions exhibit a positive signal for both targets A and B without containing template 108. However, such false double positives should occur much less frequently than false single positives in the singleplex assay described above for FIG. 3. As an example, intended only for illustration, if the frequency of false single positives for each target is one per one-hundred partitions in a particular assay configuration, then the frequency of false double positives should be approximately one per ten-thousand partitions, a two-log increase in sensitivity and decrease in the limit of detection relative to a single-target assay.

Outer primers $F_A$ and $R_B$ for the linked targets can, in some cases, function together as another primer pair. The outer primers may amplify a longer region of the template that includes both targets A and B and a connecting sequence that extends from one target to the other. The signals produced by this third amplification reaction in partitions may be distinguishable from signals produced by amplification of target A only, target B only, and targets A and B with their respective primer pairs. For example, the third amplification reaction may produce substantially weaker signals, because amplification of the longer region of the template may be significantly less efficient than amplification of the shorter regions corresponding to each target alone. The third amplification reaction may be undetectable if amplification of either target alone outcompetes the third reaction so effectively that the third reaction is completely masked. The amplitude of any signals produced by amplification with the outer primers may be reduced or rendered undetectable by selecting linked targets that are spaced significantly from each other. For example, the targets can be positioned near the opposing ends of the template, to increase the length of the intervening sequence between the targets. However, in some assay configurations (see below) the targets overlap one another where the inner primers ($R_A$ and $F_B$) bind and thus cannot be spaced from each other along the template, although the locations and/or sequence content of the outer primers, $F_A$ and $R_B$, can be selected such that the longer product produced by amplification with the outer primers is not favored. In any event, signals, if any, generated by amplification with the outer primers can be ignored or may be utilized explicitly in determining whether or not a pair of linked targets is present in individual partitions.

FIG. 4A shows an exemplary scatter plot of fluorescence intensity (fl. int.) data that may be collected from partitions in the multiplexed digital assay of FIG. 4. In the plot, populations or clusters of data points are represented schematically by circles, with relative numbers of data points in the various populations being represented schematically by the relative sizes of the circles. Each data point represents a partition and is positioned in the plot according to signal values that may be collected for the partition in a pair of channels (channels 1 and 2). Here, channel 1 measures fluorescence from fluorophore 118, and channel 2 from fluorophore 122 (see FIG. 4). The populations are identified in the plot as double negative (−), single positive (A or B), and double positive (AB). Targets A and B may, for example, be expected to exhibit about 90% linkage. With this degree of linkage, only a small fraction of the single-positive partitions (indicated schematically in broken lines within the A and B populations) would be true positives, while the rest of the single-positive partitions would be false positives. Also, the single positives, even when derived from an actual template for target A or B, generally represent only partial templates, and not the longer template indicated by simultaneous detection of both targets. Likewise, only a small fraction of the double-positive partitions (indicated by a broken line within the AB population) would be false positives, based on the frequency of false single-positive partitions.

B. Configurations for Multiplexed Assay of Linked Targets

Figure 6:
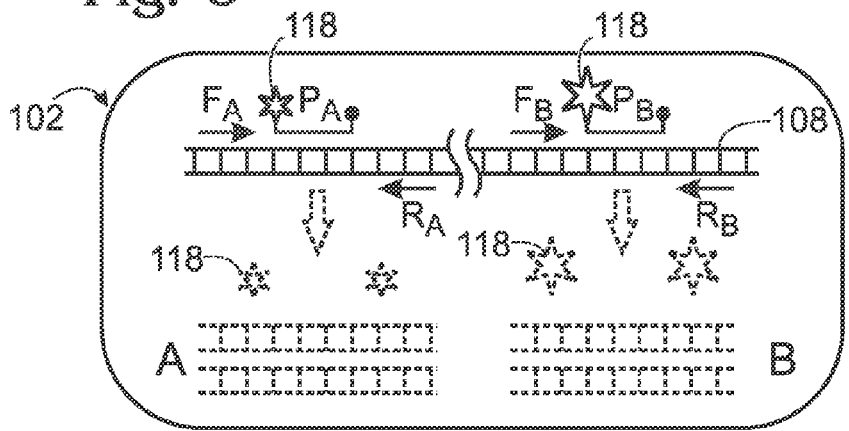
FIG. 6 is a schematic diagram illustrating still another exemplary bulk phase for the multiplexed digital assay of FIG. 4, with the spectrally distinct probes of FIG. 4 replaced with spectrally similar probes at different concentrations and/or labeled with different amounts of the same fluorophore, in accordance with aspects of the present disclosure.
Figure 7:
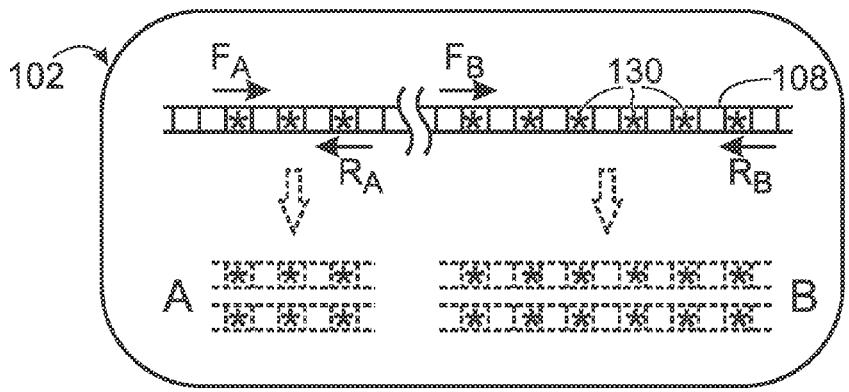
FIG. 7 is a schematic diagram illustrating yet another exemplary bulk phase for the multiplexed digital assay of FIG. 4, with the spectrally distinct probes of FIG. 4 replaced with a generic reporter (e.g., an intercalating dye) to report amplification of both targets, in accordance with aspects of the present disclosure.

This example describes exemplary configurations for multiplexed assay of linked targets (targets A and B); see FIGS. 5-7.

FIG. 5 shows a schematic diagram illustrating another exemplary bulk phase 102 for the multiplexed digital assay of FIG. 4. The assay configuration depicted in FIG. 5 may differ from that of FIG. 4 in at least one of two ways. First, the primers for amplification of target B may be spaced farther apart from each other to generate a B amplicon that is significantly longer than the A amplicon, such as at least 50% longer or at least twice as long. Second, the probe for target B, $P_B$, may not be spectrally distinct from the probe for target A ($P_A$). The same fluorophore 118 may be present in each probe, but light emitted from the (degraded) probe for each target assay can be distinguished according to intensity. For example, here, amplification of target B is shown as being less efficient than amplification of target A, because amplification of a longer template may be less efficient than for a shorter template. The result is production of more copies of the A amplicon than the B amplicon, and more degraded probe A ($P_A$) than probe B ($P_B$).

FIG. 6 shows a schematic diagram illustrating another exemplary bulk phase 102 for the multiplexed digital assay of FIG. 4. The assay configuration depicted in FIG. 6 uses the same fluorophore 118 for both target assays, as in FIG. 5, and distinguishes the two assays based on the intensity of light emitted for each target assay. However, the lengths of amplicons A and B are about the same. A distinguishable intensity for the presence of each target may be generated by labeling the probes for targets A and B with different amounts of fluorophore 118. In the present illustration, probe B contains more of fluorophore 118 than probe A, and yields a stronger signal for the presence of target B than target A. The presence of both targets A and B may produce an even stronger signal. Accordingly, based on the fluorescence intensity measured from a partition, the partition may be classified as (and/or may test as) negative for both targets (lower signal), A-positive only (higher signal), B-positive only (yet higher signal), or positive for both targets A and B (highest signal). In other examples, a distinguishable intensity may be generated for each assay by adjusting at least one primer concentration for an assay, a sequence of at least one primer (e.g., to increase or decrease the melting temperature ($T_m$) of the primer), a probe concentration, or any combination thereof, among others.

The discussion above assumes equal cleavage rates for a given number of extension events, but the melting temperature ($T_m$) of the probe (bound to product) may cause that to differ. Distinguishable intensities may result by having a higher $T_m$ for one of the probes so the probability of cleavage with each extension step is higher. Alternatively, if the $T_m$ is lower, then less of the probe would be cleaved. Accordingly, different signal intensities may be produced and/or signal intensities may be adjusted by selecting probes having distinct melting temperatures.

FIG. 7 shows a schematic diagram illustrating yet another exemplary bulk phase 102 for the multiplexed digital assay of FIG. 4. In the assay configuration depicted here, the sequence-specific probes of FIG. 4 have been replaced with a generic reporter 130 (e.g., an intercalating dye) to report amplification of both targets. The two assays may be distinguishable according to a different intensity of fluorescence produced by reporter 130 bound to amplicons A and B. The generic reporter may generate a fluorescence emission for a partition that is proportional to the mass or total length of amplicon in the partition. In the present illustration, the same number of copies of each amplicon is generated by amplification of each target, but the B amplicon is longer than the A amplicon, which results in a stronger signal for B-positive partitions relative to A-positive partitions. In other cases, a longer amplicon may result in a weaker signal than for a shorter amplicon if the increase in length results in a disproportionate reduction in amplification efficiency.

C. Allele-Specific Multiplexed Assays

Figure 8:
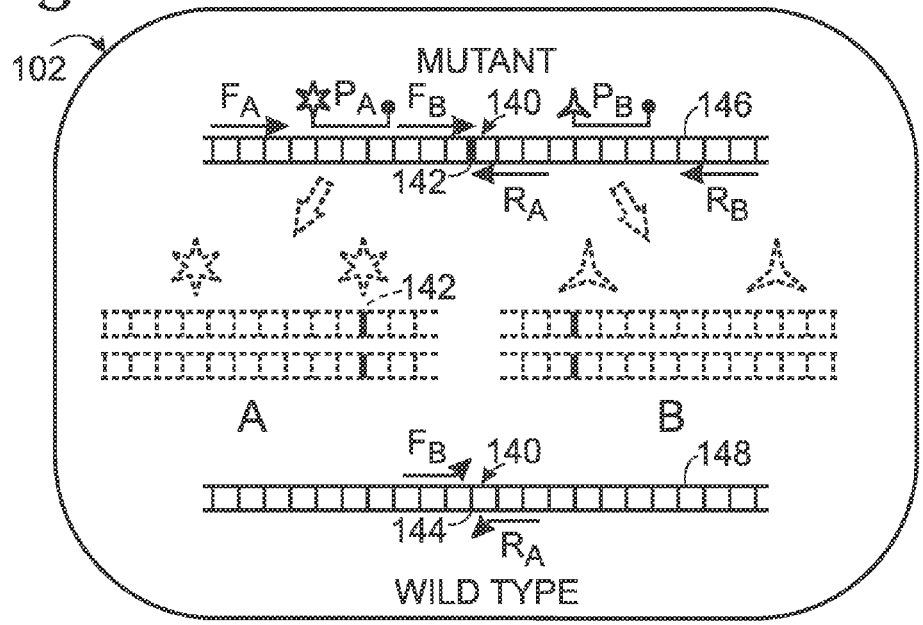
FIG. 8 is a schematic diagram illustrating still another exemplary bulk phase for the multiplexed digital assay of FIG. 4, with the two targets (and primers therefor) overlapping at a site of allelic variation such that each target assay (A or B) is allele-specific and selectively detects a mutant target relative to a wild-type target, in accordance with aspects of the present disclosure.
Figure 9:
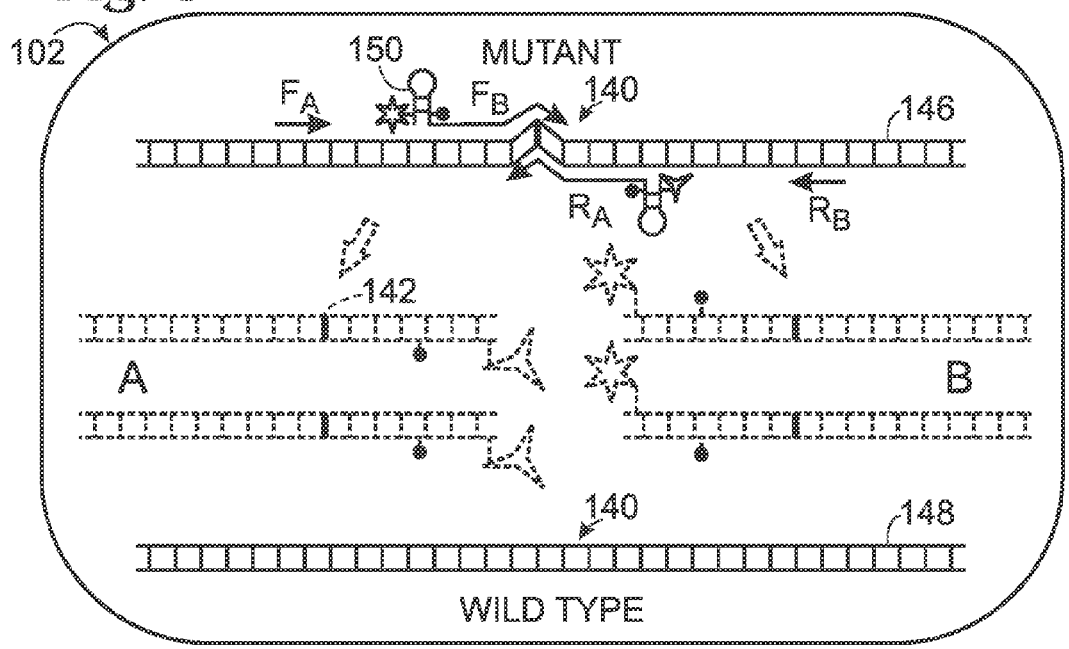
FIG. 9 is a schematic diagram illustrating another exemplary bulk phase for performing a pair of allele-specific assays as in FIG. 8, with the probes and allele-specific primers of FIG. 8 replaced with labeled allele-specific primers that also function as amplification reporters, in accordance with aspects of the present disclosure.

This example describes exemplary configurations for multiplexed assay of an allele based on amplification of targets that overlap at the allele; see FIGS. 8-10.

FIG. 8 is a schematic diagram illustrating another exemplary bulk phase 102 for the multiplexed digital assay of FIG. 4. In the configuration depicted, targets A and B overlap at a site 140 of allelic variation, with at least two distinct allele sequences 142, 144 present at site 140 in the sample and/or more generally in the population from which the sample was obtained. Exemplary allele sequences contain and/or may be distinguished from each other by a single nucleotide polymorphism, a multiple nucleotide polymorphism, a deletion, an insertion, a rearrangement, or the like. In any event, each target assay (for A and B) may be specific for the same allele, such as specifically detecting a mutant template 146 (or a first allele) having allele sequence 142, and not a wild-type template 148 (or a second allele) having allele sequence 144. More particularly, forward B primer ($F_B$) and reverse A primer ($R_A$) do not prime amplification on wild-type template 148 due to the nucleotide sequence difference(s) at the site of allelic variation.

FIG. 9 is a schematic diagram illustrating another exemplary bulk phase for performing a pair of allele-specific assays as in FIG. 8. Here, the probes and allele-specific primers of FIG. 8 are replaced with labeled allele-specific primers ($F_B$ and $R_A$) that also function as amplification reporters. The labeled primers each may have a hairpin structure 150 that positions a quencher close to the associated fluorophore, to quench emission from the fluorophore. The hairpin structure may be eliminated when the primer is incorporated into a double-stranded amplicon, resulting in increased fluorescence.

FIG. 10 illustrates exemplary labeled, allele-specific primers $R_A$ and $F_B$ for the allele-specific assays of FIG. 9. The primers are shown paired with sense and antisense strands 152, 154 of mutant template 146, sense and antisense strands 156, 158 of wild-type template 148, and with each other. Individual base pairs (actual or potential) are shown as vertical bars, with mismatches indicated by the letter X.

In the depicted embodiment, central or inner primers $R_A$ and $F_B$ do not end on a nucleotide of allelic variation, but instead have a high degree of overlap with each other, and use deliberate mismatches to destabilize the primers. The primers can be chosen to each have a few mismatches (e.g., two) to the target sequence (e.g., mutant strands 152, 154), but an additional mismatch (or more) to closely related templates (e.g., wild-type strands 156, 158), assuming there is a single-nucleotide polymorphism differentiating the two targets. Thus, although the primers are partially destabilized on the mutant sequence, they are much more destabilized on the wild-type sequence leading to better discrimination between mutant and wild type. The overlapping primers $R_A$ and $F_B$ can simultaneously bind to both strands of a single copy of mutant template 146 in a partition. Also, if properly chosen, the deliberate mismatches can lead to not only greater stability on the mutant sequence than the wild-type sequence (or vice versa), but also high destabilization of a potential primer dimer formed by the overlapping primers (shown at the bottom of FIG. 10). For example, if the primers each have two mismatches to the mutant template and three mismatches to the wild-type template, they may have four mismatches with one another, as shown here. In this way, the potential primer dimer is highly destabilized and thus does not disrupt the multiplexed assay.

The allele-specific primers may be modified to prevent 5' degradation with a polymerase. Exemplary modifications that may be suitable include phosphorothioate linkages, 2' O-methyl bases, a locked nucleic acid structure, a peptide nucleic acid, or the like. The approach disclosed here is compatible with Competitive Allele-Specific Taqman® (CAST) PCR and other competitive assays. Accordingly, an allele-specific blocker may be present in the assay to suppress signal, if any, resulting from amplification of the wrong allele, although the allele-specific assays disclosed herein may eliminate the need for CAST PCR.

D. Multiplexed Assay of Single-Stranded and Double-Stranded Templates

Figure 12:
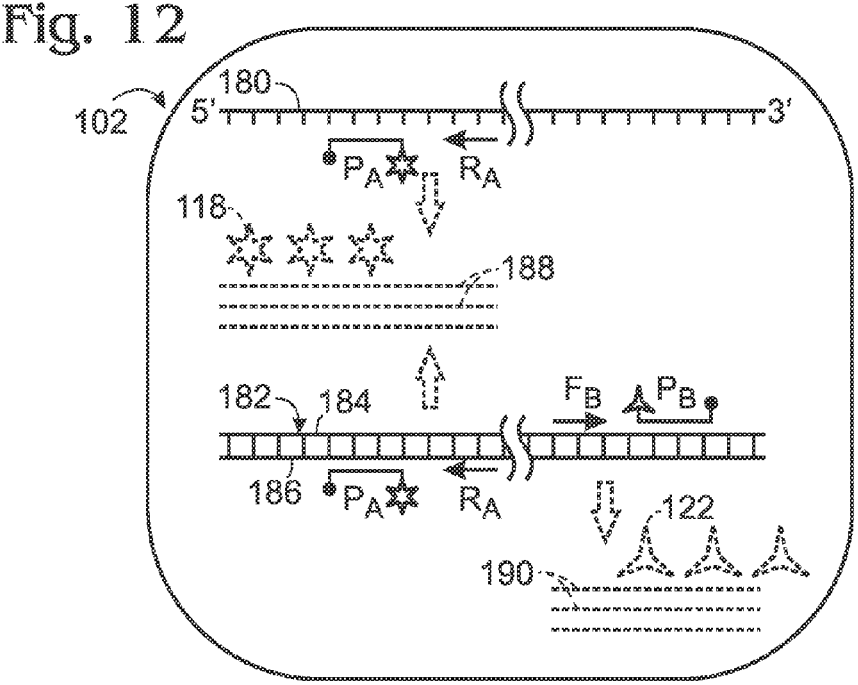
FIG. 12 is a schematic diagram illustrating an exemplary bulk phase for the multiplexed digital assay of FIG. 11, with a strategy for linear amplification of targets in partitions and detection with spectrally distinct probes presented in the bulk phase (copies of single-stranded amplicons and degraded forms of probes are shown in broken lines), in accordance with aspects of the present disclosure.
Figure 13:
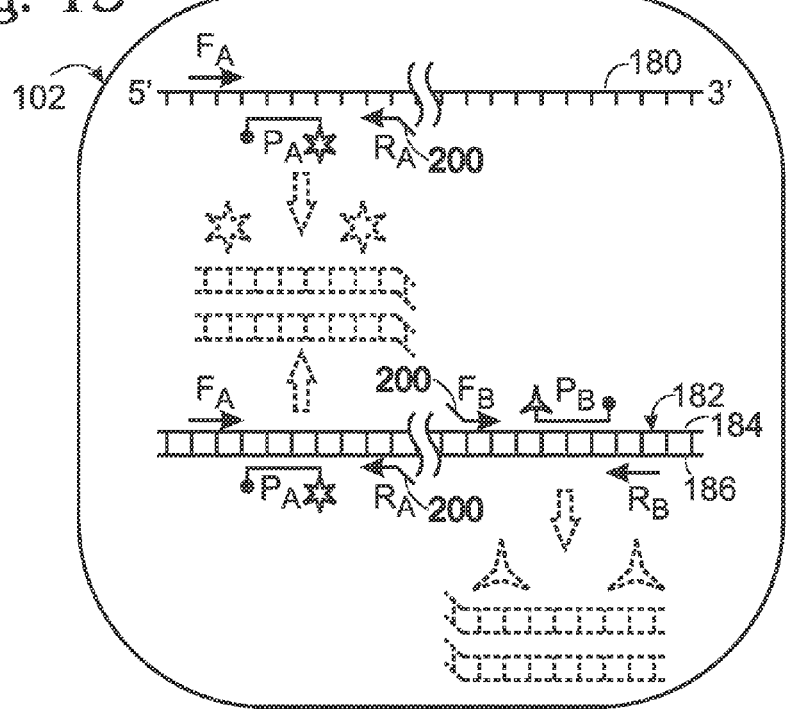
FIG. 13 is a schematic diagram illustrating exemplary aspects of the multiplexed digital assay of FIG. 11, with a strategy for exponential amplification of targets in partitions and detection with spectrally distinct probes presented in the bulk phase (copies of double-stranded amplicons and degraded forms of probes are shown in broken lines), and also presented below the bulk phase as a series of steps, in accordance with aspects of the present disclosure.

This example describes exemplary multiplexed assays for distinguishing and quantifying single-stranded and double-stranded templates; see FIGS. 11-13.

FIG. 11 shows a flowchart of an exemplary method 160 of performing a multiplexed digital assay for a single-stranded template and a double-stranded template. The method steps presented here can be performed in any suitable order and combination and may be combined with or modified by any other suitable aspects of the present disclosure. The templates interchangeably may be termed single-stranded and double-stranded analytes.

Partitions may be provided (e.g., formed) containing the templates at partial occupancy, indicated at 162. The double-stranded template has a first strand and a second strand that are complementary to each other and capable of base-pairing to form a duplex. The single-stranded template and the first strand both contain a first target that is amplifiable with the same primer or primer pair. The first target may be identical in sequence or related but distinct, in the single-stranded template and the first strand. In any event, the single-stranded template and the first strand share at least a region of sequence identity or similarity that includes one or more primer binding sites for the same one or more amplification primers. The single-stranded template and the first strand may have complete sequence identity or one or more regions of sequence difference.

The first target and the second target may be amplified, indicated at 164. The first target represents the first template and the first strand of the second template, and the second target represents the second strand of the second template. In other words, each target is strand-specific. Data may be collected for amplification of the targets, indicated at 166.

A level, such as a concentration, of each template may be determined based on the data. In some cases, the concentration of the double-stranded template may be determined based on a count of the partitions that test positive for both targets, and the concentration of the single-stranded template based on a count of the partitions that test positive for only the first target (optionally with a correction/adjustment for partitions expected to contain both templates by chance). In any event, the data may include different signals for single-stranded and double-stranded templates and thereby allow a quantitative measure of the respective amounts of the two templates.

The method of FIG. 11 may be utilized to distinguish single-stranded from double-stranded templates. The double-stranded template generates signal in both target assays and co-localization is non-random. Single-stranded templates show signal in only one of the target assays because only one strand is present, and co-localization with the double-stranded template is random.

The amount of single-stranded template or the ratio of single-stranded to double-stranded template is inherently informative in many situations. For example, distinguishing pre-miRNA (double stranded) from mature miRNA (single stranded), genomic DNA (gDNA) (double stranded) from mRNA (single stranded) if using a one-step mix for reverse transcription of the mRNA to cDNA and amplification of the cDNA, genomic DNA (gDNA) (double stranded) from cDNA (single stranded), or the like.

A variety of techniques (DGGE, COLD-PCR, HRM, etc.) are known that characterize sequence differences based on differential melting of the products either as homoduplexes or in heteroduplex form. Partitioning the products after treatment and characterizing whether the products were single or double stranded, based on the degree of linkage observed, is another way to characterize sequence differences.

FIG. 12 shows a schematic diagram illustrating an exemplary bulk phase 102 for the multiplexed digital assay of FIG. 11. A single-stranded template 180 and a double-stranded template 182 are present. Template 180 and a first strand 184 of template 182 each provide a same or related first target that is amplifiable by linear amplification with a single primer, $R_A$, to generate single-strand amplicons 188. Generation of amplicons 188 is detectable with a probe, $P_A$, that is cleaved to produce increased fluorescence of fluorophore 118. A second strand 186 of template 182 provides a second target that is amplifiable by linear amplification with a single primer, $F_B$, to generate single-strand amplicons 190. Generation of amplicons 190 is detectable with a probe, $P_B$, that is cleaved to produce increased fluorescence of fluorophore 122. In other embodiments, the probes for the two targets may not be spectrally distinct. In other embodiments, the amplification may be rendered exponential with branched DNA, rolling circle amplification, or the like.

FIG. 13 shows a schematic diagram illustrating additional exemplary aspects of the multiplexed digital assay of FIG. 11. Here, a strategy is depicted for exponential amplification of strand-specific targets. A first-round primer, $R_A$ or $F_B$, may be utilized to perform a first, low-stringency cycle of amplification. Each first-round primer may have an unpaired 5' tail 200 and/or one or more internal mismatches with the template. The first-round primer can prime efficiently on the corresponding template at lower stringency (e.g., a lower annealing temperature) but not at a higher stringency (e.g., a higher annealing temperature). The strands produced during that first round incorporate the full primer sequence providing modified product templates suitable for higher stringency binding of the first-round primers in subsequent rounds. Accordingly, the strands generated during the first, low-stringency cycle of amplification generate product templates for subsequent cycles of amplification at a higher stringency using primer pairs $F_A$ and $R_A$, and $F_B$ and $R_B$, but the original template cannot. As a result, the amplification of each target is dependent on the correct strand of template being present before the first cycle. Partitions that test positive for only the first target contain the single-stranded template, and partitions that are positive for both the first and second targets contain the double-stranded template (and, randomly, the single-stranded template, too).

E. Further Aspects

This section describes further aspects of multiplexed assays with associated targets.

A multiplexed assay may be designed to distinguish a single-stranded target from a double-stranded target. The multiplexed assay may include two assays. The double-stranded target may generate a positive signal in both assays and co-localization should occur at a frequency above chance alone. Single-stranded targets may show signal from only one of the assays if the other strand is not present in a partition, or may generate a positive signal in both assays (dual positives), but due to chance co-localization with a copy of the double-stranded target.

Denaturing a template before partitioning can double the number of positive partitions. The present disclosure involves determining levels of single- and double-stranded target, and optionally determining a ratio involving both levels, because the level of single-stranded product is inherently informative in many situations. For example, distinguishing pre-miRNA (double-stranded) from mature miRNA (single-stranded), distinguishing genomic DNA (double-stranded) from RNA (single-stranded) if using a one step mix, or genomic DNA (double-stranded) from cDNA (single-stranded). A variety of techniques (DGGE, COLD-PCR, HRM, etc.) are known in the art that characterize sequence differences based on differential melting of the products either as homoduplexes or in heteroduplex form. Partitioning the products after treatment and characterizing whether the products were single-stranded or double-stranded is another way to characterize sequence differences.

The use of two allele-specific assays provides another example of a multiplexed assay. Taqman® probes may be used for the assays if they are sufficiently offset. Another embodiment may use two allele-specific primers, one targeting each strand and each ending with the 3' base on the SNP site for the respective strands. These allele-specific primers could also serve as a probe (for example, Scorpion® primers, Amplifluor® primers, fluorescent primers with an internal RNA base, etc.) although other embodiments are possible. It could likewise be done with an intercalating dye such as EvaGreen® dye as a nonspecific reporter for both assays, and designing the assays to have distinguishable luminescence endpoints (of different amplitude). However, the use of two labeled primers with a different fluorophore on each primer is the simplest approach to illustrate.

The allele-specific primers each may have a modification to prevent each primer from getting degraded from its 5' end, depending on the polymerase used. The modification may, for example, be one or more phosphorothioate linkages, 2' O-methyl bases, a locked nucleic acid, etc. It might be advantageous to use deliberate mismatched bases about 3 bp upstream, or other known specificity enhancers for allele-specific PCR.

Other than the allele-specific primer binding region, the amplicons may not overlap. Each may have its own reverse primer, and a probe if a probe-based assay is used for detection.

An advantage of the approach is that allele-specific PCR has a false positive rate, and the primer sequence is incorporated into the amplicon. Accordingly, once a mistake is made, the discrimination is lost for that amplicon. If the amplicons are offset, a mis-incorporation on one will not cause the other assay to mis-prime. As a result, one false positive will result for a partition, but not a false positive for both assays in the partition, unless there is mis-incorporation on both strands. As with the general method, this approach should greatly reduce the dual false positive rate.

One fundamental limit to the low end limit of detection is the false positive rate. Fundamentally, the LOD needs to be not only higher than the false positive rate, but it may need to be high enough that less than 5% of the most abundant false positives are lower than the lowest 5% of the distribution expected from the LOD. Thus the true or average LOD may be a fair amount higher than the number of observed false positives. One way to really drive down the LOD is to use two assays targeting the same template and look for co-localization to identify the true positives from the false positives. The effective false positive rate, or the false dual positive rate should be much lower than the single false positive rate. Thus the real LOD may be reduced down to the limit where assay false positives are no longer the main limit on the low end. Things like carryover, which can be reduced through stealth wells and other approaches can then be the lower limit. This is particularly useful together with separating the quantification of different targets such as detecting HIV and human DNA in separate wells. If two assays are directed to HIV, one with a FAM dye-labeled probe and one with a VIC dye-labeled probe and characterize only the dual positives as the positives, we may be able to achieve a lower LOD. There may be a false negative rate due to assay failures or degradation of the DNA. This can be measured separately and accounted for, or otherwise compensated for.

The false positive rate in a digital PCR assay may consist of several types of possible "false" positive droplets: carryover, sample contamination, and assay false positives, among others. Even a low false positive rate has a relatively large effect on the LOD. The power to distinguish the false positives from the observed rate for low abundance samples is poor. This two-assay approach is primarily to assay false positives. The false positive could be primer/probe dimers, other off target amplification, or non-specific cleavage of probe. This approach could also be advantageous when the source of contamination is an amplicon produced in an earlier reaction, as the different targets would be unlinked.

A multiplexed assay can be configured to include at least two assays targeting different regions of the same target (e.g., the same template). Only partitions positive for both assays are positive for the template of interest. Each assay may have a false positive rate, but unless the assays interact, the rates will be independent of one another. The rate of false dual positives may be determined by the abundance of the two single positives, but may be much lower than either single positive rate. In the regime where false positives are relatively rare, the rate of dual false positives may be extremely low.

Concentration estimates can be revised in several ways. A correction can be introduced that accounts for "expected" dual positives based on the two single positive rates (likely small at most loading conditions where LOD is relevant). A correction can be introduced for true single positives (effectively, false negatives) based on the degree of linkage, degradation state of the template, and intrinsic assay failure rates between assays, among others. Other targets (such as human gDNA in an HIV assay) can be measured in the same multiplexed assay or in a different assay, e.g., in a separate well(s).

IV. Identification of Biological Particles Based on Associated Targets

This section presents selected aspects and embodiments of the present disclosure related to methods of performing digital assays with associated targets to detect, identify, and quantify biological particles, such as biological cells and virions; see FIGS. 14-18.

A. Introduction

Nucleic acids and proteins from organisms can be detected in order to search for useful genes, diagnose diseases or identify organisms. Molecular approaches designed to describe organism diversity or identify analyte organisms in a sample routinely rely upon classifying heterogeneous nucleic acids amplified by PCR (polymerase chain reaction). The resulting mixed amplicons can be quickly, but coarsely, typed into anonymous groups using T-/RFLP (Terminal Restriction Fragment Length Polymorphism), SSCP (single-strand conformation polymorphism), or T/DGGE (temperature/denaturing gradient gel electrophoresis). These groups can be classified through sequencing, but this requires additional labor to physically isolate each 16S RNA type, does not scale well for large comparative studies such as environmental monitoring, and is only suitable for low complexity environments. Also, the number of clones that would be required to adequately catalogue the majority of taxa in a sample is too large to be efficiently or economically handled. Finally, cross reactivity of binding partners or other detection reagents make it difficult to definitively identify a particular organism. As such, a method is needed to efficiently analyze a plurality of organisms without the disadvantages of the above technologies.

The present disclosure provides a system, including methods, composition, and kits for identifying and quantifying biological particles of interest. An exemplary method of identifying a type of particle of interest is provided. In the method, a sample may be provided, with the sample comprising at least two types of biological particles, or a nucleic acid prepared therefrom. The sample may be partitioned into a set of partitions. A presence or an absence of each of at least two targets within each partition may be detected. The presence of a particular set or subset of the at least two targets in a single partition identifies the type of cell or virion in said single partition.

The molecular detection of bacteria and other organisms using nucleic acid targets is often limited by the specificity of the assay. Assays that successfully distinguish among known species may cross-react with other unknown species whether those species are closely related or not. For pathogen detection, there can be cross-reactivity with other species whether they are pathogenic or not. However, often one binding partner set is not sufficient to achieve the desired specificity. Quantitative PCR, or qPCR, can be utilized to detect and identify organisms. However, especially for RNA targets, differences in abundances between organisms make it difficult or impossible to achieve quantitative data regarding relative or absolute organismal abundance in a sample. Methods utilizing multiple binding partner sets (primers and/or probes) can increase specificity, but it can be difficult or impossible to distinguish detection of the intended analyte organism from a mixture of two or more different cross-reacting organisms.

Methods for detection of organisms that include a partitioning step can greatly improve the detection by assaying the partition for two or more targets simultaneously. Such methods can provide the ability to measure co-localization of multiple targets (e.g., 2, 3, 4, 5, 6, 7, 8, 9, 10 or more) in a set of partitions. In some cases, the multiple targets are associated. For example, the multiple targets can be present in single particles. As another example, the multiple targets can be present in a single piece of nucleic acid, e.g., cDNA, plasmid, chromosome, an RNA transcript, rRNA, cRNA, genome, or mitochondrial or chloroplast genome. Thus, detection of co-localization of the multiple targets in a partition can identify partitions that contain or contained a biological particle of interest, or nucleic acid prepared therefrom. The observed frequency of co-localization can be compared to the expected frequency of random co-localization, to determine a frequency of non-random co-localization, thereby determining the number of partitions containing the particle of interest.

In some embodiments, the methods, compositions, and kits provided herein provide improved detection of organisms or groups of organisms of interest. In some cases, the improved detection is provided by detecting multiple targets in which each target is not specific to the type of particle, organism, or group of interest, but also identifies one or more other types of particles, organisms, or groups not of interest (i.e., the target exhibits cross-reactivity). Detection of co-localization of multiple targets with differing cross-reactivity in individual partitions within a set of partitions can provide discrimination between different types of biological particles even if no single target is specific to only one type of interest.

Methods, compositions, and kits are provided for identifying one or more types of particles in a sample by partitioning the sample and detecting the presence or absence of at least two targets in individual partitions. Such methods, compositions, and kits can be useful for determining the presence of a type of particle in a sample. In some cases, such compositions and kits can be useful for determining the relative or absolute abundance of a type of particle in a sample. Such methods, compositions and kits can also be useful for diagnosing a disease or condition associated with the presence or absence of a type of particle of interest.

B. Compositions for Detection of a Biological Particle of Interest

In one aspect, the present disclosure relates to methods of detecting a type of biological particle of interest in a sample using two or more specific binding partners that bind to targets (and/or corresponding products) provided by or formed from the type of biological particle. Without being bound to a particular theory, it is believed that when a sample is partitioned to have a small number of targets per partition (e.g., on average fewer than about 5, 4, 3, 2, or 1 target(s) per partition), the likelihood that multiple different targets will co-localize to a particular partition by chance can be calculated. Binding of multiple different specific binding partners to the targets (or products therefrom) of the particle of interest results in co-localization of the binding partners due to their forced physical proximity. The presence of particles of interest increases the frequency of co-localization.

Similarly, when a sample is partitioned so that there are a small number of particles of interest per partition (e.g., on average fewer than about 5, 4, 3, 2, or 1 particles of interest per partition), the likelihood that a set of particles (e.g., 2 or more different types) that each react with a different set of specific binding partners will co-localize in a partition can be minimized or calculated and accommodated. Thus, for a sample that is partitioned to have a small number of targets and/or particles per partition, the abundance of co-localization of targets/particles in partitions can be used to calculate the absolute or relative concentration of a particle of interest.

In some embodiments, the method comprises detecting the targets using specific binding partners, which may be reporters. For example, a first target can be detected using a first specific binding partner or a first set of specific binding partners, and a second target can be detected using a second specific binding partner or a second set of specific binding partners. The detecting step can be performed under conditions suitable for specifically binding the first and second binding partners or sets to the first and second targets (or products therefrom). In some embodiments, each specific binding partner is linked to a label (e.g., a first binding partner having a first label, a second binding partner having a second label, etc.) and detecting the presence, absence, and/or co-localization of the two or more labels (e.g., the first label and the second label) in at least one partition.

In some embodiments, the present disclosure provides a set or composition comprising partitions each of less than about 100 nL and each comprising less than about 2, 3, 4, 5, 6, 7, 8, 9, or 10 particles of interest, or nucleic acid prepared therefrom; a group-specific target detection reagent; a species-specific target detection reagent; and nucleic acid amplification reagents.

i. Samples

The methods of the present disclosure can be used to detect one or more copies of each of one or more types of biological particles in any type of sample. In some embodiments, the sample is a biological sample. Further aspects of samples that may be suitable are described elsewhere herein, such as above in Sections I and II.

ii. Targets

In some embodiments, two or more targets to be detected are one or more of a peptide, a protein (e.g., an antibody, enzyme, growth regulator, clotting factor, phosphoprotein, etc.), a polynucleotide (e.g., DNA, such as rDNA, dsDNA, or ssDNA; RNA, such as rRNA, mRNA or miRNA; DNA-RNA hybrids; etc.), an aptamer, an immunogen, a peptide nucleic acid, a virus, a virus-like particle, a polysaccharide, a carbohydrate, a lipid, a toxin (e.g., viral or bacterial toxins), a microorganism, a drug compound, or a metabolite. In some embodiments, the target to be detected is a protein. In some embodiments, the target is an RNA, e.g., a genomic RNA, an rRNA, a pre-mRNA, an mRNA, or an miRNA.

In some embodiments the targets are rRNA or rDNA sequences (i.e., ribosomal RNA or DNA sequences). For example, the targets can be 5S rRNA or rDNA, 16S rRNA or rDNA, 18S rRNA or rDNA, 23S rRNA or rDNA, 28S rRNA or rDNA, or a combination thereof. Thus, targets of the present disclosure can detect all viruses and analyte organisms from all the kingdoms of life. In some cases, one target is an rRNA or rDNA sequence and another target is not an rRNA or rDNA sequence. For example, one or more rRNA or rDNA sequences can be detected to identify a genus or species of bacteria, and a second target can be detected to identify the presence of a pathogenicity island. The co-localization of the genus or species target and the pathogenicity island target in a partition would thus suggest the presence of an organism of that particular genus or species that harbors a pathogenicity island.

In some cases, at least two targets correspond to rRNA or rDNA. For example, one target may be a group-specific target with a cross-reactivity profile, or corresponding to a binding partner with a cross-reactivity profile, that corresponds to an rRNA or rDNA sequence that is conserved amongst a group of analyte organisms. Another target may also be a group specific target with a different cross-reactivity profile, or corresponding to a binding partner with a different cross-reactivity profile, that corresponds to an rRNA or rDNA sequence that is conserved amongst the same group of analyte organisms. Thus, a partition in which both targets are detected would be identified as containing a member of the group of analyte organisms. Conversely, a partition in which only one of the two targets is detected would be identified as not containing a member of the group of analyte organisms.

In some embodiments, two, three, four, five, or more different targets are to be detected. In some embodiments, where two or more different targets are to be detected, the two or more different targets are the same type of molecule (e.g., two or more proteins present in a cell or two or more DNA polynucleotides). In some embodiments, wherein two or more different targets are to be detected, the two or more different molecules are different types of molecules (e.g., a drug compound interacting with a cell-associated protein or an rRNA and a plasmid).

The number of copies of a particular target in a sample to be analyzed can be 0, or about or at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10,000, 20,000, 30,000, 40,000, or 50,000 or more. In some embodiments, the sample comprises a low concentration and/or copy number of the two or more targets.

In some embodiments, two or more targets are found on the same target molecule. For example, two or more targets, each at or near a different end of a target molecule, can provide for detection of full-length target or discrimination between full length and truncated target molecules. For example, one target can contain the 5' end of a nucleic acid, whereas a second target can contain the 3' end of a nucleic acid. Partitions containing both targets contain analyte organisms that possess a full length target molecule. For example, tumor cells containing an oncogene in which the 5' regulatory sequences are absent can be identified using two or more targets. Such cells can be distinguished from non tumor cells containing the proto-oncogene form in which the 5' regulatory sequences are present.

In some embodiments, the targets contain mutations, polymorphisms, or regions of protein or nucleic acid that are commonly mutated. Detection of a target that contains a common polymorphism can provide for detection of organisms that contain that polymorphism. For example, a target might be a nucleotide sequence that carries a point mutation (e.g., an SNP) relative to wild-type. Detection of the target in a partition identifies analyte organisms that have the point mutation. Detection of an organism with one organism-specific target in a partition in which the point mutation target is not detected identifies wild-type organisms. Alternatively, the target can be the wild-type sequence. In this example, detection of the wild-type sequence in a partition identifies a wild-type organism. Conversely detection of an organism with an organism specific target in a partition in which the wild-type sequence target is not detected identifies organisms containing the mutation.

In some embodiments, two or more targets for detection of full-length versus truncated nucleic acids or proteins can be combined with one or more targets for detection of mutations or wild-type sequences. For example, an analyte organism can contain a target for the amino terminus of a protein, a target for the carboxy terminus of the same protein, and a target for the wild-type sequence of a mutation hot-spot. Detection of the amino and carboxy termini in a partition can identify organisms with full length protein. Detection of the wild-type sequence target in the same partition can identify the organism as having a wild-type protein. Conversely, detection of the absence of the wild-type sequence target in the same partition can identify the analyte organism as having a mutation in that protein.

Targets of the present disclosure include group-specific targets. Group-specific targets include targets that correspond to groups of target molecules. For example, a group specific target can correspond to a conserved region of a set of target molecules. In other cases, group-specific targets are targets, or sets of targets, that correspond to and thus identify a group of analyte organisms (e.g., correspond to organisms of a genus). Group-specific targets can detect targets that are associated with more than one analyte organism or an analyte organism and a non-analyte organism.

For example, group-specific targets can correspond to organisms of a genus or other classification (e.g., species, family, class, order, phylum, kingdom). In some embodiments, group-specific targets can correspond to viruses of a particular taxonomic classification (e.g., RNA viruses, DNA viruses, adenoviridae, parvoviridae, reoviridae, flaviviridae, paramyxoviridae, orthomyxoviridae, etc.). Alternatively, group-specific targets can correspond to a group of organisms that is not delimited by a particular taxon or group of taxa. For example, group specific targets can correspond to organisms that share a particular pathogenicity island or to organisms that share any target conserved amongst the group.

Group-specific targets can also correspond to various cell types, such as cancer cells, immune cells, T-cells, or cells of a particular tissue or organ. In some cases, group-specific targets can correspond to specific types of cancer cells (e.g., lymphoma, leukemia, melanoma, liver cancer).

In some embodiments, group-specific targets exhibit cross reactivity to analyte and non-analyte organisms. By way of example only, some group-specific targets exhibiting cross reactivity can correspond to strains of analyte organism *Staphylococcus aureus*, but can also correspond to various strains of non-analyte organism *Staphylococcus epidermidis*. In some cases, multiple group-specific targets, each exhibiting different cross-reactivity, can provide improved identification of a particular strain, species, genus, or other group of analyte organisms.

Targets of the present disclosure also include species-specific targets. Species-specific targets are group-specific targets that correspond to a more limited number of analyte organisms. For example, some species-specific targets correspond to a particular species, or sub-species, of analyte organism. For example, some species-specific targets of the invention can be detected to identify multiple strains of *Staphylococcus aureus* but cannot be detected to identify *Staphylococcus* in general.

In some embodiments, species-specific targets exhibit cross reactivity to analyte and non-analyte organisms. By way of example only, some species-specific targets exhibiting cross-reactivity correspond to various strains of analyte organism *Staphylococcus aureus*, but can also correspond to various strains of non-analyte organism *Staphylococcus epidermidis*. In some cases, multiple species-specific targets, each exhibiting different cross-reactivity, or a combination of one or more group and one or more species-specific targets, where at least one group-specific target and one species-specific target exhibit different cross reactivity, can provide improved identification of a particular strain, species or other group of analyte organism.

Targets of the present disclosure also include strain-specific targets. Strain-specific targets are targets that correspond to a specific analyte organism. For example, some strain-specific targets correspond to a particular strain of analyte organism. For example, some strain-specific binding partners of the invention correspond to a specific strain of methicillin resistant *Staphylococcus aureus* but do not correspond to strains of *Staphylococcus aureus* in general.

As another example, some strain-specific targets of the present disclosure correspond to a particular mutation or other molecular target associated with a specific analyte organism. For example, targets are provided by the present disclosure that correspond to one or more oncogenic mutations (e.g., mutations of Ras, KRAS, p53, SRC, MYC, etc.) or one or more mutations of a tumor suppressor (e.g., BRCA1, BRCA2, etc.). As another example, targets are provided that correspond to one or more indicators of cancer malignancy, aggressiveness, or metastasis. As yet another example, targets are provided that correspond to one or more indicators of tissue type (e.g., liver cell, skin cell, bone marrow cell, etc.) or cell type (e.g., T-Cell, B-Cell, hematopoietic cell, etc.).

In some embodiments, strain-specific targets exhibit cross reactivity to analyte and non-analyte organisms. By way of example only, some strain-specific targets exhibiting cross-reactivity can correspond to a particular strain of analyte organism methicillin resistant *Staphylococcus aureus*, but can also correspond to one or more strains of non-analyte organisms. In some cases, multiple strain-specific targets, each exhibiting different cross-reactivity, or a combination of group, species, or strain specific targets, at least two of which exhibit different cross reactivity, can provide improved identification of a particular strain, species, or other group of analyte organism.

Strain specific targets include targets that correspond to markers of pathogenicity or malignancy. For example, strain-specific targets include targets that correspond to markers associated with methicillin resistance. As another example, strain-specific targets include targets that correspond to a pathogenicity island such as haemolysin, cytotoxic necrosing factor, uropathogenic specific protein, pili protein sequences associated with pathogenicity, *Yersinia pestis* high pathogenicity island, *Yersinia pestis* pPCP1 and pMT1, *Salmonella* SP1 and SP2, *Rhodococcus equi* virulence plasmid, the SaPI family of *Staphylococcus aureus* pathogenicity islands, toxic shock syndrome toxin, cholera toxin, *diphtheria* toxin, neurotoxins of *Clostridium botulinum*, cytotoxin of *Psuedomonas aureginosa*, or the Cag pathogenicity island of *H. pylori*.

iii. Binding Partners

A binding partner suitable for use according to the methods described herein is any molecule that specifically interacts with or specifically binds to a target or a product therefrom. As such, binding partners of the present disclosure can be used to detect the target to which it binds. The methods of the present disclosure utilize two or more binding partners (e.g., 2, 3, 4, 5, or more binding partners). In some embodiments, each of the two or more binding partners bind to a target provided by the same analyte organism.

Binding partners of the present disclosure can cross-react with analyte and non-analyte organisms. In some cases, multiple binding partners with different cross reactivity can provide improved detection of analyte organisms. For example, detection of co-localization of two or more binding partners with differing cross-reactivity in the same partition can provide definitive identification of the analyte organism in that partition. In some cases, cross reactivity of a binding partner is related to cross reactivity of the corresponding target. For example, a binding partner corresponds to a target that is present in multiple organisms (e.g., analyte and non-analyte organisms). Alternatively, the cross reactivity of a binding partner can, in some cases, be unrelated to cross reactivity of the corresponding target. For example, a binding partner may correspond to a target that is unique for the group, species, or strain of analyte organism, but it may also bind to or otherwise detect non-analyte organisms.

In some embodiments, the sample is incubated with the two or more binding partners prior to partitioning the sample. In some embodiments, the two or more binding partners are present in a mixture. The mixture comprising the two or more binding partners can include one or more buffers (e.g., aqueous buffers) and optionally one or more additives (e.g., blocking agents or biopreservatives).

As described below, in some embodiments, each of the two or more binding partners is designed to specifically bind to the same target (e.g., at distinct targets (e.g., locations or sequences) on the same target), if present. For example, each of the two or more binding partners can bind to a different region of the same rRNA or rDNA. In some embodiments, the two or more binding partners are designed to specifically bind to different targets, if present. For example, one binding partner can bind to rRNA or rDNA and another binding partner can bind to a pathogenicity island. The sample is incubated with the two or more binding partners (e.g., in a mixture with the two or more binding partners) under conditions suitable for specifically binding the two or more binding partners to the one or more targets, thereby binding to the two or more targets.

In some embodiments, the 2, 3, 4, 5, or more binding partners are the same type of molecule (e.g., all antibodies). In some embodiments, at least two of the 2, 3, 4, 5 or more binding partners are the same type of molecule (e.g., at least two are antibodies). In some embodiments, the 2, 3, 4, 5, or more binding partners are different types of molecules (e.g., an antibody and a nucleic acid).

In some embodiments, the binding partner is a peptide, polypeptide, or protein. As used herein, the terms "peptide," "polypeptide," and "protein" interchangeably refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. In some embodiments, the binding partner is an antibody. As used herein, "antibody" refers to a polypeptide of the immunoglobulin family or a polypeptide comprising fragments of an immunoglobulin that is capable of noncovalently, reversibly, and in a specific manner binding a corresponding antigen. The term antibody also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). Methods for the preparation of antibodies are known in the art; see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). In some embodiments, the binding partner is a non-antibody protein scaffold. As used herein, a "non-antibody protein scaffold" refers to a non-immunogenic polypeptide that is capable of binding to a target with high specificity. In some embodiments, the protein scaffold has a structure derived from protein A, a lipocalin, a fibronectin domain, an ankyrin consensus repeat domain, or thioredoxin. Methods of preparing non-antibody scaffolds are known in the art; see, e.g., Binz and Pluckthun, *Curr Opin Biotechnol* 16:459-469 (2005); Koide et al., *J Mol Biol* 415:393-405 (2012); and Gilbreth and Koide, *Curr Opin Struct Biol* 22:413-420 (2012).

In some embodiments, the probe is a nucleic acid. In some embodiments, the binding partner is an aptamer. An "aptamer," as used herein, refers to a DNA or RNA molecule that has a specific binding affinity for a target, such as a protein or nucleic acid. In some embodiments, aptamers are selected from random pools based on their ability to bind other molecules with high affinity specificity based on non-Watson and Crick interactions with the target molecule (see, e.g., Cox and Ellington, *Bioorg. Med. Chem.* 9:2525-2531 (2001); Lee et al., *Nuc. Acids Res.* 32:D95-D100 (2004)). For example, aptamers can be selected using a selection process known as Systematic Evolution of Ligands by Exponential Enrichment (SELEX). See, e.g., Gold et al., U.S. Pat. No. 5,270,163. Aptamers can be selected which bind, for example, nucleic acids, proteins, small organic compounds, vitamins, or inorganic compounds.

In some embodiments, the binding partner is a nucleic acid primer or a set of nucleic acid primers. For example, the binding partner is a nucleic acid primer designed to hybridize to a target molecule and prime an amplification reaction.

In some cases, the primer is a PCR primer or a primer for other nucleic acid amplification techniques known in the art, including but not limited to the ligase chain reaction (LCR), the transcription based amplification system (TAS), nucleic acid sequence-based amplification (NASBA), strand displacement amplification (SDA), rolling circle amplification (RCA), hyper-branched RCA (HRCA), and thermophilic helicase-dependent DNA amplification (tHDA).

Binding partners of the present disclosure include group specific binding partners. Group specific binding partners include binding partners that bind to groups of target molecules. For example, a group specific binding partner can bind to a conserved region of a set of target molecules. In other cases, group specific binding partners are binding partners, or sets of binding partners, that bind to and thus detect a target that is associated with a group of analyte organisms. Group specific binding partners can detect targets that are associated with more than one analyte organism or an analyte organism and a non-analyte organism.

For example, group specific binding partners can detect organisms of a genus or other classification (e.g., species, class, order, phylum, kingdom). In some embodiments, group specific binding partners can detect viruses of a particular taxonomic classification (e.g., RNA viruses, DNA viruses, adenoviridae, parvoviridae, reoviridae, flaviviridae, paramyxoviridae, orthomyxoviridae, etc.). Alternatively, group specific binding partners can detect organisms that contain a target that is not delimited by a particular taxon or group of taxa. For example, group specific binding partners can detect organisms that share a particular pathogenicity island or organisms that share any conserved target (e.g., any conserved nucleic acid, protein, carbohydrate, etc.).

Group specific binding partners can also detect various cell types, such as cancer cells, immune cells, T-cells, or cells of a particular tissue or organ. In some cases, group specific binding partners can detect specific types of cancer cells (e.g., lymphoma, leukemia, melanoma, liver cancer).

In some embodiments, group specific binding partners exhibit cross reactivity to analyte and non-analyte organisms. By way of example only, some group specific binding partners exhibiting cross reactivity can detect targets associated with various strains of analyte organism *Bacillus anthracis*, but can also detect targets associated with various strains of non-analyte organism *Bacillus thuringiensis*. In some cases, multiple group specific binding partners, each exhibiting different cross-reactivity, can provide improved identification of a particular strain, species or other group of analyte organism. In some cases, group specific binding partners exhibit cross reactivity because they detect targets present in analyte and non-analyte organisms. In other cases, group specific binding partners exhibit cross reactivity because they detect unique targets, but also bind to or detect non-analyte organisms. In still other cases, group specific binding partners can exhibit both types of cross reactivity.

Binding partners of the present disclosure also include species-specific binding partners. Species-specific binding partners are group specific binding partners that detect a more limited number of targets. For example, some species-specific binding partners can detect targets associated with a particular species, or sub-species, of analyte organism. For example, some species-specific binding partners of the invention can be utilized to detect targets of strains of *Bacillus anthracis* but do not detect targets that correspond to Bacilli in general.

In some embodiments, species-specific binding partners exhibit cross reactivity to analyte and non-analyte organisms. By way of example only, some species-specific binding partners exhibiting cross reactivity can detect targets associated with various strains of analyte organism *Bacillus anthracis*, but can also detect targets associated with various strains of non-analyte organism *Bacillus thuringiensis*. Alternatively, or in addition, some species-specific binding partners exhibiting cross reactivity can detect targets that are unique to an analyte species, but also detect non-analyte species. Similarly, some species-specific binding partners exhibiting cross reactivity detect targets that are not unique to the analyte species. In some cases, multiple species-specific binding partners, each exhibiting different cross-reactivity, or group and species-specific binding partners, each exhibiting different cross reactivity, can provide improved identification of a particular strain, species or other group of analyte organism.

Binding partners can also include strain specific binding partners. Strain specific binding partners are binding partners that detect a specific target, or a specific target associated with a specific analyte organism. Some strain specific binding partners can detect targets associated with a particular strain of analyte organism. For example, some strain specific binding partners of the invention detect the target of a specific strain of *Bacillus anthracis* but do not detect targets present in strains of *Bacillus anthracis* in general.

In some embodiments, strain specific binding partners exhibit cross reactivity to analyte and non-analyte organisms. By way of example only, some strain specific binding partners exhibiting cross reactivity can detect targets associated with a particular strain of analyte organism *Bacillus anthracis*, but can also detect targets associated with one or more strains of non-analyte organisms. In some cases, multiple strain specific binding partners, each exhibiting different cross-reactivity, or a combination group, species, or strain specific binding partners, each exhibiting different cross reactivity, can provide improved identification of a particular strain, species or other group of analyte organism.

In some cases, strain specific binding partners exhibit cross reactivity because they detect targets present in analyte and non-analyte organisms. In other cases, strain specific binding partners exhibit cross reactivity because they detect unique targets, but also bind to or detect non-analyte organisms. In still other cases, strain specific binding partners can exhibit both types of cross reactivity.

Strain-specific binding partners include binding partners that detect a particular target associated with pathogenicity or malignancy. For example, strain-specific binding partners include binding partners that detect targets associated with methicillin resistance. As another example, strain specific binding partners include binding partners that detect targets associated with a pathogenicity island such as haemolysin, cytotoxic necrosing factor, uropathogenic specific protein, pili protein sequences associated with pathogenicity, *Yersinia pestis* high pathogenicity island, *Yersinia pestis* pPCP1 and pMT1, Salmonella SP1 and SP2, *Rhodococcus equi* virulence plasmid, the SaPI family of *Staphylococcus aureus* pathogenicity islands, toxic shock syndrome toxin, cholera toxin, *diphtheria* toxin, neurotoxins of *Clostridium botulinum*, cytotoxin of *Psuedomonas aureginosa*, or the Cag pathogenicity island of *H. pylori*.

iv. Detectable Labels

The binding partners described herein can be detected by detecting a label that is linked and/or included in the binding partners. The label can be linked directly to the binding partner (e.g., by a covalent bond) or the attachment can be indirect (e.g., using a chelator or linker molecule). The terms "label" and "detectable label" are used synonymously herein. In some embodiments, each binding partner label (e.g., a first label linked to a first binding partner, a second label linked to a second binding partner, etc.) generates a detectable signal and the signals (e.g., a first signal generated by the first label, a second signal generated by the second label, etc.) are distinguishable. In some embodiments, the two or more binding partner labels comprise the same type of agent (e.g., a first label that is a first fluorescent agent and a second label that is a second fluorescent agent). In some embodiments, the two or more binding partner labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, binding partners, or indicators) are known in the art and can be used in the present disclosure. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more binding partners used for detecting a target molecule are each labeled with an optical agent such as a fluorescent agent (e.g., a first binding partner labeled with a first fluorescent label, a second binding partner labeled with a second fluorescent label, etc.), and each binding partner that is labeled with an optical agent is detected by detecting a signal generated by the optical agent (e.g., a fluorescent signal generated by a fluorescent label). In some embodiments, all of the binding partners used for detecting a target molecule are labeled with an optical agent, and each optical agent-labeled binding partner is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{124}$I, $^{125}$I, $^{130}$I, $^{131}$I, $^{111}$In, $^{117}$Lu, $^{13}$N, $^{15}$O, $^{32}$P, $^{33}$P, $^{212}$Pb, $^{103}$Pb, $^{186}$Re, $^{188}$Re, $^{47}$Sc, $^{153}$Sm, $^{89}$Sr, $^{99m}$Tc, $^{88}$Y, and $^{90}$Y. In some embodiments, 2, 3, 4, 5, or more binding partners used for detecting a target are each labeled with a radioisotope (e.g., a first binding partner labeled with a first radioisotope, a second binding partner labeled with a second radioisotope, etc.), and each binding partner that is labeled with a radioisotope is detected by detecting radioactivity generated by the radioisotope. For example, one binding partner can be labeled with a gamma emitter and one binding partner can be labeled with a beta emitter. Alternatively, the binding partners can be labeled with radionuclides that emit the same particle (e.g., alpha, beta, or gamma) at different energies, where the different energies are distinguishable. In some embodiments, all of the binding partners used for detecting a target are labeled with a radioisotope and each labeled binding partner is detected by detecting radioactivity generated by the radioisotope.

In some embodiments, the label is an enzyme, and the binding partner is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more binding partners used for detecting 2, 3, 4, 5 or more targets are each labeled with an enzyme (e.g., a first binding partner labeled with a first enzyme, a second binding partner labeled with a second enzyme, etc.), and each binding partner that is labeled with an enzyme is detected by detecting a product generated by the enzyme. In some embodiments, all of the binding partners used for detecting a target molecule are labeled with an enzyme, and each enzyme-labeled binding partner is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a nucleic acid barcode. As used herein a "barcode" is a short nucleotide sequence (e.g., at least about 4, 6, 8, 10, or 12, nucleotides long) that uniquely defines a binding partner molecule, or a target bound to a binding partner. For example, one or more targets in partitions containing two or more target sequences can be amplified using primers that contain a different barcode sequence in each partition, thus incorporating a unique barcode into the amplified target of each partition. Alternatively, one or more targets in partitions containing at least two targets can be reverse transcribed using primers that contain a different barcode sequence in each partition, thus incorporating a unique barcode sequence into the reverse transcribed target of each partition. Partitions can then be combined, and optionally amplified, without losing track of which partitions contained two or more targets. Thus, presence or absence of the targets comprising each barcode can be counted (e.g., by sequencing) without the necessity of maintaining physical partitions.

The length of the barcode sequence determines how many unique samples can be differentiated. For example, a 4 nucleotide barcode can differentiate 44 or 256 samples or less, a 6 nucleotide barcode can differentiate 4096 different samples or less, and an 8 nucleotide barcode can index 65,536 different samples or less. Additionally, barcodes can be attached to both strands of a double stranded nucleic acid either through barcoded primers for both first and second strand synthesis or through ligation. The use of two distinct barcodes on the two strands increases the number of independent events that can be distinguished.

Alternatively, the same barcode can be attached to the first and second strand. The use of the same barcode, e.g., by incorporating the same barcode in primers for both the first and second strand synthesis in each partition can result in identical barcodes on both strands. The dual barcoding can provide a check against subsequent detection errors such as sequencing or amplification errors confounding downstream analysis and allow detection of either or both strands without compromising quantification. The use of barcode technology is well known in the art, see for example Katsuyuki Shiroguchi, et al. Digital RNA sequencing minimizes sequence-dependent bias and amplification noise with optimized single-molecule barcodes, PNAS (2012); and Smith, A M et al. Highly-multiplexed barcode sequencing: an efficient method for parallel analysis of pooled samples, Nucleic Acids Research Can 11, (2010).

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding partners are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more binding partner labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the binding partners specifically binding a target). Examples of enzymes combining to generate a detectable signal include coupled assays, such as a coupled assay using hexokinase and glucose-6-phosphate dehydrogenase; and a chemiluminescent assay for NAD(P)H coupled to a glucose-6-phosphate dehydrogenase, beta-D-galactosidase, or alkaline phosphatase assay. See, e.g., Maeda et al., *J Biolumin Chemilumin* 1989, 4:140-148.

C. Methods for Detection of a Biological Particle

In some embodiments the methods of the present disclosure include: providing a sample comprising at least two cells or virions, or a nucleic acid prepared therefrom; partitioning the sample into a set of partitions; and detecting the presence or absence of at least two targets within each partition, thereby identifying the cell or virion in the single partition.

In some embodiments, the presence or absence of at least two targets in a partition identifies analyte cells or virions in the partition. In some cases, the presence or absence of targets in a partition identifies that an analyte cell or virion is not present in the partition. For example, a partition may be identified as not containing a methicillin resistant *Staphylococcus* organism, or not containing an enterohemorrhagic bacteria. Methods provided herein are further elucidated below.

i. Providing a Sample

In some embodiments, the invention provides methods for providing a sample. As provided above, a sample can be obtained from essentially any biological or environmental source. Samples can contain analyte cells or virions to be identified, or be suspected of containing analyte cells or virions to be identified. Providing a sample includes obtaining the sample and preparing the sample for the methods provided herein. For example, the sample can be purified, fractionated, or enriched. In some embodiments, sample can be centrifuged to clear debris or to remove soluble material. In some embodiments, a sample can be filtered. For example, a sample containing cells and virions can be filtered to remove cells, and virions can be detected therefrom.

ii. Partitioning

Samples can be partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire content of each of which is incorporated by reference herein.

In some cases, samples are partitioned and detection reagents (e.g., binding partners) are incorporated into the partitioned samples. In other cases, samples are contacted with detection reagents (e.g., binding partners) and the sample is then partitioned. In some embodiments, reagents such as binding partners, primers, buffers, enzymes, substrates, nucleotides, salts, etc. are mixed together prior to partitioning, and then the sample is partitioned. In some cases, the sample is partitioned shortly after mixing reagents together so that substantially all, or the majority, of reactions (e.g., reverse transcription, DNA amplification, DNA cleavage, etc.) occur after partitioning. In other cases, the reagents are mixed at a temperature in which reactions proceed slowly, or not at all, the sample is then partitioned, and the reaction temperature is adjusted to allow the reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which the one or more reactions are inhibited. In some cases, a combination of temperature and time are utilized to avoid substantial reaction prior to partitioning.

Additionally, reagents and sample can be mixed using one or more hot start enzymes, such as a hot start reverse transcriptase or a hot start DNA polymerase. Thus, sample and one or more of buffers, salts, nucleotides, binding partners, labels, enzymes, etc. can be mixed and then partitioned. Subsequently, the reaction catalyzed by the hot start enzyme, can be initiated by heating the partition mixtures to activate the one or more hot-start enzymes.

Additionally, sample and reagents (e.g., one or more of buffers, salts, nucleotides, binding partners, labels, enzymes, etc.) can be mixed together without one or more reagents necessary to initiate an intended reaction (e.g., reverse transcription or DNA amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous sample comprising targets to be detected. In some embodiments, the aqueous sample comprising the targets to be detected further comprises a buffered solution and two or more binding partners for detecting the targets.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w).

In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can or can not be removed prior to heating. The microcapsules can be resistant to coalescence and/or flocculation across a wide range of thermal and mechanical processing.

Following conversion, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers, optionally one or more reverse transcription reactions can be performed, the partitions can then be heated to perform microencapsulation, and the microcapsules can be stored or transported for further analysis.

The microcapsule partitions can contain one or more binding partners (e.g., labeled binding partners as described herein) and can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the sample-binding partner incubations occur in a single well, e.g., a well of a microtiter plate, without inter-mixing between partitions. The microcapsules can also contain other components necessary for the incubation.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that at least a majority of partitions have no more than 5-10 analyte organisms (e.g., no more than about 0.5, 1, 2, 3, 4, 5, 6, 7, 8, 9, or 10 analyte organisms). In some embodiments, the sample is partitioned into a sufficient number of partitions such that at least a majority of partitions have no more than 5-10 analyte and/or non-analyte organisms (e.g., no more than about 0.5, 1, 2, 3, 4, 5, 6, 7, 8, 9, or 10 analyte and/or non-analyte organisms). In some embodiments, a majority of the partitions have no more than 5-10 (e.g., no more than about 0.5, 1, 2, 3, 4, 5, 6, 7, 8, 9, or 10) of the at least two targets to be detected. In some embodiments, on average no more than 5-10 (e.g., no more than about 0.5, 1, 2, 3, 4, 5, 6, 7, 8, 9, or 10) of the at least two targets are present in each partition. In some embodiments, on average about 0.5, 1, 2, 3, 4, or 5 targets are present in each partition. In some embodiments, on average about 0.001, 0.005, 0.01, 0.05, 0.1, 0.5, 1, 2, 3, 4, or 5 targets are present in each partition. In some embodiments, on average about 0.001, 0.005, 0.01, 0.05, 0.1, 0.5, 1, 2, 3, 4, or 5 binding partners are present in each partition.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

iii. Washing

In some embodiments, after a sample is incubated with two or more binding partners under conditions suitable for specifically binding the two or more binding partners to one or more targets, the sample is washed to remove binding partners that do not specifically bind to their targets. In some embodiments, a sample is incubated with a first binding partner, then optionally subjected to wash conditions before incubating the sample with a second binding partner. In some embodiments, serially incubating a sample with a binding partner, then optionally subjecting the sample to wash conditions, then incubating a sample with a different binding partner can be performed for two, three, four, or five binding partners or more.

The selection of appropriate wash conditions, wash buffers, etc. will vary based upon conditions such as binding partner, target molecule, etc., and can be determined by a person skilled in the art. For example, in some embodiments, wherein the binding partner-target complex is denser than the binding partner alone, the sample can be washed by centrifugation to pellet the binding partner-target molecule complex, followed by resuspension in a buffer lacking binding partner. As another example, in some embodiments, a binding partner-target molecule complex can be separated from unbound binding partner by passing the sample through a density gradient or other gradient (e.g., separation by charge). As another example, in some embodiments, a binding partner-target molecule complex can be washed by passing the sample through a column (e.g., size exclusion column) to separate the complex from unbound binding partner. A wash process can be repeated for additional washes as necessary. In some embodiments, the sample is washed before partitioning. In some embodiments, the sample is washed after partitioning. In some embodiments, no intervening wash step is performed after incubation of the sample with the binding partners and before detection of the binding partners.

In some embodiments, the sample is maintained at a controlled temperature or range of temperatures before, during, and/or after partitioning the sample. In some embodiments, the sample is maintained at a temperature of about 20°, 25°, 30°, 35°, 40°, 45°, 50°, 55°, 60°, 65°, 70°, 75°, 80°, 85°, 90°, or 95° C. before, during, and/or after partitioning the sample, e.g., at a temperature to allow for amplification of signal generated by one or more labeled binding partners. In some cases, the sample temperature is cycled before or after partitioning. In some cases, the temperature cycling provides amplification of binding partners, labels, and/or targets.

iv. Detection

A binding partner or a detectable label can be detected using any of a variety of detector devices. Exemplary detection methods include radioactive detection, optical absorbance detection (e.g., fluorescence or chemiluminescence), or mass spectral detection. As a non-limiting example, a fluorescent label can be detected using a detector device equipped with a module to generate excitation light that can be absorbed by a fluorophore, as well as a module to detect light emitted by the fluorophore.

In some embodiments, detectable labels in partitioned samples can be detected in bulk. For example, partitioned samples (e.g., droplets) can be combined into one or more wells of a plate, such as a 96-well or 384-well plate, and the signal(s) (e.g., fluorescent signal(s)) can be detected using a plate reader. In some cases, barcodes can be used to maintain partitioning information after the partitions are combined.

In some embodiments, the detector further comprises handling capabilities for the partitioned samples (e.g., droplets), with individual partitioned samples entering the detector, undergoing detection, and then exiting the detector. In some embodiments, partitioned samples (e.g., droplets) can be detected serially while the partitioned samples are flowing. In some embodiments, partitioned samples (e.g., droplets) are arrayed on a surface and a detector moves relative to the surface, detecting signal(s) at each position containing a single partition. Examples of detectors are provided in WO 2010/036352, the contents of which are incorporated herein by reference. In some embodiments, detectable labels in partitioned samples can be detected serially without flowing the partitioned samples (e.g., using a chamber slide).

Following acquisition of fluorescence detection data, a general purpose computer system (referred to herein as a "host computer") can be used to store and process the data. A computer-executable logic can be employed to perform such functions as subtraction of background signal, assignment of target and/or reference sequences, and quantification of the data. A host computer can be useful for displaying, storing, retrieving, or calculating diagnostic results from the molecular profiling; storing, retrieving, or calculating raw data from expression analysis; or displaying, storing, retrieving, or calculating any sample or patient information useful in the methods of the present disclosure.

The host computer can be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, can be included. Where the host computer is attached to a network, the connections can be provided via any suitable transport media (e.g., wired, optical, and/or wireless media) and any suitable communication protocol (e.g., TCP/IP); the host computer can include suitable networking hardware (e.g., modem, Ethernet card, WiFi card). The host computer can implement any of a variety of operating systems, including UNIX, Linux, Microsoft Windows, MacOS, or any other operating system.

Computer code can be written in a variety of languages, including PERL, C, C++, Java, JavaScript, VBScript, AWK, or any other scripting or programming language that can be executed on the host computer or that can be compiled to execute on the host computer. Code can also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface can be provided, allowing the user to control operations using a pointing device. Thus, the present disclosure is not limited to any particular user interface.

Scripts or programs incorporating various features of the present disclosure can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

In some embodiments, the host computer can contain a database, such as a database on computer readable media. Such a database can contain a list of targets or the analyte organisms or group of organisms the targets correspond to. In some cases, the database on computer readable media contains a list of targets and the analyte organisms or group of analyte organisms they correspond to. In some cases, the database can also contain binding partners that detect the targets of the database. The database can also contain cross reactivity information for the targets and/or binding partners.

In some embodiments, a partition or set of partitions can be subject to a detecting step to detect the presence or absence at least two different targets. The pattern of the presence or absence of the at least two targets can then be compared using a computer to the computer readable media containing a database of targets and cross-reactivities. The comparison can provide an identification of the presence or absence of the analyte organism or group in the partition.

D. Exemplary Assays for Types of Biological Particles

This section describes exemplary multiplexed digital assays for identifying, distinguishing, and/or quantifying different types of biological particles; see FIGS. 14-18.

Figure 14:
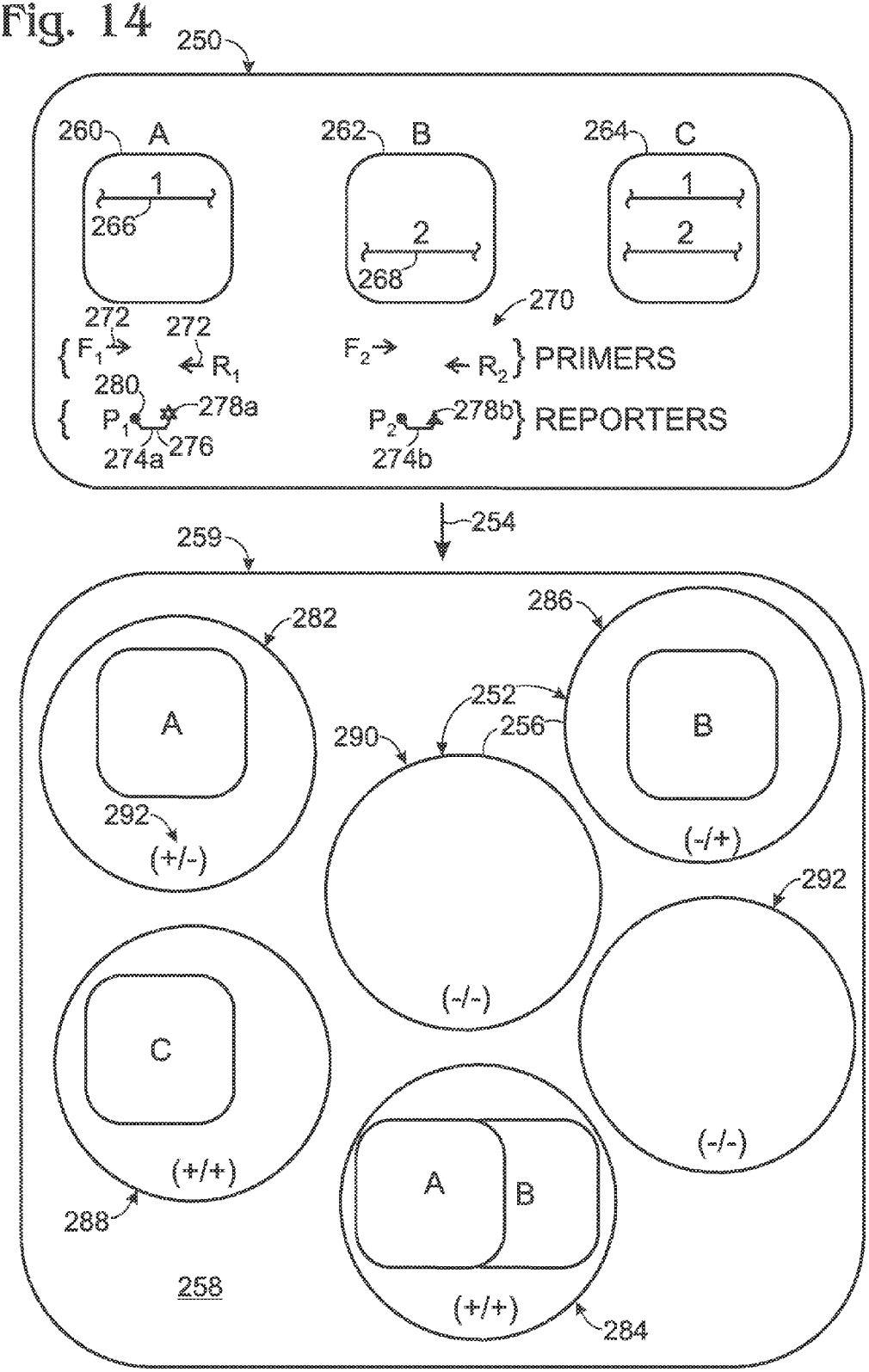
FIG. 14 is a schematic diagram illustrating formation of partitions from a bulk phase including (a) a sample containing three types of biological cells (A, B, and C) and (b) reagents for amplification of a pair of different targets (1 and 2) from nucleic acid in the cells, in accordance with aspects of the present disclosure.

FIG. 14 shows a schematic diagram illustrating a sample-containing fluid or phase bulk 250, and partitions 252 formed, indicated at 254, with portions of the sample-containing fluid. The partitions may, for example, be droplets 256 disposed in a continuous phase 258 that includes oil, to form an emulsion 259.

Fluid 250 may include one or more types of biological particles (e.g., different types of cells), such as types A, B, and C (260, 262, and 264, respectively). Only one copy of each particle type is depicted in FIG. 14, but any suitable number of copies of each type may be present in the sample-containing fluid, such as greater than 2, 5, 10, 100, 1000, etc. Also, the number of copies of each particle type may be different. Each type of biological particle may be at least substantially intact when partitions are formed (such as with a majority of the copies of each type being intact (i.e., unlysed/closed), as shown here, or each type may be opened to release particle contents before partition formation, as described further below.

Each of types A, B, and C may contain a different set or subset of two or more targets 266 and 268 (also identified here as target 1 and target 2, respectively). For example, here, each particle of type A contains at least one copy of only target 1, each particle of type B contains at least one copy of only target 2, and each particle of type C contains at least one copy of each of targets 1 and 2. The targets may be nucleic acid target sequences provided by DNA or RNA within each particle. Targets 1 and 2 in particles of type C are associated with each other because copies of both targets are contained in the same individual type C particles. Targets 1 and 2 may be connected to each other covalently and/or by base pairing within each type C particle or may be present in separate nucleic acids (e.g., discrete chromosomes or RNAs) within each particle.

Fluid 250 also may include detection reagents 270 for detecting the presence or absence of each target in partitions 252. Reagents 270 may include one or more primers 272 for amplification of each target (such as $F_1$ and $R_1$ for target 1 and $F_2$ and $R_2$ for target 2). The reagents also may include a specific reporter, 274a or 274b, for each target, such as probes P$_1$ and P$_2$ for targets 1 and 2, respectively. Each reporter may be photoluminescent. Here, each specific reporter includes a nucleic acid 276 that binds specifically to the corresponding target (and/or an amplicon produced by amplification of the target), a photoluminophore 278a or 278b, and a quencher 280 for the photoluminophore. In other embodiments, the reporter may be a nonspecific reporter, such as an intercalating dye, that binds to each of the targets (and/or an amplicon produced by amplification of the target). The detection reagents also may include an amplification enzyme (e.g., a heat-stable polymerase or ligase), dNTPs (or NTPs), and the like.

Emulsion 259 is illustrated schematically. The emulsion may contain any suitable number of droplets, such as greater than 100 or 1000 droplets, among others. Each droplet 256 of emulsion 259 may contain a complete set of detection reagents 270. However, droplets 256 may contain each of biological particle types A to C at partial occupancy. In other words, each type of biological particle may be present in only a subset of the droplets. In the depicted emulsion, only droplets 282 and 284 contain a type A particle, only droplets 284 and 286 contain a type B particle, and only droplet 288 contains a type C particle. Droplets 290 and 292 do not contain a copy of any of the particle types. Droplet 284 exhibits a random co-localization of two different particle types, namely, types A and B.

The droplets of emulsion 259 may be processed for detection of targets 1 and 2. For example, the droplets may be heated to open the biological particles, combining detection reagents 270 with the targets. The droplets may be heated to any suitable temperature to open the particles, such as at least about 60, 70, 80, or 90 degrees Celsius. In some embodiments, the droplets may be heated to a denaturation temperature above 90 degrees Celsius. The droplets also may be thermocycled, to encourage amplification of the targets. Light may be detected from the droplets (and particularly from the reporters therein) to collect amplification data. A target content 294 detected for each droplet is presented near the bottom of each droplet, with the presence/absence of the first target given before the slash and the presence/absence of the second target given after the slash ("+" means positive/present and "−" means negative/absent).

Figure 15:
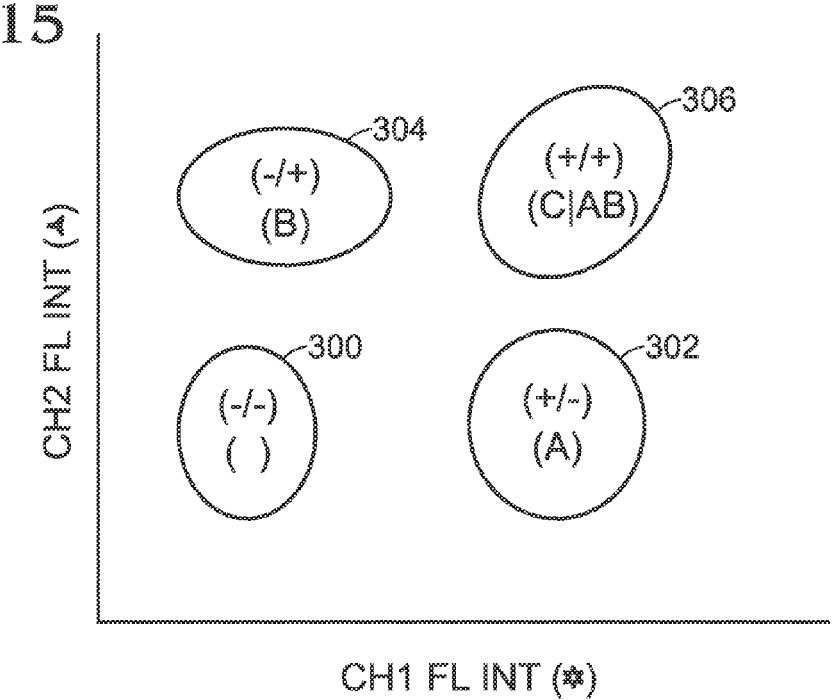
FIG. 15 is a graph of fluorescence intensity (FL INT) data that may be collected in two optical channels (CH1 and CH2) from a set of partitions formed as in FIG. 14, after opening (e.g., lysing) the cells in the partitions and amplification of the targets from nucleic acid provided by the opened cells, in accordance with aspects of the present disclosure.

FIG. 15 shows a graph of fluorescence intensity signals (FL INT) that may be collected from a larger set of droplets that are formed and processed as described above for FIG. 14. The data may be collected in two optical channels (CH1 and CH2) from a set of partitions formed as in FIG. 14, after opening the particles in the droplets and amplification of the targets from nucleic acid provided by the particles. Each optical channel may selectively detect light from only one of the reporters/luminophores in the droplets. Here, channel 1 detects the reporter for target 1, and channel 2 detects the reporter for target 2 (e.g., detecting light predominantly from a degraded form of each reporter). The data may be plotted, with each droplet producing a data point in the graph. The data points may cluster according to target content as shown. The level of each type of biological particle may be determined from the number of droplets (the droplet counts) in the various clusters (e.g., see Section III above). More particularly, the level of type A particles may be determined from droplet counts for clusters 300 and 302. The level of type B particles may be determined from droplet counts for clusters 300 and 304. The level of particle type C may be determined from the droplet counts for all four clusters (300, 302, 304, and 306), with correction for chance co-localization of targets 1 and 2 from particle types A and B in the same droplets (e.g., see Equation 8 in Section III).

Figure 16:
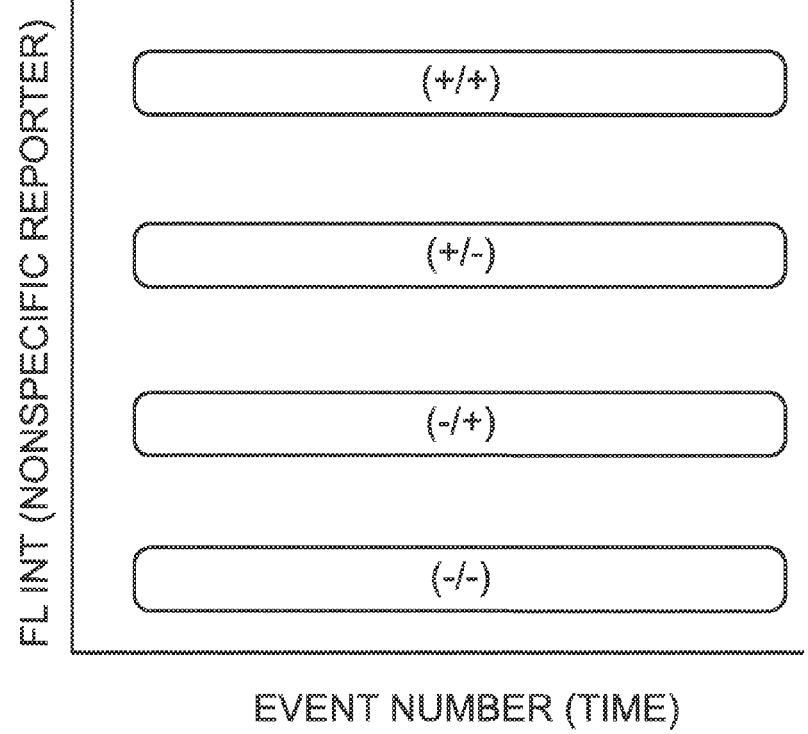
FIG. 16 is a graph of fluorescence intensity (FL INT) data that may be collected as a function of time or partition order in a single optical channel from a set of partitions formed as in FIG. 14, but with the pair of sequence-specific reporters in FIG. 14 replaced by a single nonspecific reporter, such as an intercalating dye, in accordance with aspects of the present disclosure.

FIG. 16 shows a graph of fluorescence intensity signals (FL INT) that may be collected as a function of time or partition order ("event number") in a single optical channel from a set of partitions. The partitions may be droplets formed as in FIG. 14, but with the pair of sequence-specific reporters 274a and 274b replaced by a single nonspecific reporter, such as an intercalating dye. Four clusters or bands may be resolved from each other, with the target content of each indicated as in FIG. 15. Therefore, the partition counts obtained from the graph of FIG. 16 may be processed in the same manner as for FIG. 15.

Figure 17:
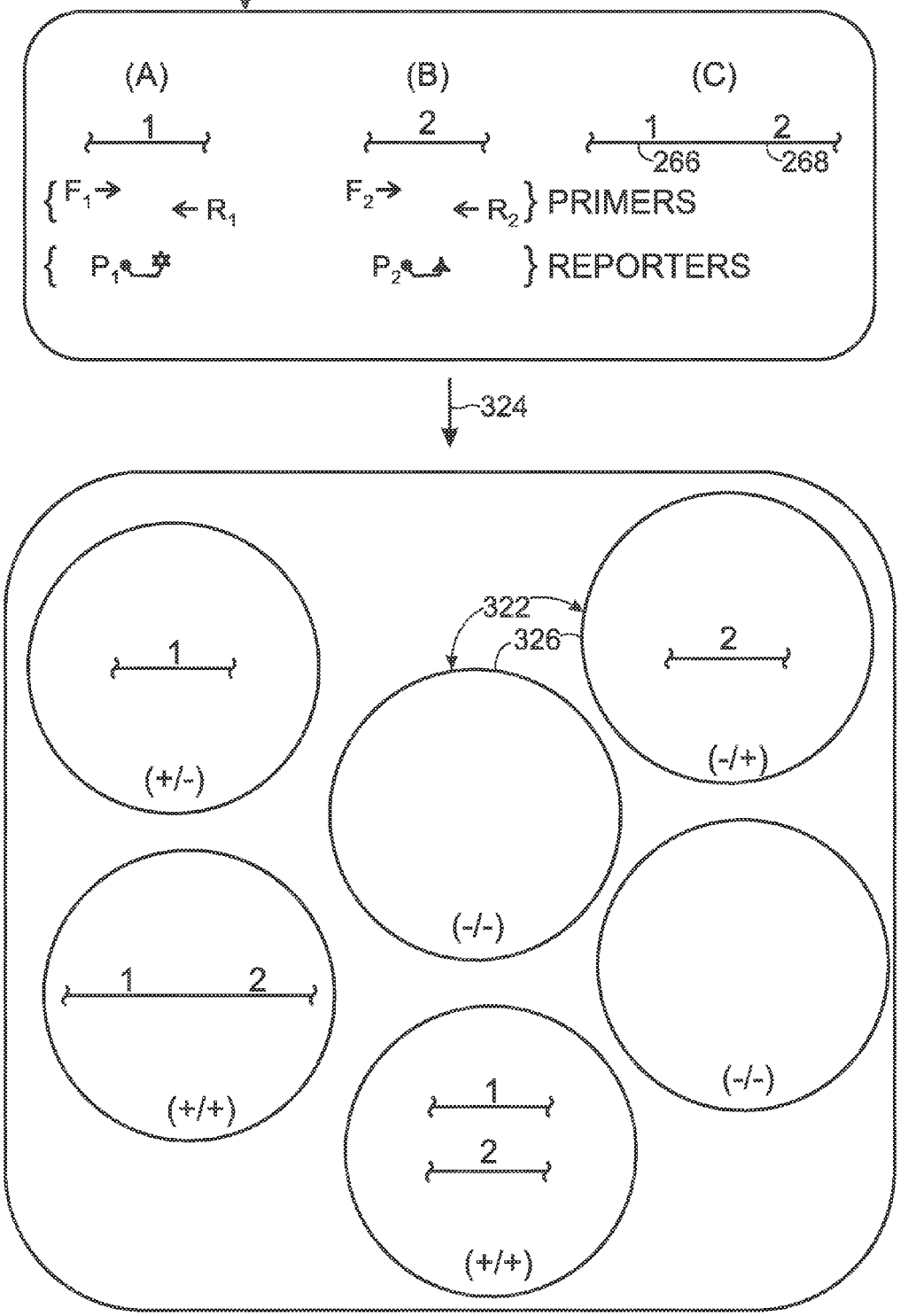
FIG. 17 is a schematic diagram illustrating formation of partitions from a bulk phase including (a) a sample containing nucleic acid prepared from three types of biological cells (A, B, and C), and (b) reagents for amplification of a pair of different targets from the nucleic acid and detection of the amplification, in accordance with aspects of the present disclosure.

FIG. 17 shows a schematic diagram illustrating a sample-containing fluid or phase bulk 320 and partitions 322 formed, indicated at 324, with portions of the sample-containing fluid. The partitions may, for example, be droplets 326. The diagram of FIG. 17 is similar to that of FIG. 14, except that the sample-containing fluid contains nucleic acid prepared from particle types A, B, and C, rather than intact particles. Targets 1 and 2 may be linked to each other in the particles, and sufficiently proximate that the targets remain substantially linked to each other when nucleic acid is prepared from the particles. The droplets may be processed and data collected and analyzed as described above for FIGS. 14 and 15.

FIG. 18 shows a schematic diagram of different types of biological particles that may be present in a sample assayed as described herein. Only one copy of each type is shown to simplify the presentation. The types are arranged in taxonomic groups (taxa) (Groups I, II, III, . . . N), each of which may include at least one or two or more types. The groups may be two or more groups of the same rank, such as two or more classes, orders, families, genera, species, etc. The majority of the types of particles in the sample may be negative for each of at least a pair of targets to be assayed (here, targets 1 and 2). Target 1 may be a marker for Group I, which contains a type 340 of interest and other types 342 not of interest. Target 2 may be a marker that is specific to type 340 within Group I, but that also is present in one or more other types 344 outside of Group I. (Types 340 and 344 each belong to a taxa of higher taxonomic rank than Groups I-N, and also belong to a group of target-2-positive types.) Type 340 can be identified and quantified from partitions positive for both targets, with correction for chance co-localization of targets 1 and 2 from different particle types in the same partitions.

E. Further Aspects

The molecular detection of bacteria and other organisms using nucleic acid targets is often limited by the specificity of the assay. Often, assays that successfully distinguish among known species may cross react with other unknown species whether those species are closely related or not. For pathogen detection, there may be cross reactivity whether the alternate species is pathogenic or not. Often, one primer/probe set is not sufficient to achieve the desired specificity. Digital PCR provides an improvement that greatly improves the detection by using 2 or more targets simultaneously. In qPCR, two assays or two probes targeting the same organism poses a challenge to interpret. The targets may be at different abundances even if the organism is not (especially for RNA targets), and differences in efficiency meant that the quantitative numbers are not likely to match exactly. Thus it is difficult to distinguish the intended target from a mixture of two different cross reacting targets. Droplet digital per, and digital PCR generally, can improve on this by the ability to measure co-localization of the multiple assays and, as with other co-localization approaches, the observed frequency of double positives could be compared to the expected number of double positives to determine the frequency of co-localization due to non-random causes. In this case, because the two targets are physically linked and co-occurrence is due to their proximity at the time of partitioning. This will lead to a better ability to identify and specifically detect particular targets."

Taxonomic (species identification) identification is often not sufficient by itself for identification of pathogens or other functional groups, because the relevant functional genes may be on pathogenicity islands. Likewise, the presence of these same genes may not result in pathogenicity in a different species. Often it is the intersection of combinations of factors that result in pathogenicity or other phenotypes of interest.

An example of where this would be especially useful is MRSA detection. Commonly MRSA detection is done through a pair of PCR assays. One assay that targets *S. aureus*, but detects both MRSA and methicillin sensitive *S. aureus*, paired with an assay that detects the gene responsible for methicillin resistance (which is carried by a number of non-pathogenic bacteria). Thus, the detection requires that two assays are both positive for the sample, but this could occur through the desired analyte organism being present or the combined presence of non-analyte organisms. This assay approach could be greatly enhanced by first partitioning the bacteria into droplets or other partitions, and then assaying for the two targets. MRSA bacteria would result in both targets being in the same partition due to their presence within one cell. False positives would be reduced unless the two different bacteria generating the false positives were physically associated resulting in non-random co-localization.

Another use and example would be identification of species using two probes or assays targeting the same nucleic acid molecule (for example two assays to the same gene, two assays to rRNA, or two assays to different targets that are located on the same nucleic acid molecule (could be genomic DNA, extra-chromosomal element, plasmid, mRNA strand). For example, one could use a group specific assay to one region of the 16S rDNA and a species-specific assay to a different region and look for co-localization. Even if the species-specific assay show cross reactivity to unrelated bacteria, the co-localization of both would indicate the analyte organism. A further application of this type of co-localization for improved identification is the reduction in the level of multiplexing of assays required for identification and an improvement in the ability to quantify mixed assemblages. Using the group specific and species-specific assays as an example again, a group specific assay that is specific to the group of interest but does not distinguish among three members of that group could be paired with assays that alternately distinguish member A from the others or member B from the others. It would not be necessary to have an assay for member c as it could be identified from the single positives. Additionally, this assay combination would allow the simultaneous quantification of all three targets which would be difficult to distinguish in qPCR or other methods, especially if one of the members (e.g., A) is present in low abundance relative to the others.

This would also show a benefit when two or more assays exist for a particular analyte organism of interest but neither assay is specific by itself, but the cross reactivities are different. The co-localization of positives for both assays can be used to determine the abundance of the organism that reacts to both assays.

This same approach can be applied to non-microbial cells, for example mammalian cells. Often, it is a specific subpopulation of cells that is of interest which cannot be specifically identified with one assay but which can be identified by co-localization of multiple assays simultaneously. Assays that show cross reactivity among cells or among possible transcripts can similarly be distinguished by their co-localization. Even though the assays are not specific by themselves, if their cross reactivities are different, then they may be specific in combination V. Examples This section presents selected aspects and embodiments of the present disclosure related to digital assays with associated targets. These examples are intended for illustration only and should not limit or define the entire scope of the present disclosure.

EXAMPLE 1

Selected Embodiments I

This section presents additional selected embodiments of the present disclosure, related to digital assays with associated targets, as a series of indexed paragraphs.

1. A method of performing a multiplexed digital assay, comprising: (A) forming partitions containing a template at partial occupancy, each partition being configured to amplify a first target and a second target from a single copy of the template, if present, in the partition; (B) amplifying the first target and the second target in the partitions; (C) collecting data for amplification of the targets; and (D) determining a level of at least one of the targets (and/or of the template) based on the data and an expected or assumed degree of linkage of the targets to each other.

2. The method of paragraph 1, wherein the degree of linkage represents a connectedness of the targets to each other as the partitions are being formed.

3. The method of paragraph 1 or 2, wherein the step of determining a level of the at least one target is based on an assumption that each partition testing positive for only one of the targets is a false positive.

4. The method of any preceding paragraph, wherein the degree of linkage is at least 80%.

5. The method of any preceding paragraph, wherein the degree of linkage is at least 90%.

6. The method of any preceding paragraph, wherein the linkage is assumed to be 100%.

7. The method of any preceding paragraph, wherein the step of forming partitions includes a step of providing a bulk phase containing the template and a step of dividing the bulk phase into fluid volumes containing the template at partial occupancy.

8. The method of paragraph 7, wherein the fluid volumes are droplets.

9. The method of paragraph 7 or 8, wherein the fluid volumes are the partitions.

10. The method of paragraph 7, wherein the fluid volumes are a first set of fluid volumes, and wherein the step of forming partitions includes a step of fusing individual fluid volumes of the first set with individual fluid volumes of a second set.

11. The method of paragraph 10, wherein the fluid volumes of the second set include at least one primer for amplification of at least one of the targets.

12. The method of paragraph 10 or 11, wherein the fluid volumes of the first set and the second set are droplets.

13. The method of paragraph 1, wherein the template is provided by a sample, further comprising a step of reducing an average size of nucleic acid in the sample before the step of forming partitions.

14. The method of paragraph 13, wherein the step of reducing an average size includes a step of digesting the nucleic acid in the sample with at least one restriction enzyme.

15. The method of paragraph 14, wherein the step of digesting produces copies of the template having a uniform length.

16. The method of any preceding paragraph, wherein more of the partitions test positive for only one of the targets than for both of the targets.

17. The method of any preceding paragraph, wherein the step of collecting data includes a step of generating one or more signal values for each partition, further comprising a step of processing the data by comparing the one or more signal values for each partition with one or more threshold or range values to determine whether the partition tests positive or negative for each target, and wherein, optionally, more of the partitions test positive for one of the targets than both of the targets.

18. The method of any preceding paragraph, further comprising a step of processing the data such that a given partition is counted as positive for both targets if the data indicates the given partition contains both targets and is counted as negative for both targets if the data indicates the given partition contains only one or neither of the targets, wherein the step of determining a level is based on the processed data.

19. The method of any preceding paragraph, wherein the level is a concentration of the at least one target.

20. The method of any of paragraphs 1 to 18, wherein the level is a qualitative level indicating whether or not the at least one target is present above background.

21. The method of any preceding paragraph, wherein the step of determining a level includes (a) a step of calculating an expected number of false double-positives that test positive for both of the targets based on respective counts of partitions positive for each target alone and (b) a step of comparing the expected number of false double-positives to a count of observed double-positives to determine whether the count of observed double-positives is significantly greater the expected number of false double positives.

22. The method of any preceding paragraph, wherein the level is for the first target and includes a linked form of the first target connected to the second target and an unlinked form of the first target not connected to the second target.

23. The method of any preceding paragraph, wherein the level is based in part on a number of the partitions that are expected to be true positives testing positive for only one of the targets.

24. The method of paragraph 23, wherein the number of the partitions is determined based on a count of partitions positive for both targets and the assumed or expected linkage of the targets.

25. The method of any preceding paragraph, wherein the level represents an adjustment of a level calculated for the template to account for unlinked forms of the first and second targets.

26. The method of any preceding paragraph, wherein the linkage is created at least in part by one or more covalent bonds.

27. The method of any preceding paragraph, wherein each target is provided selectively by a different strand of the template, and wherein the linkage is created at least in part by base pairing of the different strands to each other.

28. The method of any preceding paragraph, wherein each target is specific for the same allele.

29. A method of performing a multiplexed digital assay, comprising: (A) forming partitions containing a template at partial occupancy, each partition being configured to amplify a first target and a second target from a single copy of the template, if present, in the partition; (B) amplifying the first target and the second target in the partitions; (C) collecting data for amplification of the targets; and (D) determining a level of at least one of the targets based on the data and with at least a majority of the partitions that test positive for only one of the targets being deemed false positives.

30. The method of paragraph 29, wherein each partition that tests positive for only one of the targets is deemed to be a false positive for the step of determining a level of at least one of the targets.

31. The method of paragraph 29 or 30, wherein the level is a qualitative level indicating whether or not the at least one target is present above background.

32. A method of performing a multiplexed digital assay, comprising: (A) providing partitions containing a template at partial occupancy, each partition being configured to amplify a first target and a second target from a single copy of the template, if present, in the partition; (B) amplifying the first target and the second target in the partitions; (C) collecting data for amplification of the first target and the second target in the partitions; (D) processing the data such that a given partition is counted as positive for both targets if the partition tests positive for both targets and is counted as negative for both targets if the partition tests positive for only one or neither of the targets; and (E) determining a concentration of at least one of the targets based on the processed data.

33. The method of any preceding paragraph, wherein a single copy of the template has a first strand and a second strand that are complementary to each other, and wherein the first target is amplifiable selectively from the first strand and the second target is amplifiable selectively from the second strand.

34. The method of any preceding paragraph, wherein the partitions include a fluorophore-labeled primer involved in amplification of the first target.

35. The method of paragraph 34, wherein the fluorophore-labeled primer includes a hairpin structure.

36. The method of any preceding paragraph, wherein a region of the template from which the first target is amplified is covalently linked to a region of the template from which the second target is amplified.

37. The method of any preceding paragraph, wherein the first and second targets overlap at a site of allelic variation.

38. The method of paragraph 37, wherein the site of allelic variation is a single-nucleotide polymorphism.

39. The method of paragraph 37 or 38, wherein the first target and the second target are amplified with respective first and second primers that each overlap the site of allelic variation within three nucleotides of a 3' end of each primer.

40. The method of any of paragraphs 37 to 39, wherein each of the first and second primers binds to a different strand of the template to form a base-paired structure having at least one internal mismatch.

41. The method of paragraph 40, wherein the base-paired structure has at least two internal mismatches.

42. The method of any preceding paragraph, wherein the first target does not overlap the second target.

43. The method of any preceding paragraph, wherein the first target overlaps the second target by less than 30 nucleotides.

44. The method of any preceding paragraph, wherein the step of amplifying produces a first amplicon corresponding to the first target and a second amplicon corresponding to the second target, and wherein each amplicon has a length that is less than one-fourth the length of the template.

45. The method of any preceding paragraph, wherein the first and second targets correspond to regions of the template that are separated from each other by more than a length of each target.

46. A method of performing a multiplexed digital assay, the method comprising: (A) providing partitions containing a single-stranded first template and a double-stranded second template having a first strand and a second strand, the first and second templates each being present at partial occupancy in the partitions, the first template and the first strand each providing a first target and the second strand providing a second target; (B) amplifying the first target and the second target in the partitions; (C) collecting data for amplification of the first target and the second target in individual partitions; and (D) determining a level of each of the single-stranded first template and the double-stranded second template based on the data.

47. The method of paragraph 46, wherein the step of amplifying generates amplicons by linear amplification.

48. The method of paragraph 46, wherein the step of amplifying includes a step of performing at least one thermal cycle with a less stringent annealing temperature followed by a plurality of thermal cycles with a more stringent annealing temperature.

49. The method of paragraph 48, wherein the first template is amplified with a primer that binds to the first template at the less stringent annealing temperature but does not bind substantially to the first template at the more stringent annealing temperature.

50. The method of paragraph 49, wherein the primer is a tailed primer having a 3' end region that is complementary to the first template and a 5' end region that is not substantially complementary to the first template.

51. The method of paragraph 50, wherein the 5' end region is at least three nucleotides in length.

52. The method of paragraph 49, wherein the primer has one or more internal mismatches with the first template when based paired with the first template.

53. The method of any of paragraphs 46 to 52, wherein the first template and the first strand of the second template are not identical in sequence to each other and are both amplified with the same primer or pair of primers.

54. The method of any of paragraphs 46 to 53, wherein the first template includes cDNA and the second template is genomic DNA.

55. The method of any of paragraphs 46 to 54, wherein the first template includes RNA and the second template includes DNA.

56. The method of any of paragraphs 46 to 53, wherein the first template includes mature miRNA and the second template includes pre-miRNA.

EXAMPLE 2

Selected Embodiments II

This section presents additional selected embodiments of the present disclosure, related to digital assays with associated targets, as a series of indexed paragraphs.

1. A method of performing a digital assay, the method comprising: (A) forming partitions each including a portion of a sample that contains a first target associated with a second target; (B) collecting data indicating a presence or absence of each target in individual partitions; (C) classifying each of a plurality of the partitions as positive or negative for each of the targets based on the data, wherein partitions having an indicated presence of only the first target in the data are classified as negative for both targets; and (D) determining a level of the first target.

2. The method of paragraph 1, wherein partitions having an indicated presence of only the second target in the data are classified as negative for both targets.

3. The method of paragraph 1 or 2, wherein at least 80% of the first target is associated with the second target when the partitions are formed.

4. The method of paragraph 3, wherein at least 80% of the first target is covalently connected to the second target when the partitions are formed.

5. The method of any of paragraphs 1 to 4, wherein the step of classifying includes a step of classifying at least a majority of partitions having an indicated absence of at least one target in the data as negative for both of the targets.

6. The method of paragraph 5, wherein the step of classifying includes a step of classifying every partition having an indicated absence of at least one target in the data as negative for both of the targets.

7. The method of any of paragraphs 1 to 6, wherein the step of determining a level is based on a first value for a total number of partitions classified and a second value for a number of partitions classified as positive for both targets or a second value for a number of partitions classified as negative for both targets.

8. The method of paragraph 7, wherein the step of determining includes a step of calculating a level of the first target from the first value and the second value.

9. The method of paragraph 8, wherein the step of calculating a level is based on Poisson statistics.

10. The method of paragraph 8 or 9, wherein the level is an average number of copies per partition.

11. The method of any of paragraphs 1 to 10, wherein the partitions are droplets.

12. The method of any of paragraphs 1 to 11, wherein the data indicates that more of the partitions have a presence of the first target than a presence of both targets.

13. The method of paragraph 12, wherein the data indicates that more of the partitions have a presence of the second target than a presence of both targets.

14. The method of any of paragraphs 1 to 13, further comprising a step of plotting at least a portion of the data to form a graph, wherein the step of classifying is based at least in part on positions of clusters of data points in the graph.

15. The method of any of paragraphs 1 to 14, wherein the step of collecting data includes a step of obtaining one or more signal values for each partition, wherein the step of classifying includes a step of comparing the one or more signal values for each partition with one or more threshold or range values to classify the partition.

16. The method of any of paragraphs 1 to 15, wherein the level is a presence or absence indicating whether or not the first target is present above background.

17. The method of any of paragraphs 1 to 16, wherein the sample contains biological particles, and wherein the first target and the second target are contained by the biological particles when the partitions are formed.

18. The method of paragraph 17, wherein the biological particles are selected from the group consisting of biological cells, viruses, and organelles.

19. The method of any of paragraphs 1 to 18, wherein the step of determining a level includes (i) a step of calculating an expected number of double positives based on respective counts of partitions indicated to have a presence of each target alone, and (ii) a step of comparing the expected number of double positives to a count of observed double-positives to determine whether the count of observed double positives is significantly greater the expected number of double positives.

20. The method any of paragraphs 1 to 19, wherein the first target is a first target sequence and the second target is a second target sequence, and wherein the sample includes a template that contains the first target sequence and the second target sequence, and wherein the first target sequence and the second target sequence at least partially overlap each other in the template.

21. The method of paragraph 20, wherein the first target sequence and the second target sequence overlap to define an overlap region, and wherein the overlap region includes at least one site of sequence variation for a taxonomic species that provided the targets.

22. The method of paragraph 21, wherein the at least one site of sequence variation includes a single-nucleotide polymorphism.

23. A method of performing a digital assay, the method comprising: (A) forming partitions containing at least one copy of a template in only a subset of the partitions, the template containing a first target sequence and a second target sequence; (B) amplifying the first target sequence and the second target sequence in the partitions; (C) collecting data for amplification of the first target sequence and the second target sequence in the partitions; (D) processing the data such that a given partition is classified as positive for both targets if the partition tests positive for both targets and is classified as negative for both targets if the partitions tests negative for either or both targets; and (E) determining a concentration of the first target based on the processed data.

24. The method of paragraph 23, wherein a single copy of the template has a first strand and a second strand that are complementary to each other, and wherein the first target sequence is amplifiable selectively from the first strand and the second target sequence is amplifiable selectively from the second strand.

25. The method of paragraph 24, wherein the partitions include a luminophore-labeled primer involved in amplification of the first target sequence.

26. The method of paragraph 25, wherein the luminophore-labeled primer includes a hairpin structure.

27. The method of any of paragraphs 24 to 26, wherein the first target sequence and the second target sequence overlap to define an overlap region, and wherein the overlap region includes at least one site of sequence variation for a biological species that provided the targets.

28. The method of paragraph 27, wherein the at least one site is a single-nucleotide polymorphism.

29. The method of paragraph 27 or 28, wherein the first target sequence and the second target sequence are amplified with a first pair and a second pair of primers, respectively, wherein a primer of the first pair and a primer of the second pair each overlap a site of genetic variation within three nucleotides of a 3' end of the respective primer.

30. The method of paragraph 29, wherein the primer of the first pair binds to a different strand of the template than the primer of the second pair to form a base-paired structure having at least one internal mismatch.

31. The method of paragraph 30, wherein the base-paired structure has at least two internal mismatches.

32. The method of any of paragraphs 23 to 31, wherein the step of amplifying produces a first amplicon corresponding to the first target sequence and a second amplicon corresponding to the second target sequence, and wherein each amplicon has a length that is less than one-fourth the length of the template.

33. The method of any of paragraphs 23 to 32, wherein the first and second target sequences correspond to regions of the template that are separated from each other by more than a length of each target sequence.

34. A method of performing a digital assay, the method comprising: (A) providing partitions containing a single-stranded first template and a double-stranded second template having a first strand and a second strand, the first template and the second template each being present in only a subset of the partitions, the first template and the first strand each including a first target sequence and the second strand including a second target sequence; (B) amplifying the first target sequence and the second target sequence in the partitions; (C) collecting data for amplification of the first target sequence and the second target sequence in individual partitions; and (D) determining a level of each of the single-stranded first template and the double-stranded second template based on the data.

35. The method of paragraph 34, wherein the step of amplifying generates amplicons by linear amplification.

36. The method of paragraph 34 or 35, wherein the step of amplifying includes a step of performing at least one thermal cycle with a less stringent annealing temperature followed by a plurality of thermal cycles with a more stringent annealing temperature.

37. The method of paragraph 36, wherein the first target sequence is amplified with a primer that binds to the first template at the less stringent annealing temperature but does not bind substantially to the first template at the more stringent annealing temperature.

38. The method of paragraph 37, wherein the primer is a tailed primer having a 3' end region that is complementary to at least a region the first template and a 5' end region that is not substantially complementary to the first template.

39. The method of paragraph 38, wherein the 5' end region is at least three nucleotides in length.

40. The method of any of paragraphs 37 to 39, wherein the primer has one or more internal mismatches with the first template when based paired with the first template.

41. The method of any of paragraphs 34 to 40, wherein the first target sequence of the first template and the first target sequence of the first strand are not identical in sequence to each other and are both amplified with a same pair of primers.

42. The method of any of paragraphs 34 to 41, wherein the first template includes cDNA and the second template includes genomic DNA.

43. The method of any of paragraphs 34 to 41, wherein the first template includes RNA and the second template includes DNA.

44. The method of any of paragraphs 34 to 41, wherein the first template includes mature miRNA and the second template includes pre-miRNA.

EXAMPLE 3

Selected Embodiments III

This example describes selected embodiments of the present disclosure related to digital assay of biological particles, or nucleic acid prepared therefrom, and compositions or sets for performing the digital assay. The selected embodiments are presented as a series of numbered paragraphs.

1. A method for identifying a target cell or a target virion comprising: (A) providing a sample comprising at least two cells or virions and/or nucleic acid therefrom; (B) partitioning said sample into a set of partitions; and (C) detecting a presence or an absence of at least two identification signatures within each partition; wherein the presence or absence of the at least two identification signatures in a single partition identifies the cell or virion in said single partition.

2. The method of paragraph 1, wherein the sample comprises at least two cells, or a nucleic acid prepared therefrom.

3. The method of paragraph 1, wherein the sample comprises at least two virions, or a nucleic acid prepared therefrom.

4. The method of paragraph 1, wherein the at least two identification signatures are selected from the group consisting of nucleic acid sequences, metabolites, and proteins.

5. The method of paragraph 4, wherein one identification signature is a nucleic acid sequence comprising a ribsomal sequence selected from the group consisting of a 5S rRNA or 5S rDNA sequence, a 16S rRNA or 16S rDNA sequence, an 18S rRNA or 18S rDNA sequence, a 23S rRNA or 23S rDNA sequence, and a 28S rRNA or 28S rDNA sequence.

6. The method of paragraph 1 or 2, wherein detection of one identification signature indicates the presence or absence of a pathogenicity indicator.

7. The method of paragraph 1 or 2, wherein the at least two identification signatures comprise a ribosomal sequence and a pathogenicity indicator.

8. The method of paragraph 1 or 2, wherein at least two of the identification signatures comprise ribosomal sequences.

9. The method of paragraph 8, wherein one identification signature comprising a ribosomal sequence is species-specific and one identification signature comprising a ribosomal sequence is group specific.

10. The method of paragraph 9, wherein the group specific identification signature is a genus-specific identification signature.

11. The method of paragraph 2, wherein the cells comprise bacterial cells.

12. The method of paragraph 11, wherein the bacterial cells are *Staphylococcus* cells.

13. The method of paragraph 1 or 12, wherein at least one of the identification signatures comprises a signature that detects methicillin resistance.

14. The method of paragraph 13, wherein at least one of the identification signatures comprises a set of species-specific signatures.

15. The method of any of the above paragraphs wherein each signature detects target and non-target cells or virions, but the detection of both signatures specifically detects a target cell or virion.

16. The method of any of the above paragraphs, wherein the average number of identified cells or identified virions in a partition is less than 1, 2, 3, 4, 5, 6, 7, 8, 9, or 10.

17. The method of any of the above paragraphs, wherein the partitioning step generates a set of at least 1000 partitions.

18. The method of any of the above paragraphs, wherein the presence or absence of the at least two identification signatures in a partition identifies the presence or absence of the at least two identification signatures in a single cell or virion residing in said partition with a statistical confidence of greater than about 10%, 20%, 30%, 40%, 50%, 60%, 67%, 75%, 80%, 90%, 95%, or 99%.

19. The method of any one of the above paragraphs, wherein the method further comprises comparing the frequency of co-localization of two identification signatures in a single partition to the frequency of co-localization, thereby determining the number of partitions containing the target cell or virion.

20. The method of any one of the above paragraphs, wherein the step of detecting is performed by amplifying the at least two identification signatures in at least one partition.

21. The method of paragraph 20, wherein the at least two identification signatures that are amplified comprise nucleic acid.

22. The method of paragraph 21, wherein the amplification comprises hybridizing probes to the at least two identification signatures.

23. The method of paragraphs 1-19, wherein the detection of the at least two identification signatures comprises using a first probe to detect one identification signature and using a second probe to detect the other identification signature.

24. The method of paragraph 23, wherein the probes comprise nucleic acids, antibodies, aptamers, or enzymes.

25. The method of paragraph 24, wherein the probes comprising nucleic acids, antibodies, aptamers, or enzymes are conjugated to a detectable label.

26. The method of paragraph 24, wherein the detection comprises amplifying at least one of the probes in partitions containing the at least two identification signatures.

27. The method of paragraph 24, wherein the detection comprises amplifying at least two of the probes in partitions containing the at least two identification signatures.

28. The method of paragraph 24, wherein the detection comprises using at least one of the probes to amplify an identification signature in partitions containing the at least two identification signatures.

29. The method of paragraph 24, wherein the detection comprises using two of the probes to amplify the at least two identification signature in partitions containing the at least two identification signatures.

30. The method of any one of the above paragraphs wherein the presence or absence of at least two identification signatures in at least one partition is compared to a database of identification signature patterns, wherein said comparison identifies the cell or virion in at least one partition.

31. The method of paragraph 2, wherein the cells comprise mammalian cells.

32. The method of paragraph 31, wherein one identification signature is a tissue type identification signature and another identification signature is a tumor marker.

33. The method of paragraph 31, wherein one identification signature is an epigenetic marker.

34. The method of paragraph 33, wherein the epigenetic marker is detected by differential DNA cleavage or chemical detection.

35. The method of paragraph 34, wherein the chemical detection comprises bisulfite conversion.

36. The method of paragraph 34, wherein the differential DNA cleavage detection comprises contacting the DNA with a nuclease.

37. The method of paragraph 36, wherein the differential DNA cleavage detection comprises contacting the DNA with a methylation specific or methylation sensitive nuclease.

38. The method of paragraph 32, wherein the tumor marker is a chemotherapeutic resistance marker, a marker of metastatic potential, or a marker of dysregulated cellular proliferation.

39. The method of, wherein the method comprises detecting at least three identification signatures within each partition.

40. The method of any of the above paragraphs, wherein the method comprises detecting the target cells or virions as a member of a group by presence or absence of a group specific detection reagent, and detecting the species of the cells or virions by the presence or absence of at least one species-specific detection reagent.

41. The method of any of the above paragraphs, wherein the method comprises detecting the target cells or virions as a member of a group by presence of absence of at least one group specific detection reagent, and ruling out a particular species of target cell or virion by the presence or absence of at least one species-specific detection reagent.

42. A composition comprising a partition mixture of less than about 100 nL comprising: (A) less than about 2, 3, 4, 5, 6, 7, 8, 9, or 10 target cells or virions, or nucleic acid prepared therefrom; (B) a group specific identification signature detection reagent; (C) a species-specific identification signature detection reagent; and (D) nucleic acid amplification reagents.

43. The composition of paragraph 42, wherein the group specific detection reagent and the species-specific detection reagent detect 16S rRNA or 16S rDNA.

44. A set of partitions, wherein at least one partition contains a partition mixture of paragraph 42.

45. The set of paragraph 44, wherein at least 100, 200, 300, 500, or 1000 partitions contain a partition mixture of paragraph 42.

EXAMPLE 4

Selected Embodiments IV

This example describes selected embodiments of the present disclosure related to digital assay of biological particles, or nucleic acid prepared therefrom, and compositions or sets for performing the digital assay. The selected embodiments are presented as a series of numbered paragraphs.

1. A method of sample analysis, the method comprising: (A) providing a sample comprising at least two types of biological particles and/or nucleic acid therefrom, wherein each type of biological particle contains a different target set or subset composed of at least one of two or more targets; (B) forming partitions each containing a portion of the sample; (C) determining a presence or absence of each of the two or more targets in each of a plurality of the partitions; and (D) determining a level a type of biological particle containing a particular target set or subset of the two or more targets.

2. The method of paragraph 1, further comprising a step of opening the biological particles in the partitions after the step of forming partitions.

3. The method of paragraph 2, wherein the step of opening includes a step of heating the partitions.

4. The method of paragraph 3, wherein the step of heating includes a step of heating the partitions to a temperature of at least about 50 degrees Celsius.

5. The method of paragraph 3, wherein the step of heating includes a step of heating the partitions to a temperature of at least about 90 degrees Celsius.

6. The method of any of paragraphs 2 to 5, wherein the step of opening includes a step of degrading portions of the biological particles with an enzyme.

7. The method of any of paragraphs 1 to 6, wherein the at least two types of biological particles include the type containing the particular target set or subset and at least two other types, and wherein the step of determining a level includes a step of correcting for chance occurrence, if any, of the particular target set or subset in individual partitions due to co-localization of each of the at least two other types of biological particles, or nucleic acid therefrom, in the individual partitions.

8. The method of any of paragraphs 1 to 7, wherein the level is a presence or an absence of the type of biological particle in the sample.

9. The method of any of paragraphs 1 to 7, wherein the level is a concentration, and wherein the concentration is an average number of copies of the type of biological particle per partition.

10. The method of any of paragraphs 1 to 9, wherein the at least two types of biological particles include at least two types of cells.

11. The method of paragraph 10, wherein the at least two types of cells comprise at least two types of bacterial cells.

12. The method of paragraph 11, wherein the bacterial cells include *Staphylococcus* cells.

13. The method of paragraph 12, wherein at least one of the targets represents methicillin resistance.

14. The method of any of paragraphs 1 to 9, wherein the at least two types of biological particles include at least two types of virions.

15. The method of any of paragraphs 1 to 14, wherein the two or more targets are selected from the group consisting of nucleic acid sequences, metabolites, and proteins.

16. The method of any of paragraphs 1 to 15, wherein at least one target of the two or more targets is a target sequence provided by an RNA.

17. The method of paragraph 16, wherein each of the two or more targets is a target sequence provided by an RNA.

18. The method of paragraph 16 or 17, further comprising a step of generating a complementary DNA from the RNA after the step of forming partitions.

19. The method of paragraph 18, further comprising a step of amplifying a sequence of the complementary DNA.

20. The method of paragraph 18 or 19, wherein the step of generating a complementary DNA is performed with an enzyme having reverse transcriptase activity.

21. The method of any of paragraphs 1 to 20, wherein the two or more targets include a first target and a second target, wherein the at least two types of biological particles include a type containing the first target and not the second target, a type containing the second target and not the first target, and a type containing both the first and second targets, and wherein the step of determining a level of a type of biological particle includes a step of determining a level of the type containing the first target and the second target.

22. The method of paragraph 21, wherein the type containing the first target and the second target and the type containing the first target and not the second target belong to a same taxon that does not include the type containing the second target and not the first target.

23. The method of paragraph 22, wherein the taxon is a genus or a species.

24. The method of any of paragraphs 1 to 23, wherein at least one of the targets is a nucleic acid sequence comprising a ribosomal RNA or DNA sequence.

25. The method of paragraph 24, wherein the ribosomal RNA or DNA sequence is a sequence selected from the group consisting of a 5S ribosomal RNA or DNA sequence, a 16S ribosomal RNA or DNA sequence, an 18S ribosomal RNA or DNA sequence, a 23S ribosomal RNA or DNA sequence, and a 28S ribosomal RNA or DNA sequence.

26. The method of paragraph 24 or 25, wherein the nucleic acid sequence is a DNA sequence provided by genomic DNA.

27. The method of paragraph 24 or 25, wherein the nucleic acid sequence is an RNA sequence provided by ribosomal RNA, further comprising a step of amplifying a complementary DNA sequence formed from the RNA sequence.

28. The method of any of paragraphs 1 to 27, wherein each of at least two of the targets comprises a ribosomal RNA or DNA sequence.

29. The method of paragraph 28, wherein at least one of the targets comprises a ribosomal RNA or DNA sequence that is specific to a particular species of a genus relative to other species of the genus, and wherein at least one of the targets comprises a ribosomal RNA or DNA sequence that is present in a plurality of species of the genus.

30. The method of any of paragraphs 24 to 29, wherein at least one of the targets is a pathogenicity indicator.

31. The method of any of paragraphs 1 to 30, wherein the two or more targets include a set of two or more species-specific targets.

32. The method of any of paragraphs 1 to 31, wherein each partition contains an average of less than three genome-equivalents of nucleic acid from each type of biological particle.

33. The method of any of paragraphs 1 to 32, wherein the step of forming partitions generates at least 1000 partitions.

34. The method of any of paragraphs 1 to 33, wherein only a subset of the partitions contain at least one copy of any one of the targets.

35. The method of any of paragraphs 1 to 34, wherein each target comprises nucleic acid, further comprising a step of amplifying each of the targets in the partitions.

36. The method of paragraph 35, wherein the partitions include one or more reporters collectively sensitive to amplification of each of the targets.

37. The method of paragraph 36, wherein the partitions include a different reporter for each target, and wherein the different reporter binds specifically to only one of the targets and/or only to an amplicon corresponding to one of the targets.

38. The method of paragraph 36, wherein the partitions include a same generic reporter sensitive to amplification of each of the targets.

39. The method of paragraph 36, wherein each reporter comprises a nucleic acid, an antibody, an aptamer, an enzyme, or a combination thereof.

40. The method of any of paragraphs 1 to 39, wherein the presence or absence of the two or more targets in at least one partition is compared to a database of target patterns, wherein the comparison identifies a type of biological particle in the at least one partition.

41. The method of any of paragraphs 1 to 40, wherein the biological particles comprise mammalian cells.

42. The method of paragraph 41, wherein at least one of the targets provides tissue identification and at least one other of the targets is a tumor marker.

43. The method of paragraph 42, wherein the tumor marker is a chemotherapeutic resistance marker, a marker of metastatic potential, or a marker of dysregulated cellular proliferation.

44. The method of paragraph 41, wherein at least one target is an epigenetic marker.

45. The method of paragraph 44, wherein the epigenetic marker is detected by differential DNA cleavage or chemical detection.

46. The method of paragraph 45, wherein the chemical detection comprises bisulfite conversion.

47. The method of paragraph 45, wherein the differential DNA cleavage detection comprises contacting the DNA with a nuclease.

48. The method of paragraph 47, wherein the differential DNA cleavage detection comprises contacting the DNA with a methylation-specific or methylation-sensitive nuclease.

49. The method of any of paragraphs 1 to 48, wherein the two or more targets include at least three targets.

50. The method any of paragraphs 1 to 49, further comprising a step of identifying a type of biological particle in the sample as a member of a group by a presence or absence of a group-specific target and ruling out a particular species for the type of biological particle by the presence or absence of at least one species-specific target.

51. The method of any of paragraphs 1 to 50, further comprising a step of determining a level of each type of biological particle.

52. A set comprising a plurality of partitions each containing a portion of a same sample and each having a volume of less than 100 nL, the sample comprising at least two types of biological particles and/or nucleic acid therefrom, wherein each type of biological particle contains a different target set or subset composed of at least one of two or more targets, the two or more targets including a first target present in a plurality of taxa of the same taxonomic rank a second target present in only one taxon of the plurality of taxa, wherein only a subset of the partitions contain at least one copy of any one of the targets, and wherein each partition also comprises a first reporter to detect the first target and a second reporter to detect the second target, and reagents sufficient for amplification of each of the targets.

53. The set of paragraph 52, wherein the group-specific reporter and the species-specific reporter each bind specifically to a 16S ribosomal RNA or DNA sequence.

54. The set of paragraph 52 or 53, wherein the plurality of partitions includes at least 1000 partitions.

55. The set of any of paragraph 52 to 54, wherein each partition is a droplet, further comprising a continuous phase enclosing all of the droplets.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of analysis, the method comprising:
creating a mixture containing
  (a) a sample comprising nucleic acid isolated from a first type of biological particle and a second type of biological particle, wherein the first type of biological particle provides a first target and a second target having a covalent linkage to one another in the isolated nucleic acid, and wherein the second type of biological particle contains the first target but not the second target,
  (b) reagents for amplification of the first target and the second target, and
  (c) one or more reporters;
forming droplets each containing a portion of the mixture;
amplifying the first target and the second target in the droplets;
detecting at least one signal from the one or more reporters present in individual droplets;
classifying individual droplets as positive or negative for each target based on the at least one signal;
determining a first number of droplets that are positive for both targets, or a first number of droplets that are negative for at least one of the targets;
determining a second number of droplets that are positive for the first target and negative for the second target, or a second number of droplets that are negative for the first target and positive for the second target; and
determining a first level of the first type of biological particle using the first number and a second level of the second type of biological particle using the second number.

2. The method of claim 1, wherein the first level is a presence or an absence of the first type of biological particle in the sample, and wherein the second level is a presence or absence of the second type of biological particle in the sample.

3. The method of claim 1, wherein each of the first level and the second level is an average number of copies of the first type or the second type of biological particle per droplet.

4. The method of claim 1, wherein the sample also comprises nucleic acid isolated from a third type of biological particle containing the second target but not the first target.

5. The method of claim 4, wherein the first type of biological particle and the second type of biological particle belong to a same taxon that does not include the third type of biological particle.

6. The method of claim 5, wherein the taxon is a genus or a species.

7. The method of claim 1, wherein the one or more reporters include different specific reporters for the first target and the second target.

8. The method of claim 1, wherein each of the first type of biological particle and the second type of biological particle includes Staphylococcus cells, and wherein one of the first and second targets represents methicillin resistance.

9. The method of claim 1, wherein at least one of the first and second targets is a nucleic acid sequence comprising a ribosomal RNA or DNA sequence.

10. The method of claim 9, wherein the first target comprises a ribosomal RNA or DNA sequence that is specific to a particular species of a genus relative to other species of the genus, and wherein the second target comprises a ribosomal RNA or DNA sequence that is present in a plurality of species of the genus.

11. The method of claim 1, wherein at least one of the first and second targets is a pathogenicity indicator.

12. The method of claim 1, wherein the step of forming droplets generates at least 1000 droplets.

* * * * *